United States Patent
Zeese et al.

(10) Patent No.: US 12,060,658 B2
(45) Date of Patent: Aug. 13, 2024

(54) WATER SOLUBLE FIBERS WITH POST PROCESS MODIFICATIONS AND ARTICLES CONTAINING SAME

(71) Applicant: MONOSOL, LLC, Merrillville, IN (US)

(72) Inventors: Nicholas Zeese, Merrillville, IN (US); Jonathon Knight, Merrillville, IN (US); Richard Goetz, Merrillville, IN (US); Victoria Bridewell, Merrillville, IN (US); Alyssa Shuey, Merrillville, IN (US)

(73) Assignee: MONOSOL, LLC, Merrillville, IN (US)

( * ) Notice: Subject to any disclaimer, the term of this patent is extended or adjusted under 35 U.S.C. 154(b) by 108 days.

(21) Appl. No.: 17/466,279

(22) Filed: Sep. 3, 2021

(65) Prior Publication Data
US 2022/0074130 A1 Mar. 10, 2022

Related U.S. Application Data

(60) Provisional application No. 63/074,716, filed on Sep. 4, 2020.

(51) Int. Cl.
*D06M 13/203* (2006.01)
*A61L 15/24* (2006.01)
(Continued)

(52) U.S. Cl.
CPC ............. *D01F 11/06* (2013.01); *A61L 15/24* (2013.01); *B32B 5/022* (2013.01); *B32B 5/266* (2021.05);
(Continued)

(58) Field of Classification Search
CPC ............. D06M 13/203; D06M 13/144; D06M 11/38; C08F 216/06; C08L 29/04;
(Continued)

(56) References Cited

U.S. PATENT DOCUMENTS

2011/0268911 A1 11/2011 Zheng et al.
2013/0123738 A1 5/2013 RamosMedina et al.
(Continued)

FOREIGN PATENT DOCUMENTS

| CN | 101392456 A | * 3/2009 | ............. G03G 15/60 |
| CN | 102731710 B | 3/2015 | |

(Continued)

OTHER PUBLICATIONS

English translation of CN-105113222-A to Miao obtained from PE2E database (Year: 2015).*

(Continued)

*Primary Examiner* — Jeremy R Pierce
(74) *Attorney, Agent, or Firm* — BENESCH, FRIEDLANDER, COPLAN & ARONOFF LLP

(57) ABSTRACT

Methods of treating fibers comprising a polymer including at least one of a vinyl acetate moiety or a vinyl alcohol moiety, and resulting fibers or the products comprising the resulting fibers are disclosed. In an example embodiment, a fiber having a surface region and an interior region, includes a polymer comprising at least one of a vinyl acetate moiety or a vinyl alcohol moiety chemically modified with a modification agent. The fiber has a transverse cross-section including the interior region comprising the polymer having a first degree of modification and the surface region comprising the polymer having a second degree of modification greater than the first degree of modification.

29 Claims, 18 Drawing Sheets

(51) Int. Cl.
| | |
|---|---|
| B32B 5/02 | (2006.01) |
| B32B 5/26 | (2006.01) |
| B65D 65/40 | (2006.01) |
| B65D 65/46 | (2006.01) |
| C08F 216/06 | (2006.01) |
| C08F 218/08 | (2006.01) |
| C08L 29/04 | (2006.01) |
| C08L 31/04 | (2006.01) |
| D01F 8/04 | (2006.01) |
| D01F 11/06 | (2006.01) |
| D04H 1/4309 | (2012.01) |
| D04H 1/4382 | (2012.01) |
| D04H 1/732 | (2012.01) |
| D06B 3/02 | (2006.01) |
| D06M 11/38 | (2006.01) |
| D06M 13/144 | (2006.01) |
| D06M 101/24 | (2006.01) |

(52) U.S. Cl.
CPC ............. *B65D 65/40* (2013.01); *B65D 65/46* (2013.01); *C08F 216/06* (2013.01); *C08F 218/08* (2013.01); *C08L 29/04* (2013.01); *C08L 31/04* (2013.01); *D01F 8/04* (2013.01); *D04H 1/4309* (2013.01); *D04H 1/43828* (2020.05); *D04H 1/732* (2013.01); *D06B 3/02* (2013.01); *D06M 11/38* (2013.01); *D06M 13/144* (2013.01); *D06M 13/203* (2013.01); *B32B 2262/0223* (2013.01); *B32B 2262/124* (2021.05); *B32B 2307/7163* (2013.01); *B32B 2307/7166* (2013.01); *B32B 2307/726* (2013.01); *B32B 2439/46* (2013.01); *B32B 2555/02* (2013.01); *C08F 2810/50* (2013.01); *C08L 2203/12* (2013.01); *D06M 2101/24* (2013.01); *D10B 2321/06* (2013.01); *D10B 2401/024* (2013.01); *D10B 2505/10* (2013.01); *D10B 2509/02* (2013.01); *Y10T 428/2967* (2015.01)

(58) Field of Classification Search
CPC ......... C08L 31/04; B32B 5/022; B32B 5/266; D04H 1/732; D04H 1/4309; D04H 1/43828; B65D 65/40; B65D 65/46; A61L 15/24; D01F 11/06; D01F 8/04
See application file for complete search history.

(56) References Cited

U.S. PATENT DOCUMENTS

| | | |
|---|---|---|
| 2013/0296457 A1 | 11/2013 | Krull et al. |
| 2019/0169847 A1* | 1/2019 | Krasnoff et al. .......... E04C 5/00 |
| 2019/0338090 A1 | 11/2019 | Childers et al. |
| 2020/0102524 A1 | 4/2020 | Dreher et al. |

FOREIGN PATENT DOCUMENTS

| | | | |
|---|---|---|---|
| CN | 105113222 A | * 12/2015 | .......... D06M 13/192 |
| WO | 2020/087079 A1 | 4/2020 | |

OTHER PUBLICATIONS

English translation of CN-101392456-A to Jin obtained from PE2E database (Year: 2009).*

International Search Report and Written Opinion dated Dec. 30, 2021 for International PCT Application No. PCT/US2021/049069.

International Search Report and Written Opinion mailed Feb. 8, 2022, for PCT Application No. PCT/US2021/049051, 14 pages.

Drechsler et al., "Surface modification of poly(vinyl alcohol) fibers to control the fiber-matrix interaction in composites." Colloid and Polymer Science (2019): 1-15. https://doi.org/10.1007/s00396-019-04528-z. Abstract; p. 1080 para 3; p. 1082 para 1, 2.

Preliminary Report on Patentability mailed Mar. 16, 2023, for PCT Application No. PCT/US2021/049051, 12 pages.

Preliminary Report on Patentability mailed Mar. 16, 2023, for PCT Application No. PCT/US2021/049069, 8 pages.

* cited by examiner

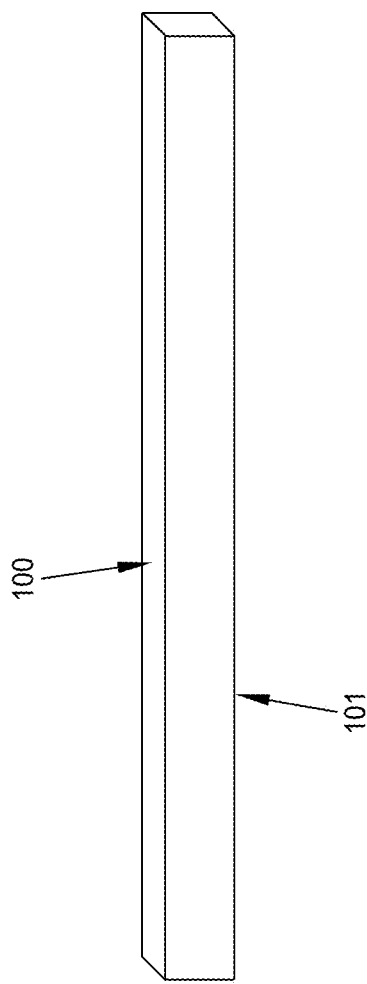

US 12,060,658 B2

WATER SOLUBLE FIBERS WITH POST PROCESS MODIFICATIONS AND ARTICLES CONTAINING SAME

CROSS-REFERENCE TO RELATED APPLICATIONS

This application claims the benefit of U.S. Provisional Application No. 63/074,716, filed Sep. 4, 2020, which application is expressly incorporated by reference herein in its entirety.

FIELD

The present disclosure relates generally to water soluble fibers. More particularly, the disclosure relates to water soluble fibers comprising a modified polymer comprising vinyl acetate moieties and/or vinyl alcohol moieties after fiber formation by chemically modifying the vinyl alcohol moieties in the polymer.

BACKGROUND

Nonwoven webs are traditionally used in many single-use consumer products including personal care products, such as bandages, diaper components, feminine care, and adult incontinence, and single-use wipes, such as in industrial applications, medical applications, cleaning applications, and personal/baby care. Traditional chemistries used in such products, e.g., viscose, polypropylene, or cotton fibers, are generally non-sustainable, non-biodegradable, are potential contributors to microplastics, and are often disposed of incorrectly, such as by flushing down a toilet and entering wastewater treatment and sewage facilities. Known wipes must be disposed of in a bin, which may not be hygienic or convenient for a user. Improper disposal of these articles can result in pipe clogs in the home, formation of "fatbergs" or aggregation of congealed mass of biodegradable and non-biodegradable materials composed of congealed grease and cooking fat and disposable wipes in residential and municipal wastewater systems, contributing to oceanic microplastics, and require a change in consumer behavior.

The solubility profile and mechanism (e.g., hot-water soluble vs. cold-water soluble, readily soluble vs. delayed solubility or extended release) of a water-soluble article may need to be adjusted based on the end use of the article. For articles including water-soluble fibers, the solubility profile and mechanism can be varied by selecting fiber forming materials having different chemical modifications, such as, copolymerization. However, chemical modifications of fiber forming materials also influence the ability of the fiber forming material to form fibers. Thus, a fiber formed of a particular polymer having a desired chemical modification to provide a fiber having a desired solubility profile may not be accessible as the fiber forming material may not survive the fiber making process. Accordingly, it would be advantageous to provide a method for modifying the solubility profile of a fiber after fiber formation, in order to access otherwise unavailable solubility profiles.

Additionally, the solubility profile, bondability, and other properties, such as mechanical properties and chemical compatibility, of a fiber or water-soluble article prepared therefrom can be designed for a particular end use. Thus, it would be advantageous to provide a method for improving bondability, expanding chemical compatibility and/or other properties of a fiber after fiber formation and/or maintaining or modifying the solubility profile of a nonwoven web prior to assembly in a composite in order to manage inventory. Expanded chemical compatibility is used for applications for packaging and delivery. The ability to post-process modify the chemical make-up of a fiber and, thus, the solubility profile of a fiber, would advantageously allow access to various fiber types starting from one or a handful of fiber types. The post-manufacturing fiber modification provides many advantages such as processability, process changes, and/or flexibility of composition.

BRIEF DESCRIPTION OF THE DRAWINGS

For further facilitating the understanding of the present disclosure, twenty-four (24) drawing figures are appended hereto.

FIG. 5 is an illustration of a nonwoven web noting exterior surfaces of the web as 100 and 101, according to example embodiments;

DETAILED DESCRIPTION

Figure 1D:
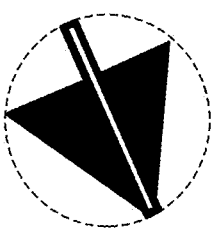
FIGS. 1A-1D show a transverse cross-section of various fiber shapes, wherein a line indicates a diameter of the fiber, according to example embodiments.
Figure 1C:
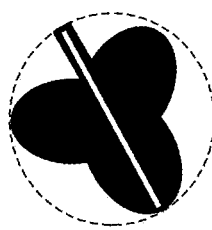
Figure 1B:
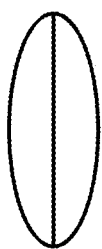
Figure 1A:
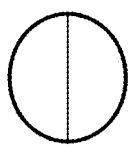

Provided herein are methods of treating fibers to chemically modify a polymer that makes up the fiber, by contacting the fiber or a surface thereof with a modification agent to chemically modify at least a portion of the polymer with the modification agent in a region of the fiber or a surface thereof and form a modified fiber. Also provided herein are method of treating fibers by admixing a fiber comprising a polymer, a modification agent, and optionally a solvent for the modification agent, to chemically modify at least a portion of the polymer with the modification agent and form a modified fiber. In embodiments, the fiber is not soluble in the solvent for a duration of contact of the fiber with the solvent. The methods of the disclosure can advantageously provide a fiber having chemical modification or an increase in the chemical modification of a polymer that makes up the fiber, a fiber having a core-sheath structure wherein the polymer of the sheath or surface region has a different amount of chemical modification (degree of modification) than the polymer of the core or interior region, and/or a fiber having a gradient of the chemical modification of the polymer that makes up the fiber, from an interior region to a surface region. Optionally, the polymer comprises at least one of a vinyl acetate moiety or a vinyl alcohol moiety. As used herein, "at least one of a vinyl acetate moiety or a vinyl alcohol moiety" and "a vinyl acetate moiety and/or a vinyl alcohol moiety" describe an exemplary polymer comprising only a vinyl acetate moiety, only a vinyl alcohol moiety, or both a vinyl acetate moiety and a vinyl alcohol moiety. In the present disclosure, the singular forms "a," "an," and "the" include the plural reference, unless the context clearly indicates otherwise. Thus, for example, a reference to "a vinyl alcohol moiety" is a reference to one or more of such structures and equivalents including vinyl alcohol moieties. For example, such a polymer may be a copolymer comprising both a vinyl acetate moiety and a vinyl alcohol moiety, i.e., a copolymer of vinyl acetate and vinyl alcohol.

One aspect of the disclosure provides a method of treating fibers to chemically modify a polymer that makes up the fiber, by contacting the fiber or a surface thereof with a modification agent to chemically modify at least a portion of the polymer with the modification agent in a region of the fiber or a surface thereof and form a modified fiber. In embodiments, contacting the fiber or a surface thereof with a modification agent includes admixing a fiber comprising a polymer comprising vinyl acetate moieties and/or vinyl alcohol moieties, a modification agent, and optionally a solvent for the modification agent.

Another aspect of the disclosure provides a modified fiber, which is chemically modified with the modification agent, according to the methods of the disclosure.

Another aspect of the disclosure provides a fiber having a surface region and an interior region. The fiber includes a modified polymer comprising vinyl acetate moieties and/or vinyl alcohol moieties. The fiber has a transverse cross-section including the interior region comprising the polymer having a first degree of modification, and the surface region comprising the polymer having a second degree of modification greater than the first degree of modification.

Another aspect of the disclosure provides a fiber comprising a transverse cross-section having a core-sheath structure. The fiber includes a first region, e.g., a core region, comprising the polymer having a first degree of modification, and a second region, e.g., a sheath region, comprising the polymer having a second degree of modification. The second degree of modification is different from, e.g., greater than, the first degree of modification.

Another aspect of the disclosure provides a method of treating a nonwoven web comprising a plurality of fibers. In example embodiments, each fiber of the plurality of fibers includes a polymer comprising vinyl acetate moieties and/or vinyl alcohol moieties. The method includes contacting at least a portion of the nonwoven web with a modification agent to chemically modify the polymer in a region of each fiber therein with the modification agent so as to provide a modified nonwoven web.

Another aspect of the disclosure provides a modified nonwoven web, in which the polymer therein is chemically modified with the modification agent according to the methods of the disclosure.

Another aspect of the disclosure provides a nonwoven web comprising a modified fiber of the disclosure.

Another aspect of the disclosure provides a multilayer nonwoven web comprising a first layer comprising a nonwoven web treated according to the methods of the disclosure or a nonwoven web comprising a fiber of the disclosure.

Another aspect of the disclosure provides a pouch comprising a nonwoven web according to the disclosure in the form of a pouch defining an interior pouch volume.

Another aspect of the disclosure provides a sealed article comprising a nonwoven web of the disclosure.

Another aspect of the disclosure provides a flushable article comprising a nonwoven web of the disclosure.

Another aspect of the disclosure provides a wearable absorbent article, the article comprising an absorbent core having a wearer facing side and an outer facing side and a liquid acquisition layer, wherein the liquid acquisition layer comprises a nonwoven web of the disclosure.

Further aspects and advantages will be apparent to those of ordinary skill in the art from a review of the following detailed description. While the fibers, nonwoven webs, pouches, articles and their methods of making are susceptible of embodiments in various forms, the description hereafter includes specific embodiments with the understanding that the disclosure is illustrative and is not intended to limit the invention to the specific embodiments described herein.

In embodiments, the fibers of the disclosure are water-soluble prior to treatment with the modification agent and remain water-soluble after treatment with the modification agent. In embodiments, the fibers of the disclosure are cold-water soluble prior to treatment with the modification agent and are hot-water soluble after treatment with the modification agent. In embodiments, the fibers of the disclosure are cold-water soluble prior to treatment with the modification agent and at least a portion of the exterior surface of the fiber is hot-water soluble after treatment with the modification agent. In embodiments, the fibers of the disclosure are hot-water soluble prior to treatment with the modification agent and are cold-water soluble after treatment with the modification agent. In embodiments, the fibers of the disclosure are hot-water soluble prior to treatment with the modification agent and at least a portion of the exterior surface of the fiber is cold-water soluble after treatment with the modification agent. In embodiments, the fibers of the disclosure are cold-water soluble prior to treatment with the modification agent and remain cold-water soluble after treatment with the modification agent. In embodiments, the fiber is not water-soluble prior to treatment with the modification agent and the fiber is water-soluble after treatment with the modification agent. In embodiments, the fiber is not water-soluble after admixing the fiber with the modification agent.

The methods and fibers of the disclosure can provide one or more advantages, including but not limited to, providing control over the microstructure of the a fiber, modifying the solubility profile and/or mechanism of a fiber, enhancing the chemical compatibility of a fiber to a chemical agent, increasing the absorbance capacity of a fiber, increasing and/or controlling the loading of an active agent to the interior of a fiber, providing control over the release of a composition or active from the interior of a fiber, increasing inter-fiber cohesion via intermolecular forces and creating crosslinking sites via covalent bond formation, improving processability of the fibers and nonwoven webs formed therefrom (e.g., allowing nonwoven bonding using thru-air bonding, improving tensile strength, providing anchoring points for additional functionality, and allowing triggered delivery of active agents).

Unless expressly indicated otherwise, the term "degree of hydrolysis" is understood as a percentage (e.g., a molar percentage) of hydrolyzed moieties among all hydrolyzable moieties a polymer initially has. For example, for a polymer comprising at least one of a vinyl acetate moiety or a vinyl alcohol moiety, partial replacement of an ester group in vinyl acetate moieties with a hydroxyl group occurs during hydrolysis, and a vinyl acetate moiety becomes a vinyl alcohol moiety. The degree of hydrolysis of a polyvinyl acetate homopolymer is considered as zero, while the degree of hydrolysis of a polyvinyl alcohol homopolymer is 100%. The degree of hydrolysis of a copolymer of vinyl acetate and vinyl alcohol is equal to a percentage of vinyl alcohol moieties among a total of vinyl acetate and vinyl alcohol moieties, and is between zero and 100%.

As used herein and unless specified otherwise, the term "degree of modification" as it relates to chemical modification as described herein, refers to the amount of chemical modification provided to a polymer backbone of a fiber described herein. For example, a polyvinyl alcohol copolymer backbone can include vinyl alcohol monomer units (moieties) and vinyl acetate monomer units (moieties), depending on the degree of hydrolysis, and if a polyvinyl alcohol has been modified by 2 mol % with monomethyl maleate, based on the total amount of vinyl alcohol monomer units and vinyl acetate monomer units, the degree of modification of the polyvinyl alcohol is 2 mol %. As used herein and unless specified otherwise, a copolymer having two or more monomer units in the backbone is not considered a modified polymer, unless the backbone units have been chemically modified after fiber formation, as described herein. For example, a polyvinyl alcohol copolymer comprising vinyl alcohol monomer units, vinyl acetate monomer units, and monomethyl maleate monomer units, wherein the monomethyl maleate monomer units make up 2 mol % of the total backbone monomer units is not considered to have a degree of modification of 2 mol %. However, such a copolymer can be chemically modified by, e.g., 3 mol % monomethyl maleate, to provide a copolymer comprising 2 mol % monomethyl maleate backbone units with a 3 mol % monomethyl maleate modification. As used herein and unless specified otherwise, the terms "chemical modification" and "chemically modify" refer to a modification of a polymer backbone of a fiber, wherein the chemical modification does not include hydrolyzing the polymer and wherein the chemical modification does not increase the amount of backbone monomer units. For example, a polyvinyl alcohol copolymer backbone can include vinyl alcohol monomer units and vinyl acetate monomer units, depending on the degree of hydrolysis, and if the polyvinyl alcohol is said to be chemically modified herein, the total amount of vinyl alcohol monomer units and vinyl acetate monomer units decreases by the amount of chemical modification (degree of modification), relative to the unmodified or non-modified polymer, as the vinyl alcohol monomer units and/or vinyl acetate monomer units have been transformed into a modified monomer unit. It is possible for a polymer of a fiber disclosed herein to have a degree of modification prior to further chemically modifying the polymer of the fiber, and as such, the total degree of modification would include the degree of modification prior to further chemically modifying the polymer of the fiber, added to the degree of modification that occurred from the modification agent disclosed herein. In some embodiments, the hydroxyl (—OH) groups in the vinyl alcohol moieties react with the modification agent and the polymer backbone is chemically boned with the moieties of the modification agent.

As used herein and unless specified otherwise, the term "water-soluble" refers to any nonwoven web or article containing same having a dissolution time of 300 seconds or less at a specified temperature as determined according to a method for testing dissolution time and disintegration time (MSTM-205) as set forth herein, or any fiber having complete dissolution time of less than 30 seconds at a specified temperature according to the method for determining single fiber solubility disclosed herein. For example, the solubility parameters can be characteristic of a nonwoven web having a thickness of 6 mil (about 152 μm), or an article made therefrom. The dissolution time of the nonwoven web optionally can be 200 seconds or less, 100 seconds or less, 60 seconds or less, or 30 seconds or less at a temperature of about 100° C., about 90° C., about 80° C., about 70° C., about 60° C., about 50° C., about 40° C., about 20° C., or about 10° C. In embodiments wherein the dissolution temperature is not specified, the water-soluble nonwoven web has a dissolution time of 300 seconds or less at a temperature no greater than about 100° C. A fiber can have a complete dissolution time of 30 seconds or less at a temperature of about 100° C., about 90° C., about 80° C., about 70° C., about 60° C., about 50° C., about 40° C., about 20° C., or about 10° C. As used herein, a fiber is "insoluble," "water-insoluble," "non-water-soluble" or "insoluble in water" when the fiber has a complete dissolution time of greater than 30 seconds at a specified temperature according to the method for determining single fiber solubility disclosed herein. In embodiments wherein the complete dissolution temperature is not specified, a water-soluble fiber has a complete dissolution time of 30 seconds or less at a temperature no greater than about 100° C. and a water-insoluble fiber has a complete dissolution time of greater than 30 seconds at a temperature no greater than about 100° C. As used herein and unless specified otherwise, the term "cold water-soluble" refers to any nonwoven web having a dissolution time of 300 seconds or less at 10° C. as determined according to MSTM-205. For example, the dissolution time optionally can be 200 seconds or less, 100 seconds or less, 60 seconds or less, or 30 seconds at 10° C. As used herein and unless specified otherwise, the term "cold water-soluble" in connection with a fiber refers to a fiber having a complete dissolution time of 30 seconds or less at a temperature of 10° C. or less, according to the method for determining single fiber solubility disclosed herein.

As used herein and unless specified otherwise, the term "water-dispersible" refers to a nonwoven web, or article containing same wherein upon submersion in water at a specified temperature the nonwoven web or article physically disassociates into smaller constituent pieces. The smaller pieces may or may not be visible to the naked eye, may or may not remain suspended in the water, and may or may not ultimately dissolve. In embodiments wherein a dispersion temperature is not specified, the nonwoven web or pouch will disintegrate in 300 seconds or less at a temperature of about 100° C. or less, according to MSTM-205. For example, the disintegration time optionally can be 200 seconds or less, 100 seconds or less, 60 seconds or less, or 30 seconds or less at a temperature of about 80° C., about 70° C., about 60° C., about 50° C., about 40° C., about 20° C., or about 10° C., according to MSTM-205. For example, such dispersion parameters can be characteristic of a nonwoven web having a thickness of 6 mil (about 152 μm), or an article made therefrom.

As used herein, the term "flushable" refers to an article such as a nonwoven web, or pouch that is dispersible in aqueous environments, for example, a liquid sewage system, such that the disposal of the web(s) or pouch(es) does not result in the catching of such articles within the pipes of a plumbing system or building up over time to cause a blockage of such a pipe. The INDA/EDANA standard for flushability requires that greater than 95% of the starting material must pass through a 12.5 mm sieve after 60 minutes of slosh box testing using 28 RPM (revolutions per minute) and 18° tilt angle. The Flushability Test set forth herein provides a more stringent flushability test. A commercially available nonwoven web in the form of a flushable wipe, herein referred to as Commercial Wipe A, is certified as flushable and has a disintegration time of 20 seconds as measured by the Flushability Test set forth herein. Thus, as used herein and unless specified otherwise, the term "flushable" refers to an article such as a nonwoven web or pouch that has a percent disintegration that meets or exceeds the percent degradation of Commercial Wipe A (20%) as measured by the Flushability Test as set forth herein. Flushable nonwoven webs and articles containing same have the advantage of being more processable in recycling processes or can simply be flushed in, for example, septic and municipal sewage treatment systems such that, after use, the web, structure, or pouch does not need to be landfilled, incinerated, or otherwise disposed of.

As used herein and unless specified otherwise, the term "nonwoven web" refers to a web or sheet comprising, consisting of, or consisting essentially of fibers arranged (e.g., by a carding process) and bonded to each other. Thus, the term nonwoven web can be considered short hand for nonwoven fiber-based webs. Further, as used herein, "nonwoven web" includes any structure including a nonwoven web or sheet, including, for example, a nonwoven web or sheet having a film laminated to a surface thereof. Methods of preparing nonwoven webs from fibers are well known in the art, for example, as described in *Nonwoven Fabrics Handbook*, prepared by Ian Butler, edited by Subhash Batra et al., Printing by Design, 1999, herein incorporated by reference in its entirety. As used herein and unless specified otherwise, the term "film" refers to a continuous film or sheet, e.g., prepared by a casting or extrusion process.

"Comprising" as used herein means that various components, ingredients or steps that can be conjointly employed in practicing the present disclosure. Accordingly, the term "comprising" encompasses the more restrictive terms "consisting essentially of" and "consisting of." The present compositions can comprise, consist essentially of, or consist of any of the required and optional elements disclosed herein. For example, a thermoformed packet can "consist essentially of" a nonwoven web described herein for use of its thermoforming characteristics, while including a non-thermoformed film or nonwoven web (e.g., lid portion), and optional markings on the film, e.g., by inkjet printing. The disclosure illustratively disclosed herein suitably may be practiced in the absence of any element or step, which is not specifically disclosed herein.

All percentages, parts and ratios referred to herein are based upon the total dry weight of the nonwoven web or film composition or total weight of the packet content composition of the present disclosure, as the case may be, and all measurements made are at about 25° C., unless otherwise specified. All such weights as they pertain to listed ingredients are based on the active level and therefore do not include carriers or by-products that may be included in commercially available materials, unless otherwise specified.

All ranges set forth herein include all possible subsets of ranges and any combinations of such subset ranges. By default, ranges are inclusive of the stated endpoints, unless stated otherwise. Where a range of values is provided, it is understood that each intervening value between the upper and lower limit of that range and any other stated or intervening value in that stated range, is encompassed within the disclosure. The upper and lower limits of these smaller ranges may independently be included in the smaller ranges, and are also encompassed within the disclosure, subject to any specifically excluded limit in the stated range. Where the stated range includes one or both of the limits, ranges excluding either or both of those included limits are also contemplated to be part of the disclosure.

It is expressly contemplated that for any number value described herein, e.g., as a parameter of the subject matter described or part of a range associated with the subject matter described, an alternative which forms part of the description is a functionally equivalent range surrounding the specific numerical value (e.g., for a dimension disclosed as "40 mm" an alternative embodiment contemplated is "about 40 mm").

As used herein, the terms packet(s) and pouch(es) should be considered interchangeable. In certain embodiments, the terms packet(s) and pouch(es), respectively, are used to refer to a container made using the nonwoven web and/or film, and to a fully-sealed container preferably having a material sealed therein, e.g., in the form a measured dose delivery system. The sealed pouches can be made from any suitable method, including such processes and features such as heat sealing, solvent welding, and adhesive sealing (e.g., with use of a water-soluble adhesive).

As used herein and unless specified otherwise, the terms "wt. %" and "wt %" are intended to refer to the composition of the identified element in "dry" (non-water) parts by weight of the entire article or composition referred to, for example a nonwoven web or film, including residual moisture in the nonwoven web or film (when applicable), or laminate structure, or parts by weight of a composition enclosed within a pouch (when applicable).

As used herein and unless specified otherwise, the term "PHR" ("phr") is intended to refer to the composition of the identified element in parts per one hundred parts water-soluble polymer (whether PVOH or other polymers, unless specified otherwise) in the polymer-containing article referred to, e.g., a water-soluble film, a fiber, or a nonwoven web, or a solution used to make the fiber or film.

The nonwoven webs, pouches, and related articles and methods of making and use are contemplated to include embodiments including any combination of one or more of the additional optional elements, features, and steps further described below (including those shown in the Examples and figures), unless stated otherwise.

Fiber Forming Materials

In general, the fibers of the disclosure can include a single fiber forming material or a combination (i.e., blend) of fiber forming materials. A single fiber can include one of more water-soluble fiber forming materials, one or more non-water-soluble fiber forming materials, or a combination of water-soluble and non-water-soluble fiber forming materials. The fibers of the disclosure can generally include a synthetic fiber forming material, a natural fiber forming material, a plant based fiber forming material, a bio-based fiber forming material, a biodegradable fiber forming material, a compostable fiber forming material, or a combination thereof. Plant-based fiber forming materials can be naturally occurring (e.g., cotton) or re-constituted (e.g., bamboo).

In general, the fibers of the disclosure include a fiber forming material that, prior to contact with a modification agent, includes a functional group that can be chemically modified. As used herein, functional groups that can be chemically modified generally include, but are not limited to, any functional group that can undergo an esterification, amidation, amination, carboxylation, nitration, acyloin condensation, allylation, acetylaction, imidization, halogenation, sulfonation, alkylation, acetalyzation, enolyzation, nitrosation, and silane coupling. Suitable polymers including a functional group that can be chemically modified include polyvinyl acetate, polyvinyl propionate, polyvinyl alcohol polymers, poly(N-vinylacetamide) polymers, polyvinyl butyral polymers, poly(butyl acrylate) polymers, poly (butyl methacrylate) polymers, cellulose acetate polymers, polyacrylonitrile polymers, poly(N-isopropylacrylamide) polymers, poly(N,N-diethylacrylamide) polymers, poly(N,N-dimethylacrylamide) polymers, polyl(methylvinylether) polymers, poly(N,N-di methylaminoethyl methacrylate) polymers, poly(N-vinylformamide) polymers, poly(N-vinylcaprolactam) polymers, polyvinylpyrrolidone polymers, polylactic acid, and combinations thereof.

In embodiments, the fibers of the disclosure can include a polymer comprising at least one of a vinyl acetate moiety or a vinyl alcohol moiety. In some embodiments, suitable examples of a polymer comprising at least one of a vinyl acetate moiety or a vinyl alcohol moiety include, without limitation, a polyvinyl alcohol homopolymer, a polyvinyl acetate homopolymer, a polyvinyl alcohol copolymer, a modified polyvinyl alcohol copolymer, and combinations thereof. For example, the polyvinyl alcohol copolymer is a copolymer of vinyl acetate and vinyl alcohol in some embodiments. For example, in some embodiments, the modified polyvinyl alcohol copolymer comprises an anionically modified copolymer, which may be a copolymer of vinyl acetate and vinyl alcohol further comprising additional groups such as a carboxylate, a sulfonate, or combinations thereof. Such a polymer comprising at least one of a vinyl acetate moiety or a vinyl alcohol moiety may also include an additional polymer, for example, in a blend. In some embodiments, the hydroxyl (—OH) groups in the vinyl alcohol moieties react with the modification agent for chemical modification of the polymer.

Polyvinyl alcohol is a synthetic polymer generally prepared by the alcoholysis, usually termed hydrolysis or saponification, of polyvinyl acetate. Fully hydrolyzed PVOH, where virtually all the acetate groups have been converted to alcohol groups, is a strongly hydrogen-bonded, highly crystalline polymer which dissolves only in hot water—greater than about 140° F. (about 60° C.). If a sufficient number of acetate groups are allowed to remain after the hydrolysis of polyvinyl acetate, that is the PVOH polymer is partially hydrolyzed, then the polymer is more weakly hydrogen-bonded, less crystalline, and is generally soluble in cold water—less than about 50° F. (about 10° C.). As such, the partially hydrolyzed polymer is a vinyl alcohol-vinyl acetate copolymer that is a PVOH (polyvinyl alcohol) copolymer, but is commonly referred to as "polyvinyl alcohol (PVOH)" or "the PVOH polymer." For brevity, the term "the PVOH polymer" as used herein is understood to encompass a homopolymer, a copolymer, and a modified copolymer comprising vinyl alcohol moieties, for example, 50% or higher of vinyl alcohol moieties. The term "the PVOH fiber" as used herein is understood to encompass a fiber comprising a homopolymer, a copolymer, and a modified copolymer comprising vinyl alcohol moieties, for example, 50% or higher of vinyl alcohol moieties; and a fiber comprising such a polymer chemically modified with a modification agent. The chemically modified fiber may comprise no vinyl alcohol moieties or less than 50% of vinyl alcohol moieties.

The fibers described herein can include polyvinyl acetate, one or more polyvinyl alcohol (PVOH) homopolymers, one or more polyvinyl alcohol copolymers, or a combination thereof. As used herein, the term "homopolymer" generally includes polymers having a single type of monomeric repeating unit (e.g., a polymeric chain consisting of or consisting essentially of a single monomeric repeating unit). For the particular case of PVOH, the term "the PVOH polymer") as an example of a polymer for chemical modification includes copolymers consisting of a distribution of vinyl alcohol monomer units and vinyl acetate monomer units, depending on the degree of hydrolysis (e.g., a polymeric chain consisting of or consisting essentially of vinyl alcohol and vinyl acetate monomer units). In the limiting case of 100% hydrolysis, a PVOH polymer can include a true homopolymer having only vinyl alcohol units. In some embodiments, the fibers and/or films of the disclosure include polyvinyl alcohol copolymers. In some embodiments, the fibers and/or films of the disclosure include hot water-soluble polyvinyl alcohol copolymers.

In some embodiments, the polymer for chemical modification includes a polyvinyl alcohol copolymer or higher polymer (e.g., ter-polymer) including one or more monomers in addition to the vinyl acetate/vinyl alcohol groups. Optionally, the additional monomer is neutral, e.g., provided by an ethylene, propylene, N-vinylpyrrolidone or other non-charged monomer species. Optionally, the additional monomer is cationic, e.g., provided by a positively charged monomer species. Optionally, the additional monomer is anionic. Thus, in some embodiments, the polyvinyl alcohol includes an anionic polyvinyl alcohol copolymer. An anionic polyvinyl alcohol copolymer can include a partially or fully hydrolyzed PVOH copolymer that includes an anionic monomer unit, a vinyl alcohol monomer unit, and optionally a vinyl acetate monomer unit (i.e., when not completely hydrolyzed). In some embodiments, the PVOH copolymer can include two or more types of anionic monomer units. General classes of anionic monomer units which can be used for the PVOH copolymer include the vinyl polymerization units corresponding to sulfonic acid vinyl monomers and their esters, monocarboxylic acid vinyl monomers, their esters and anhydrides, dicarboxylic monomers having a polymerizable double bond, their esters and anhydrides, and alkali metal salts of any of the foregoing. Examples of suitable anionic monomer units include the vinyl polymerization units corresponding to vinyl anionic monomers including vinyl acetic acid, maleic acid, monoalkyl maleate, dialkyl maleate, maleic anhydride, fumaric acid, monoalkyl fumarate, dialkyl fumarate, itaconic acid, monoalkyl itaconate, dialkyl itaconate, citraconic acid, monoalkyl citraconate, dialkyl citraconate, citraconic anhydride, mesaconic acid, monoalkyl mesaconate, dialkyl mesaconate, glutaconic acid, monoalkyl glutaconate, dialkyl glutaconate, glutaconic anhydride, alkyl acrylates, alkyl alkacrylates, vinyl sulfonic acid, allyl sulfonic acid, ethylene sulfonic acid, 2-acrylamido-1-methyl propane sulfonic acid, 2-acrylamide-2-methylpropanesulfonic acid, 2-methylacrylamido-2-methyl-propanesulfonic acid, 2-sulfoethyl acrylate, alkali metal salts of the foregoing (e.g., sodium, potassium, or other alkali metal salts), esters of the foregoing (e.g., methyl, ethyl, or other $C_1$-$C_4$ or $C_6$ alkyl esters), and combinations of the foregoing (e.g., multiple types of anionic monomers or equivalent forms of the same anionic monomer). In some embodiments, the PVOH copolymer can include two or more types of monomer units selected from neutral, anionic, and cationic monomer units.

The level of incorporation of the one or more monomer units in the PVOH copolymers is not particularly limited. In embodiments, the one or more monomer units are present in the PVOH copolymer in an amount in a range of about 1 mol. % or 2 mol. % to about 6 mol. % or 10 mol. % (e.g., at least 1.0, 1.5, 2.0, 2.5, 3.0, 3.5, or 4.0 mol. % and/or up to about 3.0, 4.0, 4.5, 5.0, 6.0, 8.0, or 10 mol. % in various embodiments). In embodiments, the additional monomer units can be an anionic monomer units and the anionic monomer units are present in the PVOH copolymer in an amount in a range of about 1 mol. % or 2 mol. % to about 6 mol. % or 10 mol. % (e.g., at least 1.0, 1.5, 2.0, 2.5, 3.0, 3.5, or 4.0 mol. % and/or up to about 3.0, 4.0, 4.5, 5.0, 6.0, 8.0, or 10 mol. % in various embodiments).

Polyvinyl alcohols can be subject to changes in solubility characteristics. The acetate group in the copolymer of vinyl acetate and vinyl alcohol (PVOH copolymer) is known by those skilled in the art to be hydrolysable by either acid or alkaline hydrolysis. As the degree of hydrolysis increases, a polymer composition made from the PVOH copolymer will have increased mechanical strength but reduced solubility at lower temperatures (e.g., requiring hot water temperatures for dissolution). Accordingly, exposure of a PVOH copolymer to an alkaline environment (e.g., resulting from a laundry bleaching additive) can transform the polymer from one which dissolves rapidly and entirely in a given aqueous environment (e.g., a cold water medium) to one which dissolves slowly and/or incompletely in the aqueous environment, potentially resulting in undissolved polymeric residue at the end of a wash cycle.

PVOH copolymers with pendant carboxyl groups, such as, for example, vinyl alcohol/hydrolyzed methyl acrylate sodium salt polymers, can form lactone rings between neighboring pendant carboxyl and alcohol groups, thus reducing the water solubility of the PVOH copolymer. In the presence of a strong base, the lactone rings can open over the course of several weeks at relatively warm (ambient) and high humidity conditions (e.g., via lactone ring-opening reactions to form the corresponding pendant carboxyl and alcohol groups with increased water solubility). Thus, contrary to the effect observed with PVOH copolymers of vinyl acetate and vinyl alcohol, it is believed that such a PVOH copolymer pendant carboxyl groups can become more soluble due to chemical interactions between the polymer and an alkaline composition inside a pouch during storage.

Specific sulfonic acids and derivatives thereof having polymerizable vinyl bonds can be copolymerized with vinyl acetate to provide cold-water-soluble PVOH polymers, which are stable in the presence of strong bases. The base-catalyzed alcoholysis products of these copolymers, which are used in the formulation of water-soluble film, are vinyl alcohol-sulfonate salt copolymers which are rapidly soluble. The sulfonate group in the PVOH copolymer can revert to a sulfonic acid group in the presence of hydrogen ions, but the sulfonic acid group still provides excellent cold-water solubility to the polymer. In embodiments, vinyl alcohol-sulfonate salt copolymers contain no residual acetate groups (i.e., are fully hydrolyzed) and therefore are not further hydrolysable by either acid or alkaline hydrolysis. Generally, as the amount of comonomer increases, the water solubility increases, thus sufficient inclusion of sulfonate or sulfonic acid groups inhibit hydrogen bonding and crystallinity, enabling solubility in cold water. In the presence of acidic or basic species, the copolymer is generally unaffected, with the exception of the sulfonate or sulfonic acid groups, which maintain excellent cold water solubility even in the presence of acidic or basic species. Examples of suitable sulfonic acid comonomers (and/or their alkali metal salt derivatives) include vinyl sulfonic acid, allyl sulfonic acid, ethylene sulfonic acid, 2-acrylamido-1-methylpropanesulfonic acid, 2-acrylamido-2-methylpropanesufonic acid, 2-methacrylamido-2-methyl propanesulfonic acid and 2-sulfoethyl acrylate, with the sodium salt of 2-acrylamido-2-methylpropanesulfonic acid (AMPS) being a preferred comonomer.

The fiber forming polymers, whether polyvinyl alcohol polymers or otherwise, can be blended. When the polymer blend includes a blend of polyvinyl alcohol polymers, the PVOH polymer blend can include a first PVOH polymer ("first PVOH polymer"), which can include a PVOH copolymer or a modified PVOH copolymer including one or more types of anionic monomer units (e.g., a PVOH ter- (or higher co-) polymer), and a second PVOH polymer ("second PVOH polymer"), which can include a PVOH copolymer or a modified PVOH copolymer including one or more types of anionic monomer units (e.g., a PVOH ter- (or higher co-) polymer). In some aspects, the PVOH polymer blend includes only the first PVOH polymer and the second PVOH polymer (e.g., a binary blend of the two polymers). Alternatively or additionally, the PVOH polymer blend or a fiber or nonwoven web made therefrom can be characterized as being free or substantially free from other polymers (e.g., other polymers generally, other PVOH-based polymers specifically, or both). As used herein, "substantially free" means that the first and second PVOH polymers make up at least 95 wt. %, at least 97 wt. %, or at least 99 wt. % of the total amount of water-soluble polymers in the water-soluble fiber or film. In other aspects, the fiber can include one or more additional water-soluble polymers. For example, the PVOH polymer blend can include a third PVOH polymer, a fourth PVOH polymer, a fifth PVOH polymer, etc. (e.g., one or more additional PVOH copolymers or modified PVOH copolymers, with or without anionic monomer units). For example, the fiber can include at least a third (or fourth, fifth, etc.) water-soluble polymer which is other than a PVOH polymer (e.g., other than PVOH homopolymers or PVOH copolymers, with or without anionic monomer units).

The degree of hydrolysis (DH) of the PVOH copolymers included in the fibers of the present disclosure before chemical modification with a modification agent can be in a range of about 75% to about 99.9% (e.g., about 79% to about 99.9%, about 79% to about 92%, about 80% to about 90%, about 88% to 92%, about 86.5% to about 89%, or about 88%, 90% or 92% such as for cold-water-soluble compositions; about 90% to about 99%, about 92% to about 99%, about 95% to about 99%, about 98% to about 99%, about 98% to about 99.9%, about 96%, about 98%, about 99%, or greater than 99%). As the degree of hydrolysis is reduced, a fiber made from the polymer will have reduced mechanical strength but faster solubility at temperatures below about 20° C. As the degree of hydrolysis increases, a fiber or film made from the polymer will tend to be mechanically stronger and the thermoformability will tend to decrease. The degree of hydrolysis of the PVOH can be chosen such that the water-solubility of the polymer is temperature dependent, and thus the solubility of a fiber made from the polymer is also influenced. In one option the fiber is cold water-soluble. For a copolymer of vinyl acetate and vinyl alcohol that does not include any other monomers (e.g., a copolymer not copolymerized with an anionic monomer) a cold water-soluble fiber, soluble in water at a temperature of less than 10° C., can include PVOH with a degree of hydrolysis in a range of about 75% to about 90%, or in a range of about 80% to about 90%, or in a range of about 85% to about 90%. In another option the fiber is hot water-soluble. For a copolymer of vinyl acetate and vinyl alcohol that does not include any other monomers (e.g., a copolymer not copolymerized with an anionic monomer) a hot water-soluble fiber, soluble in water at a temperature of at least about 60° C., can include PVOH with a degree of hydrolysis of at least about 98%. A copolymer of vinyl acetate and vinyl alcohol may be referred to as a PVOH copolymer, while a copolymer of vinyl acetate and vinyl alcohol including an anionic monomer moiety may be referred to as modified PVOH copolymer or anionically modified PVOH copolymer. Both a PVOH copolymer and a modified PVOH copolymer can be the polymer in a fiber before chemical modification with a modification agent.

The degree of hydrolysis of the polymer blend can also be characterized by the arithmetic weighted, average degree of hydrolysis ($\overline{H^0}$). For example, $\overline{H^0}$ for a PVOH polymer that includes two or more PVOH polymers is calculated by the formula $\overline{H^0}=\Sigma(W_i \cdot H_i)$ where $W_i$ is the weight percentage of the respective PVOH polymer and $H_1$ is the respective degrees of hydrolysis. When a polymer is referred to as having a specific degree of hydrolysis, the polymer can be a single polyvinyl alcohol polymer having the specified degree of hydrolysis or a blend of polyvinyl alcohol polymers having an average degree of hydrolysis as specified.

The viscosity of a PVOH polymer ($\mu$) is determined by measuring a freshly made solution using a Brookfield LV type viscometer with UL adapter as described in British Standard EN ISO 15023-2:2006 Annex E Brookfield Test method. It is international practice to state the viscosity of 4% aqueous polyvinyl alcohol solutions at 20° C. All viscosities specified herein in Centipoise (cP) should be understood to refer to the viscosity of 4% aqueous polyvinyl alcohol solution at 20° C., unless specified otherwise. Similarly, when a polymer is described as having (or not having) a particular viscosity, unless specified otherwise, it is intended that the specified viscosity is the average viscosity for the polymer, which inherently has a corresponding molecular weight distribution, i.e., the weighted natural log average viscosity as described below. It is well known in the art that the viscosity of PVOH polymers is correlated with the weight average molecular weight ($\overline{M}w$) of the PVOH polymer, and often the viscosity is used as a proxy for the $\overline{M}w$.

In embodiments, the PVOH polymer can have a viscosity of about 1.0 to about 50.0 cP, about 1.0 to about 40.0 cP, or about 1.0 to about 30.0 cP, for example about 4 cP, 8 cP, 15 cP, 18 cP, 23 cP, or 26 cP. In embodiments, the PVOH homopolymers and/or copolymers can have a viscosity of about 1.0 to about 40.0 cP, or about 5 cP to about 23 cP, for example, about 1 cP, 1.5 cP, 2 cP, 2.5 cP, 3 cP, 3.5 cP, 4 cP, 4.5 cP, 5 cP, 5.5 cP, 6 cP, 6.5 cP, 7 cP, 7.5 cP, 8 cP, 8.5 cP, 9 cP, 9.5 cP, 10 cP, 11 cP, 12 cP, 13 cP, 14 cP, 15 cP, 17.5 cP, 18 cP, 19 cP, 20 cP, 21 cP, 22 cP, 23 cP, 24 cP, 25 cP, 26 cP, 27 cP, 28 cP, 29 cP, 30 cP, 31 cP, 32 cP, 33 cP, 34 cP, 35 cP, or 40 cP. In embodiments, the PVOH homopolymers and/or copolymers can have a viscosity of about 21 cP to 26 cP. In embodiments, the PVOH homopolymers and/or copolymers can have a viscosity of about 5 cP to about 14 cP. In embodiments, the PVOH homopolymers and/or copolymers can have a viscosity of about 5 cP to about 23 cP.

For reference, in a polymer blend, the first PVOH polymer is denoted as having a first 4% solution viscosity at 20° C. ($\mu_1$), and the second PVOH polymer is denoted as having a second 4% solution viscosity at 20° C. ($\mu_2$). In various embodiments, the first viscosity $\mu_1$ can be in a range of about 4 cP to about 70 cP (e.g., at least about 4, 8, 10, 12, or 16 cP and/or up to about 12, 16, 20, 24, 28, 30, 32, 35, 37, 40, 45, 48, 50, 56, 60, or 70 cP, such as about 4 cP to about 70 cP, about 4 cP to about 60 cP, about 4 cP to about 46 cP, about 4 cP to about 24 cP, about 10 cP to about 16 cP, or about 10 cP to about 20 cP, or about 20 cP to about 30 cP). Alternatively or additionally, the second viscosity $\mu_2$ can be in a range of about 4 cP to about 70 cP (e.g., at least about 4, 8, 10, 12, or 16 cP and/or up to about 12, 16, 20, 24, 28, 30, 32, 35, 37, 40, 45, 48, 50, 56, 60, or 70 cP, such as about 12 cP to about 30 cP, about 10 cP to about 16 cP, or about 10 cP to about 20 cP, or about 20 cP to about 30 cP). When the PVOH polymer blend includes three or more PVOH polymers selected from PVOH polymer and PVOH copolymers, the foregoing viscosity values can apply to each PVOH polymer or PVOH copolymer individually. Thus, the weight-average molecular weight of the water-soluble polymers, including the first PVOH copolymer and the second PVOH copolymer, can be in a range of about 30,000 to about 175,000, or about 30,000 to about 100,000, or about 55,000 to about 80,000, for example. When referring to average viscosity of the PVOH polymer blend, the weighted natural log average viscosity ($\bar{\mu}$) is used. The $\bar{\mu}$ for a PVOH polymer that includes two or more PVOH polymers is calculated by the formula $\bar{\mu}=e^{\Sigma W_i \ln \mu_i}$ where $\mu_i$ is the viscosity for the respective PVOH polymers.

In embodiments wherein the water-soluble fiber includes a blend of a polyvinyl alcohol homopolymer and a polyvinyl alcohol copolymer, the relative amounts of homopolymer and copolymer are not particularly limited. The polyvinyl alcohol homopolymer can make up about 15 wt. % to about 70 wt. % of total weight of the water-soluble polymer blend, for example, at least about 15 wt. %, at least about 20 wt. %, at least about 25 wt. %, at least about 30 wt. %, at least about 40 wt. %, at least about 50 wt. %, or at least about 60 wt. % and up to about 70 wt. %, up to about 60 wt. %, up to about 50 wt. %, up to about 40 wt. %, or up to about 30 wt. %, based on the total weight of the water-soluble polymer blend, and can be a single homopolymer or a blend of one or more homopolymers (e.g., having a difference in viscosity and/or degree of hydrolysis). The remainder of the water-soluble polymer blend can be the water-soluble polyvinyl alcohol copolymer. Without intending to be bound by theory, it is believed that as the amount of homopolymer decreases below about 15 wt. %, the ability of the blend of polyvinyl alcohol homopolymer and copolymer to form a fiber decreases. The water-soluble polyvinyl alcohol copolymer can make up about 30 wt. % to about 85 wt. % of the total weight of the water-soluble polymer blend, for example, at least about 30 wt. %, at least about 40 wt. %, at least about 50 wt. %, at least about 60 wt. %, at least about 70 wt. %, at least about 75 wt. %, or at least about 80 wt. %, and up to about 85 wt. %, up to about 80 wt. %, up to about 70 wt. %, up to about 60 wt. %, up to about 50 wt. %, or up to about 40 wt. %, based on the total weight of the water-soluble polymer blend, and can be a single copolymer or a blend of one or more copolymers. The blend can consist of a polyvinyl alcohol homopolymer and a polyvinyl alcohol copolymer. The blend can consist of a polyvinyl alcohol homopolymer and a plurality of polyvinyl alcohol copolymers. The blend can consist of more than one polyvinyl alcohol homopolymer and more than one polyvinyl alcohol copolymer.

In embodiments, the fibers comprise polyvinyl acetate, a polyvinyl alcohol homopolymer, a polyvinyl alcohol copolymer, a modified polyvinyl alcohol copolymer, or a combination thereof. In embodiments, the fibers comprise a polyvinyl alcohol homopolymer, a polyvinyl alcohol copolymer, a modified polyvinyl alcohol copolymer, or a combination thereof. In embodiments, the fibers comprise a polyvinyl alcohol homopolymer. In embodiments, the fibers comprise a polyvinyl alcohol copolymer. In embodiments, the fibers comprise a polyvinyl alcohol copolymer including an anionic monomer unit (moiety). In embodiment, the fibers comprise an anionic monomer unit and the anionic monomer unit comprises a carboxylate, a sulfonate, or a combination thereof. In embodiments, the polyvinyl alcohol polymer is water-soluble prior to admixing the fiber with the modification agent. In embodiments, the polyvinyl alcohol polymer has a degree of modification in a range of about 0 mol % to about 10 mol %, prior to the addition of the modification agent. In embodiments, the polymer in the fiber before modification with the modification agent has a degree of hydrolysis greater than about 79% and less than about 99.99% (e.g., from about 79% to about 96% or from about 88% to about 99.99%), prior to admixing the fiber with the hydrolysis agent solution.

The fibers of the disclosure can include water-soluble polymers other than PVOH, a PVOH copolymer, and a modified PVOH copolymer, including, without limitation, polyacrylate, water-soluble acrylate copolymer, polyvinyl pyrrolidone, polyethylenimine, pullulan, water-soluble natural polymer including, but not limited to, guar gum, gum Acacia, xanthan gum, carrageenan, and water-soluble starch, water-soluble polymer derivatives including, but not limited to, modified starches, ethoxylated starch, and hydroxypropylated starch, copolymers of the foregoing and a combination of any of the foregoing additional polymers or copolymers. Yet other water-soluble polymers can include polyalkylene oxides, polyacrylamides, polyacrylic acids and salts thereof, water-soluble celluloses, cellulose ethers, cellulose esters, cellulose amides, polyvinyl acetates, polycarboxylic acids and salts thereof, polyamino acids, polyamides, gelatins, methylcelluloses, carboxymethylcelluloses and salts thereof, dextrins, ethylcelluloses, hydroxyethyl celluloses, hydroxypropyl methylcelluloses, maltodextrins, polymethacrylates, and combinations of any of the foregoing. Such water-soluble polymers, whether PVOH or otherwise, are commercially available from a variety of sources.

In embodiments, the fiber includes the polyvinyl alcohol polymer and an additional polymer comprising a polyvinyl alcohol, a polyvinyl acetate, a polyacrylate, a water-soluble acrylate copolymer, a polyvinyl pyrrolidone, a polyethylenimine, a pullulan, a guar gum, a gum Acacia, a xanthan gum, a carrageenan, a starch, a modified starch, a polyalkylene oxide, a polyacrylamide, a polyacrylic acid, a cellulose, a cellulose ether, a cellulose ester, a cellulose amide, a polycarboxylic acid, a polyamino acid, a polyamide, a gelatin, dextrin, copolymers of the foregoing, and a combination of any of the foregoing additional polymers or copolymers.

The fibers can additionally include a water-insoluble fiber forming material. Suitable water-insoluble fiber forming materials include, but are not limited to, cotton, polyester, copolyester, polyethylene (e.g., high density polyethylene and low density polyethylene), polypropylene, wood pulp, fluff pulp, abaca, viscose, insoluble cellulose, insoluble starch, hemp, jute, flax, ramie, sisal, bagasse, banana fiber, lacebark, silk, sinew, catgut, wool, sea silk, mohair, angora, cashmere, collagen, actin, nylon, Dacron, rayon, bamboo fiber, modal, diacetate fiber, triacetate fiber, polyester, copolyester, polylactide (PLA), polyethylene terephthalate (PET), polypropylene (PP), and combinations thereof. In embodiments, the water-insoluble fiber does not include cotton or rayon. In embodiments, the water-insoluble fiber comprises wool, diacetate, triacetate, nylon, PLA, PET, PP, or a combination thereof.

The fibers can further comprise non-fiber forming materials, referred to herein as auxiliary or secondary ingredients. Auxiliary agents can include active agents and processing agents such as, but not limited to active agents, plasticizers, plasticizer compatibilizers, surfactants, lubricants, release agents, fillers, extenders, cross-linking agents, antiblocking agents, antioxidants, detackifying agents, antifoams, nanoparticles such as layered silicate-type nanoclays (e.g., sodium montmorillonite), bleaching agents (e.g., sodium metabisulfite, sodium bisulfite or others), aversive agents such as bitterants (e.g., denatonium salts such as denatonium benzoate, denatonium saccharide, and denatonium chloride; sucrose octaacetate; quinine; flavonoids such as quercetin and naringen; and quassinoids such as quassin and brucine) and pungents (e.g., capsaicin, piperine, allyl isothiocyanate, and resinferatoxin), and other functional ingredients, in amounts suitable for their intended purposes. As used herein and unless specified otherwise, "auxiliary agents" include secondary additives, processing agents, and active agents. Specific such auxiliary agents and processing agents can be selected from those suitable for use in water-soluble fibers, water-insoluble fibers, nonwoven webs, or those suitable for use in water-soluble films.

In embodiments, the fibers of the disclosure are free of auxiliary agents. As used herein and unless specified otherwise, "free of auxiliary agents" with respect to the fiber means that the fiber includes less than about 0.01 wt %, less than about 0.005 wt. %, or less than about 0.001 wt. % of auxiliary agents, based on the total weight of the fiber.

A plasticizer is a liquid, solid, or semi-solid that is added to a material (usually a resin or elastomer) making that material softer, more flexible (by decreasing the glass-transition temperature of the polymer), and easier to process. A polymer can alternatively be internally plasticized by chemically modifying the polymer or monomer. In addition or in the alternative, a polymer can be externally plasticized by the addition of a suitable plasticizing agent. Water is recognized as a very efficient plasticizer for PVOH and other polymers, including but not limited to water-soluble polymers; however, the volatility of water makes its utility limited since polymer films need to have at least some resistance (robustness) to a variety of ambient conditions including low and high relative humidity.

The plasticizer can include, but is not limited to, glycerin, diglycerin, sorbitol, ethylene glycol, diethylene glycol, triethylene glycol, dipropylene glycol, tetraethylene glycol, propylene glycol, polyethylene glycols up to 400 MW, neopentyl glycol, trimethylolpropane, polyether polyols, sorbitol, 2-methyl-1,3-propanediol (MPDiol®), ethanolamines, and a mixture thereof. The total amount of the non-water plasticizer provided in a fiber can be in a range of about 1 wt. % to about 45 wt. %, or about 5 wt. % to about 45 wt. %, or about 10 wt. % to about 40 wt. %, or about 20 wt. % to about 30 wt. %, about 1 wt. % to about 4 wt. %, or about 1.5 wt. % to about 3.5 wt. %, or about 2.0 wt. % to about 3.0 wt. %, for example about 1 wt. %, about 2.5 wt. %, about 5 wt. %, about 10 wt. %, about 15 wt. %, about 20 wt. %, about 25 wt. %, about 30 wt. %, about 35 wt. %, or about 40 wt. %, based on total fiber weight.

Surfactants for use in fibers are well known in the art. Surfactants for use in films are also well known in the art and can suitably be used in the fibers and/or nonwoven webs of the disclosure. Optionally, surfactants are included to aid in the dispersion of the fibers during carding. Suitable surfactants for fibers of the present disclosure include, but are not limited to, dialkyl sulfosuccinates, lactylated fatty acid esters of glycerol and propylene glycol, lactylic esters of fatty acids, sodium alkyl sulfates, polysorbate 20, polysorbate 60, polysorbate 65, polysorbate 80, alkyl polyethylene glycol ethers, lecithin, acetylated fatty acid esters of glycerol and propylene glycol, sodium lauryl sulfate, acetylated esters of fatty acids, myristyl dimethylamine oxide, trimethyl tallow alkyl ammonium chloride, quaternary ammonium compounds, alkali metal salts of higher fatty acids containing about 8 to 24 carbon atoms, alkyl sulfates, alkyl polyethoxylate sulfates, alkylbenzene sulfonates, monoethanolamine, lauryl alcohol ethoxylate, propylene glycol, diethylene glycol, salts thereof and combinations of any of the forgoing.

Suitable surfactants can include the nonionic, cationic, anionic and zwitterionic classes. Suitable surfactants include, but are not limited to, propylene glycols, diethylene glycols, monoethanolamine, polyoxyethylenated polyoxypropylene glycols, alcohol ethoxylates, alkylphenol ethoxylates, tertiary acetylenic glycols and alkanolamides (nonionics), polyoxyethylenated amines, quaternary ammonium salts and quaternized polyoxyethylenated amines (cationics), alkali metal salts of higher fatty acids containing about 8 to 24 carbon atoms, alkyl sulfates, alkyl polyethoxylate sulfates and alkylbenzene sulfonates (anionics), and amine oxides, N-alkylbetaines and sulfobetaines (zwitterionics). Other suitable surfactants include dioctyl sodium sulfosuccinate, lactylated fatty acid esters of glycerin and propylene glycol, lactylic esters of fatty acids, sodium alkyl sulfates, polysorbate 20, polysorbate 60, polysorbate 65, polysorbate 80, lecithin, acetylated fatty acid esters of glycerin and propylene glycol, and acetylated esters of fatty acids, and combinations thereof. In various embodiments, the amount of surfactant in the fiber is in a range of about 0.01 wt. %, to about 2.5 wt. %, about 0.1 wt. % to about 2.5 wt. %, about 1.0 wt. % to about 2.0 wt. %, about 0.01 wt % to 0.25 wt %, or about 0.10 wt % to 0.20 wt %.

In embodiments, the fibers and/or nonwoven webs of the disclosure can include an active agent. The active agent can be added to the fiber itself, or during carding of the nonwoven web, and/or can be added to the nonwoven web prior to bonding. Active agents added to the fibers during carding can be distributed throughout the nonwoven web. Active agents added to the nonwoven web after carding but prior to bonding can be selectively added to one or both faces of the nonwoven web. Additionally, active agents can be added to the surface of pouches or other articles prepared from the nonwoven webs. In embodiments, the active agent is provided as part of the plurality of fibers, dispersed within the nonwoven web, provided on a face of the nonwoven web, or a combination thereof.

The active agent, when present in the fiber and/or nonwoven web in an amount of at least about 1 wt %, or in a range of about 1 wt % to about 99 wt %, provides additional functionality to the nonwoven web. In embodiments, the active agent can comprise one or more components including, but not limited to, enzymes, oils, flavors, colorants, odor absorbers, fragrances, pesticides, fertilizers, activators, acid catalysts, metal catalysts, ion scavengers, detergents, disinfectants, surfactants, bleaches, bleach components, fabric softeners or combinations thereof. In embodiments, the active agent can comprise a colorant, a surfactant, or a combination thereof. The active agent can take any desired form, including as a solid (e.g., powder, granulate, crystal, flake, or ribbon), a liquid, a mull, a paste, a gas, etc., and optionally can be encapsulated.

In certain embodiments, the active agent may comprise an enzyme. Suitable enzymes include enzymes categorized in any one of the six conventional Enzyme Commission (EC) categories, i.e., the oxidoreductases of EC 1 (which catalyze oxidation/reduction reactions), the transferases of EC 2 (which transfer a functional group, e.g., a methyl or phosphate group), the hydrolases of EC 3 (which catalyze the hydrolysis of various bonds), the lyases of EC 4 (which cleave various bonds by means other than hydrolysis and oxidation), the isomerases of EC 5 (which catalyze isomerization changes within a molecule) and the ligases of EC 6 (which join two molecules with covalent bonds). Examples of such enzymes include dehydrogenases and oxidases in EC 1, transaminases and kinases in EC 2, lipases, cellulases, amylases, mannanases, and peptidases (a.k.a. proteases or proteolytic enzymes) in EC 3, decarboxylases in EC 4, isomerases and mutases in EC 5 and synthetases and synthases of EC 6. Suitable enzymes from each category are described in, for example, U.S. Pat. No. 9,394,092, the entire disclosure of which is herein incorporated by reference.

Enzymes for use in laundry and dishwashing applications can include one or more of protease, amylase, lipase, dehydrogenase, transaminase, kinase, cellulase, mannanase, peptidase, decarboxylase, isomerase, mutase, synthetase, synthase, and oxido-reductase enzymes, including oxidoreductase enzymes that catalyze the formation of bleaching agents.

Oils other than fragrances can include flavorants and colorants.

In one class of embodiments the active agent includes a flavor or combination of flavors. Suitable flavors include but are not limited to, spearmint oil, cinnamon oil, oil of wintergreen (methylsalicylate), peppermint oils, and synthetic and natural fruit flavors, including citrus oils.

In some embodiments, the active agent may be a colorant or combination of colorants. Examples of suitable colorants include food colorings, caramel, paprika, cinnamon, and saffron. Other examples of suitable colorants can be found in U.S. Pat. No. 5,002,789, hereby incorporated by reference in its entirety.

Another class of embodiments include one or more odor absorbers as active agents. Suitable odor absorbers for use as active agents according to the disclosure include, but are not limited to, zeolites, and complex zinc salts of ricinoleic acid. The odor absorbing active agent can also comprise fixatives that are well known in the art as largely odor-neutral fragrances, including but not limited to extracts of labdanum, styrax, and derivatives of abietic acid.

Another class of embodiments include one or more fragrances as active agents. As used herein, the term fragrance refers to any applicable material that is sufficiently volatile to produce a scent. Embodiments including fragrances as active agents can include fragrances that are scents pleasurable to humans, or alternatively fragrances that are scents repellant to humans, animals, and/or insects. Suitable fragrances include, but are not limited to, fruits including, but not limited to, lemon, apple, cherry, grape, pear, pineapple, orange, strawberry, raspberry, musk and flower scents including, but not limited to, lavender-like, rose-like, iris-like and carnation-like. Optionally the fragrance is one that is not also a flavoring. Other fragrances include herbal scents including, but not limited to, rosemary, thyme, and sage; and woodland scents derived from pine, spruce and other forest smells. Fragrances may also be derived from various oils, including, but not limited to, essential oils, or from plant materials including, but not limited to, peppermint, spearmint and the like. Suitable fragrant oils can be found in U.S. Pat. No. 6,458,754, hereby incorporated by reference in its entirety.

Fragrances can include perfumes. The perfume may comprise neat perfume, encapsulated perfume, or mixtures thereof. Preferably, the perfume includes neat perfume. A portion of the perfume may be encapsulated in a core-shell encapsulate. In another type of embodiment, the perfume will not be encapsulated in a core/shell encapsulate.

As used herein, the term "perfume" encompasses the perfume raw materials (PRMs) and perfume accords. The term "perfume raw material" as used herein refers to compounds having a molecular weight of at least about 100 g/mol and which are useful in imparting an odor, fragrance, essence or scent, either alone or with other perfume raw materials. As used herein, the terms "perfume ingredient" and "perfume raw material" are interchangeable. The term "accord" as used herein refers to a mixture of two or more PRMs.

Applicable insect repellant fragrances include one or more of dichlorvos, pyrethrin, allethrin, naled and/or fenthion pesticides disclosed in U.S. Pat. No. 4,664,064, incorporated herein by reference in its entirety. Suitable insect repellants are citronellal (3,7-dimethyl-6-octanal), N,N-diethyl-3-methylbenzamide (DEET), vanillin, and the volatile oils extracted from turmeric (*Curcuma longa*), kaffir lime (*Citrus hystrix*), citronella grass (*Cymbopogon winterianus*) and hairy basil (*Ocimum americanum*). Moreover, applicable insect repellants can be mixtures of insect repellants.

In one class of embodiments, the active agents according to the disclosure can comprise one or more pesticides. Suitable pesticides may include, but are not limited to, insecticides, herbicides, acaricides, fungicides, and larvacides.

Another class of embodiments include one or more fertilizers as active agents. As used herein, the term fertilizer applies to any applicable material that releases one or more of nitrogen, phosphorus, potassium, calcium, magnesium, sulfur, boron, chlorine, copper, iron, manganese, molybdenum, or zinc. Suitable fertilizers include, but are not limited to zeolites. For example, clinoptilolite is a zeolite that releases potassium and can also release nitrogen when preloaded with ammonium.

One class of embodiments comprise acid catalysts as active agents. As used herein, the term acid catalysts refers to any species that serves as a proton source, thereby facilitating a chemical reaction. In one type of embodiment, the acid catalyst will be a non-oxidizing organic acid. A suitable organic acid is para-toluenesulfonic acid. In some embodiments, active agents that are acid catalysts will facilitate reactions including, but not limited to, acetalization, esterification or transesterification. Additional acid catalyzed reactions are well known in the art.

In one class of embodiments, active agents will include metal catalysts. These catalysts mediate reactions including, but not limited to, oxidation or reduction, hydrogenation, carbonylation, C—H bond activation, and bleaching. Suitable metals for use as metal catalysts include, but are not limited to the VIIIA and IB transition metals, for example, iron, cobalt, nickel, copper, platinum, rhodium, ruthenium, silver, osmium, gold and iridium. The metal that mediates catalysis can be of any suitable oxidation state.

In alternative embodiments, the active agent may optionally be an ion scavenger. Suitable ion scavengers include, but are not limited to, zeolites. Optionally, zeolites can be added to water-soluble packets comprising laundry detergents or dish washing detergents enclosed within, as a water softener.

Inorganic and organic bleaches are suitable cleaning active agents for use herein. Inorganic bleaches include perhydrate salts including, but not limited to, perborate, percarbonate, perphosphate, persulfate and persilicate salts. The inorganic perhydrate salts are normally the alkali metal salts. Alkali metal percarbonates, particularly sodium percarbonate are suitable perhydrates for use herein. Organic bleaches can include organic peroxyacids including diacyl and tetraacylperoxides, especially, but not limited to, diperoxydodecanedioc acid, diperoxytetradecanedioc acid, and diperoxyhexadecanedioc acid. Dibenzoyl peroxide is a suitable organic peroxyacid according to the disclosure. Other organic bleaches include the peroxy acids, particular examples being the alkylperoxy acids and the arylperoxy acids.

In one class of embodiments, active agents can comprise bleach sensitizers, including organic peracid precursors that enhance the bleaching action in the course of cleaning at temperatures of 60° C. and below. Bleach sensitizers suitable for use herein include compounds which, under perhydrolysis conditions, give aliphatic peroxoycarboxylic acids having from 1 to 10 carbon atoms, or from 2 to 4 carbon atoms, and/or optionally substituted perbenzoic acid. Suitable substances bear O-acyl and/or N-acyl groups of the number of carbon atoms specified and/or optionally substituted benzoyl groups. Suitable substances include, but are not limited to, polyacylated alkylenediamines, in particular tetraacetylethylenediamine (TAED), acylated triazine derivatives, in particular 1,5-diacetyl-2,4-dioxohexahydro-1,3,5-triazine (DADHT), acylated glycolurils, in particular tetraacetylglycoluril (TAGU), N-acylimides, in particular N-nonanoylsuccinimide (NOSI), acylated phenolsulfonates, in particular n-nonanoyl- or isononanoyloxybenzenesulfonate (n- or iso-NOBS), carboxylic anhydrides, in particular phthalic anhydride, acylated polyhydric alcohols, in particular triacetin, ethylene glycol diacetate and 2,5-diacetoxy-2,5-dihydrofuran and also triethylacetyl citrate (TEAC).

In embodiments that comprise fabric softeners as active agents, various through-the-wash fabric softeners, especially the impalpable smectite clays of U.S. Pat. No. 4,062,647, incorporated herein by reference in its entirety, as well as other softener clays known in the art, can optionally be used to provide fabric softener benefits concurrently with fabric cleaning. Clay softeners can be used in combination with amine and cationic softeners as disclosed, for example, in U.S. Pat. Nos. 4,375,416 and 4,291,071, incorporated herein by reference in their entireties.

In embodiments, the active agent can include disinfectants. Disinfectants suitable for use herein can include, but are not limited to, hydrogen peroxide, inorganic peroxides and precursors thereof, sodium metabisulfite, quaternary ammonium cation based compounds, chlorine, activated carbon, and hypochlorite.

In embodiments, the active agent can include surfactants. Suitable surfactants for use herein can include, but are not limited to, propylene glycols, diethylene glycols, monoethanolamine, polyoxyethylenated polyoxypropylene glycols, alcohol ethoxylates, alkylphenol ethoxylates, tertiary acetylenic glycols and alkanolamides (nonionics), polyoxyethylenated amines, quaternary ammonium salts and quaternized polyoxyethylenated amines (cationics), alkali metal salts of higher fatty acids containing about 8 to 24 carbon atoms, alkyl sulfates, alkyl polyethoxylate sulfates and alkylbenzene sulfonates (anionics), amine oxides, N-alkylbetaines and sulfobetaines (zwitterionics), dioctyl sodium sulfosuccinate, lactylated fatty acid esters of glycerin and propylene glycol, lactylic esters of fatty acids, sodium alkyl sulfates, polysorbate 20, polysorbate 60, polysorbate 65, polysorbate 80, lecithin, acetylated fatty acid esters of glycerin and propylene glycol, and acetylated esters of fatty acids, and combinations thereof.

Active agents may be solids or liquids. Active agents that are solids can have an average particle size (e.g., Dv50) of at least about 0.01 µm, or a size in a range of about 0.01 µm to about 2 mm, for example. Liquid active agents may be applied directly to the nonwoven web, mixed with a carrier powder, or microencapsulated. In embodiments that comprise a carrier powder, the average particle size of the carrier powder can be at least about 0.01 µm, or in a range of about 0.01 µm to about 2 mm, for example.

In one class of embodiments the active agent is encapsulated, allowing for the controlled release of the active agent. Suitable microcapsules can include or be made from one or more of melamine formaldehyde, polyurethane, urea formaldehyde, chitosan, polymethyl methacrylate, polystyrene, polysulfone, poly tetrahydrofuran, gelatin, gum arabic, starch, polyvinyl pyrrolidone, carboxymethylcellulose, hydroxyethylcellulose, methylcellulose, arabinogalactan, polyvinyl alcohol, polyacrylic acid, ethylcellulose, polyethylene, polymethacrylate, polyimide, poly (ethylenevinyl acetate), cellulose nitrate, silicones, poly(lactideco-glycolide), paraffin, carnauba, spermaceti, beeswax, stearic acid, stearyl alcohol, glyceryl stearates, shellac, cellulose acetate phthalate, zein, and combinations thereof. In one type of embodiment, the microcapsule is characterized by a mean particle size (e.g., Dv50) of at least about 0.1 micron, or in a range of about 0.1 micron to about 200 microns, for example. In alternate embodiments, the microcapsules can form agglomerates of individual particles, for example wherein the individual particles have a mean particle size of at least about 0.1 micron, or in a range of about 0.1 micron to about 200 microns.

The fibers to be treated can be formed by any process known in the art, for example, wet cool gel spinning, thermoplastic fiber spinning, melt blowing, spun bonding, electro-spinning, rotary spinning, continuous filament producing operations, tow fiber producing operations, and combinations thereof.

In embodiments, the fibers comprise fibers formed by wet cool gel spinning, melt blowing, spun bonding, or a combination thereof. In embodiments, the fibers comprise fibers that are formed by wet cool gel spinning. In embodiments, the fibers comprise water-soluble fibers and nonwoven webs prepared therefrom are formed in a continuous melt blown process. In embodiments, the fibers comprise water-soluble fibers and nonwoven webs prepared therefrom are formed in a continuous spun bond process. It is standard in the art to refer to fibers and nonwoven webs by the process used to prepare the same. Thus, any reference herein to, for example, a "melt blown fiber" or a "carded nonwoven web" should not be understood to be a product-by-process limitation for a particular melt blown or carding method, but rather merely identifying a particular fiber or web. Processing terms may therefore be used to distinguish fibers and/or nonwovens, without limiting the recited fiber and/or nonwoven to preparation by any specific process.

The fibers to be treated can be formed as bicomponent fibers. As used herein, and unless specified otherwise, "bicomponent fibers" do not refer to a fiber including a blend of fiber forming materials but, rather, refer to fibers including two or more distinct regions of fiber forming materials, wherein the composition of the fiber forming materials differ by region. Examples of bicomponent fibers include, but are not limited to, core-sheath bicomponent fibers, island in the sea bicomponent fibers, and side-by-side bicomponent fibers. Core-sheath bicomponent fibers generally include a core having a first composition of fiber forming materials (e.g., a single fiber forming material or a first blend of fiber forming materials) and a sheath having a second composition of fiber forming materials (e.g., a single fiber forming material that is different from the core material, or a second blend of fiber forming materials that is different from the first blend of fiber forming materials of the core). Island in the sea bicomponent fibers generally include a first, continuous, "sea" region having a first composition of fiber forming materials and discreet "island" regions dispersed therein having a second composition of fiber forming materials that is different from the first composition. Side-by-side bicomponent fibers generally include a first region running the length of the fiber and including a first composition of fiber forming materials adjacent to at least a second region running the length of the fiber and including second composition of fiber forming materials that is different from the first composition. Such bicomponent fibers are well known in the art.

The shape of the fiber is not particularly limited and can have transverse cross-sectional shapes including, but is not limited to, round, oval (also referred to as ribbon), triangular (also referred to as delta), trilobal, and/or other multi-lobal shapes. (FIG. 1). It will be understood that the shape of the fiber need not be perfectly geometric, for example, a fiber having a round transverse cross-sectional shape need not have a perfect circle as the transverse cross-sectional area, and a fiber having a triangular transverse cross-sectional shape generally has rounded corners.

It will be understood that the diameter of a fiber refers to the transverse cross-section diameter of the fiber along the longest transverse cross-sectional axis. When a fiber is described as having (or not having) a particular diameter, unless specified otherwise, it is intended that the specified diameter is the average diameter for the specific fiber type referenced, i.e., a plurality of fibers prepared from polyvinyl alcohol fiber forming material has an arithmetic average fiber diameter over the plurality of fibers. For shapes not typically considered to have a "diameter", e.g., a triangle or a multi-lobal shape, the diameter refers to the diameter of a circle circumscribing the fiber shape (FIG. 1).

The fibers of the disclosure typically have a diameter in a range of about 10 micron to 300 micron, for example, at least 10 micron, at least 15 micron, at least 20 micron, at least 25 micron, at least 50 micron, at least 100 micron, or at least 125 micron and up to about 300 micron, up to about 275 micron, up to about 250 micron, up to about 225 micron, up to about 200 micron, up to about 100 micron, up to about 50 micron, up to about 45 micron, up to about 40 micron, or up to about 35 micron for example in a range of about 10 micron to about 300 micron, about 50 micron to about 300 micron, about 100 micron to about 300 micron, about 10 micron to about 50 micron, about 10 micron to about 45 micron, or about 10 micron to about 40 micron. In embodiments, the fibers can have a diameter greater than 100 micron to about 300 micron. In embodiments, the fibers comprise cellulose and have a diameter in a range of about 10 micron to about 50 micron, about 10 micron to about 30 micron, about 10 micron to about 25 micron, about 10 micron to about 20 micron, or about 10 micron to about 15 micron. In embodiments, the fibers comprise a water-soluble fiber forming material and have a diameter of about 50 micron to about 300 micron, about 100 micron to about 300 micron, about 150 micron to about 300 micron, or about 200 micron to about 300 micron. In embodiments, the diameters of a plurality of the water-soluble fibers used to prepare a nonwoven web of the disclosure have diameters that are substantially uniform. As used herein, fiber diameters are "substantially uniform" if the variance in diameter between fibers is less than 10%, for example 8% or less, 5% or less, 2% or less, or 1% or less. Fibers having substantially uniform diameters can be prepared by a wet cooled gel spinning process or a thermoplastic fiber spinning process. Further, when a blend of fiber types are used, the average diameter of the fiber blend can be determined using a weighted average of the individual fiber types.

The fibers of the disclosure can generally be of any length. In embodiments, the length of the fibers can be in a range of about 20 mm to about 100 mm, about 20 to about 90, about 30 mm to about 80 mm, about 10 mm to about 60 mm, or about 30 mm to about 60 mm, for example, at least about 30 mm, at least about 35 mm, at least about 40 mm, at least about 45 mm, or at least about 50 mm, and up to about 100 mm, up to about 95 mm, up to about 90 mm, up to about 80 mm, up to about 70 mm, or up to about 60 mm. In embodiments, the length of the fibers can be less than about 30 mm or in a range of about 0.25 mm to less than about 30 mm, for example, at least about 0.25 mm, at least about 0.5 mm, at least about 0.75 mm, at least about 1 mm, at least about 2.5 mm, at least about 5 mm, at least about 7.5 mm, or at least about 10 mm and up to about 29 mm, up to about 28 mm, up to about 27 mm, up to about 26 mm, up to about 25 mm, up to about 20 mm, or up to about 15 mm. The fibers can be prepared to any length by cutting and/or crimping an extruded polymer mixture. In embodiments, the fiber can be a continuous filament, for example, prepared by processes such as spun bonding, melt blowing, electro-spinning, and rotary spinning wherein a continuous filament is prepared and provided directly into a web form. Further, when a blend of fiber types are used, the average length of the fibers can be determined using a weighted average of the individual fiber types.

Figures 4A, 4B:
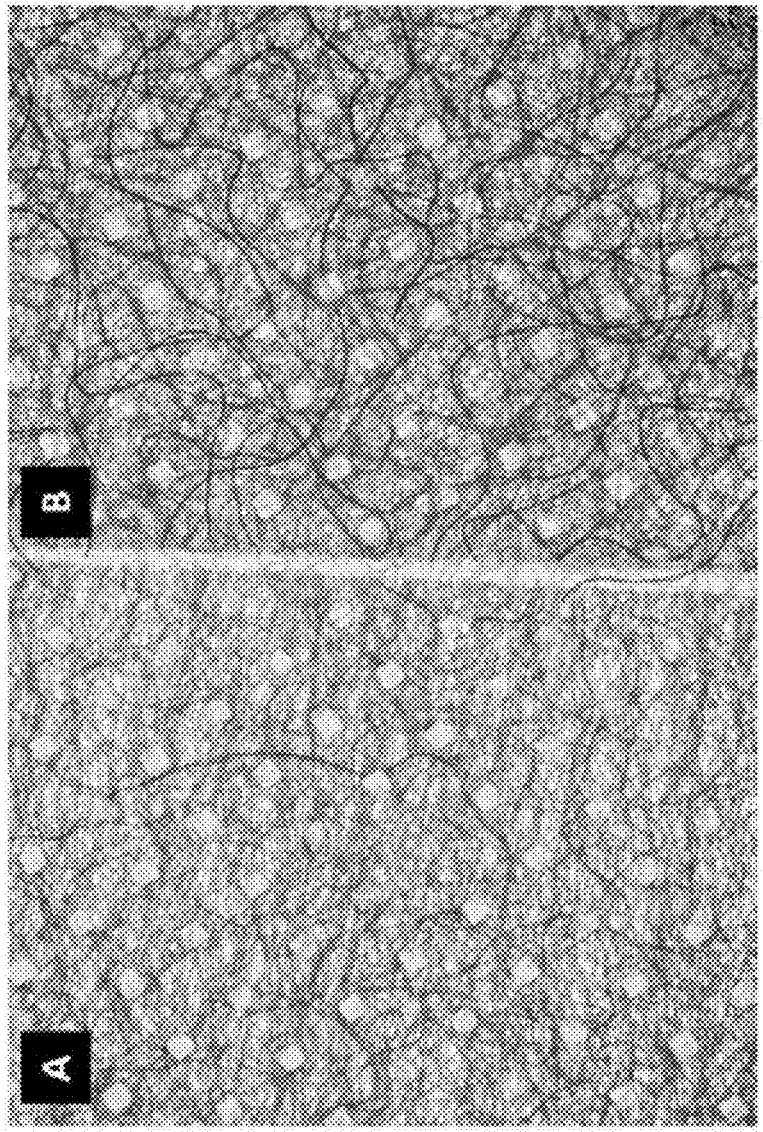
FIG. 4A is a micrograph image of a nonwoven web of the disclosure having a softness rating of 1, according to example embodiments.
FIG. 4B is a micrograph image of a nonwoven web of the disclosure having a softness rating of 5, according to example embodiments.

The fibers of the disclosure can generally have any length to diameter (L/D) ratio. In embodiments, length to diameter ratio of the fibers can be greater than about 2, greater than about 3, greater than about 4, greater than about 6, greater than about 10, greater than about 50, greater than about 60, greater than about 100, greater than about 200, greater than about 300, greater than about 400, or greater than about 1000. Advantageously, the tactility of a nonwoven web can be controlled using the L/D ratio of the fibers and the respective amounts of fibers having various L/D ratios in the nonwoven composition. In general, as the L/D of the fiber decreases, the stiffness and resistance to bending increases, providing a rougher hand feel. The fibers of the disclosure generally impart a rough feel to a nonwoven web including same, when the fibers have a low L/D ratio in a range of about 0.5 to about 15, or about 0.5 to about 25, or about 1 to about 5. Such low L/D fibers can be provided in a nonwoven web in an amount in a range of about 0 to about 50% by weight, based on the total weight of the fibers in the nonwoven web, for example, in a range of about 0.5 wt. % to about 25 wt. %, or about 1 wt. % to about 15 wt. %. If the amount of low L/D fibers in a nonwoven web is not known, the amount can be estimated by visual inspection of a micrograph of a nonwoven web. As shown in FIG. 4, the population of fibers having a visibly larger diameter and shorter cut rate, based on the total fiber population can be observed. FIG. 4A is a micrograph of a nonwoven web having 0% of low L/D fibers and a softness rating of 1, whereas FIG. 4B is a micrograph of a nonwoven web having 25% of low L/D fibers and a softness rating of 5.

The fibers of the disclosure can generally have any tenacity. The tenacity of the fiber correlates to the coarseness of the fiber. In general, as the tenacity of the fiber decreases the coarseness of the fiber increases. Fibers of the disclosure can have a tenacity in a range of about 1 to about 100 cN/dtex, or about 1 to about 75 cN/dtex, or about 1 to about 50 cN/dtex, or about 1 to about 45 cN/dtex, or about 1 to about 40 cN/dtex, or about 1 to about 35 cN/dtex, or about 1 to about 30 cN/dtex, or about 1 to about 25 cN/dtex, or about 1 to about 20 cN/dtex, or about 1 to about 15 cN/dtex, or about 1 to about 10 cN/dtex, or about 1 to about 5 cN/dtex, or about 3 to about 8 cN/dtex, or about 4 to about 8 cN/dtex, or about 6 to about 8 cN/dtex, or about 4 to about 7 cN/dtex, or about 10 to about 20, or about 10 to about 18, or about 10 to about 16, or about 1 cN/dtex, about 2 cN/dtex, about 3 cN/dtex, about 4 cN/dtex, about 5 cN/dtex, about 6 cN/dtex, about 7 cN/dtex, about 8 cN/dtex, about 9 cN/dtex, about 10 cN/dtex, about 11 cN/dtex, about 12 cN/dtex, about 13 cN/dtex, about 14 cN/dtex, or about 15 cN/dtex. In embodiments, the fibers can have a tenacity of about 3 cN/dtex to about 10 cN/dtex. In embodiments, the fibers can have a tenacity of about 7 cN/dtex to about 10 cN/dtex. In embodiments, the fibers can have a tenacity of about 4 cN/dtex to about 8 cN/dtex. In embodiments, the fibers can have a tenacity of about 6 cN/dtex to about 8 cN/dtex.

The fibers of the disclosure can generally have any fineness. The fineness of the fiber correlates to how many fibers are present in a transverse cross-section of a yarn of a given thickness. Fiber fineness is the ratio of fiber mass to length. The main physical unit of fiber fineness is 1 tex, which is equal to 1000 m of fiber weighing 1 g. Typically, the unit dtex is used, representing 1 g/10,000 m of fiber. The fineness of the fiber can be selected to provide a nonwoven web having suitable stiffness/hand-feel of the nonwoven web, torsional rigidity, reflection and interaction with light, absorption of dye and/or other actives/additives, ease of fiber spinning in the manufacturing process, and uniformity of the finished article. In general, as the fineness of the fibers increases the nonwovens resulting therefrom demonstrate higher uniformity, improved tensile strengths, extensibility and luster. Additionally, without intending to be bound by theory it is believed that finer fibers will lead to slower dissolution times as compared to larger fibers based on density. Further, without intending to be bound by theory, when a blend of fibers is used, the average fineness of the fibers can be determined using a weighted average of the individual fiber components. Fibers can be characterized as very fine (dtex≤1.22), fine (1.22≤dtex≤1.54), medium (1.54≤dtex≤1.93), slightly coarse (1.93≤dtex≤2.32), and coarse (dtex≥2.32). The nonwoven web of the disclosure can include fibers that are very fine, fine, medium, slightly coarse, or a combination thereof. In embodiments, the fibers have a fineness in a range of about 1 dtex to about 10 dtex, about 1 dtex to about 7 dtex, about 1 dtex to about 5 dtex, about 1 dtex to about 3 dtex, or about 1.7 dtex to about 2.2 dtex. In embodiments, fibers have a fineness of about 1.7 dtex. In embodiments, fibers have a fineness of about 2.2 dtex.

Wet Cooled Gel Spinning

In embodiments, the fibers of the disclosure are formed according to a wet cooled gel spinning process, the wet cooled gel spinning process including the steps of (a) dissolving the fiber forming material (polymers) in solution to form a polymer mixture, the polymer mixture optionally including auxiliary agents;

(b) extruding the polymer mixture through a spinneret nozzle to a solidification bath to form an extruded polymer mixture;

(c) passing the extruded polymer mixture through a solvent exchange bath;

(d) optionally wet drawing the extruded polymer mixture; and (e) finishing the extruded polymer mixture to provide the fibers.

The solvent in which the fiber forming polymer is dissolved can suitably be any solvent in which the polymer is soluble. In embodiments, the solvent in which the polymer is dissolved includes a polar aprotic solvent. In embodiments, the solvent in which the polymer is dissolved includes dimethyl sulfoxide (DMSO).

In general, the solidification bath includes a cooled solvent for gelling the extruded polymer mixture. The solidification bath can generally be at any temperature that facilitates solidification of the extruded polymer mixture. The solidification bath can include a mixture of a solvent in which the polymer is soluble and a solvent in which the polymer is not soluble. The solvent in which the polymer is not soluble is generally the primary solvent, wherein the solvent in which the polymer is not soluble makes up greater than 50% of the mixture.

After passing through the solidification bath, the extruded polymer mixture gel can be passed through one or more solvent replacement baths. The solvent replacement baths are provided to replace the solvent in which the polymer is soluble with the solvent in which the polymer is not soluble to further solidify the extruded polymer mixture and replace the solvent in which the polymer is soluble with a solvent that will more readily evaporate, thereby reducing the drying time. Solvent replacement baths can include a series of solvent replacement baths having a gradient of solvent in which the polymer is soluble with the solvent in which the polymer is not soluble, a series of solvent replacement baths having only the solvent in which the polymer is not soluble, or a single solvent replacement bath having only the solvent in which the polymer is not soluble.

Finished fibers are sometimes referred to as staple fibers, shortcut fibers, or pulp. In embodiments, finishing includes drying the extruded polymer mixture. In embodiments, finishing includes cutting or crimping the extruded polymer mixture to form individual fibers. Wet drawing of the extruded polymer mixture provides a substantially uniform diameter to the extruded polymer mixture and, thus, the fibers cut therefrom. Drawing is distinct from extruding, as is well known in the art. In particular, extruding refers to the act of making fibers by forcing the resin mixture through the spinneret head whereas drawing refers to mechanically pulling the fibers in the machine direction to promote polymer chain orientation and crystallinity for increased fiber strength and tenacity.

In embodiments wherein the fibers are prepared from a wet cooled gel spinning process, the fiber forming polymer can be generally any fiber forming polymer or blend thereof, e.g., two or more different polymers, as generally described herein. In refinements of the foregoing embodiment, the polymer(s) can have any degree of polymerization (DP), for example, in a range of 10 to 10,000,000, for example, at least 10, at least 20, at least 50, at least 100, at least 200, at least 300, at least 400, at least 500, at least 750, or at least 1000 and up to 10,000,000, up to 5,000,000, up to 2,500,00, up to 1,000,000, up to 900,000, up to 750,000, up to 500,000, up to 250,000, up to 100,000, up to 90,000, up to 75,000, up to 50,000, up to 25,000, up to 12,000, up to 10,000, up to 5,000, or up to 2,500, for example in a range of 1000 to about 50,000, 1000 to about 25,000, 1000 to about 12,000, 1000 to about 5,000, 1000 to about 2,500, about 50 to about 12,000, about 50 to about 10,000, about 50 to about 5,000, about 50 to about 2,500, about 50 to about 1000, about 50 to about 900, about 100 to about 800, about 150 to about 700, about 200 to about 600, or about 250 to about 500. In embodiments, the DP is at least 1,000. In embodiments, the fiber forming polymer comprises a polyvinyl alcohol polymer having a DP in a range of 1000 to about 50,000, 1000 to about 25,000, 1000 to about 12,000, 1000 to about 5,000, 1000 to about 2,500, about 50 to about 12,000, about 50 to about 10,000, about 50 to about 5,000, about 50 to about 2,500, about 50 to about 1000, about 50 to about 900, about 100 to about 800, about 150 to about 700, about 200 to about 600, or about 250 to about 500. In embodiments, the fiber forming polymer comprises a polyvinyl alcohol having a DP in a range of 1000 to about 50,000, 1000 to about 25,000, 1000 to about 12,000, 1000 to about 5,000, or 1000 to about 2,500.

The wet cooled gel spinning process advantageously provides one or more benefits such as providing a fiber that includes a blend of water-soluble polymers, providing control over the diameter of the fibers, providing relatively large diameter fibers, providing control over the length of the fibers, providing control over the tenacity of the fibers, providing high tenacity fibers, providing fibers from polymers having a large degree of polymerization, and/or providing fibers which can be used to provide a self-supporting nonwoven web. Continuous processes such as spun bond, melt blown, electro-spinning and rotary spinning generally do not allow for blending of water-soluble polymers (e.g., due to difficulties matching the melt index of various polymers), forming large diameter (e.g., greater than 50 micron) fibers, controlling the length of the fibers, providing high tenacity fibers, or the use of polymers having a high degree of polymerization. Further, the wet cooled gel spinning process advantageously is not limited to polymers that are only melt processable and, therefore, can access fibers made from fiber forming materials having very high molecular weights, high melting points, low melt flow index, or a combination thereof, providing fibers having stronger physical properties and different chemical functionalities compared to fibers prepared by a heat extrusion process.

Methods of preparing staple fibers and continuous fibers are well known in the art. Once the staple fibers or continuous fibers are carded, the nonwoven web is bonded. Methods of bonding staple fibers are well known in the art and can include through air bonding (thermal), calendar bonding (thermal with pressure), and chemical bonding. The nonwoven web of the disclosure can be thermally or chemically bonded. The nonwoven web can be generally porous with varying pore size, morphology and web heterogeneity. Fiber physical properties and the type of bonding can affect the porosity of the resulting nonwoven web. Calendar bonding is achieved by applying heat and pressure, and typically maintains the pore size, shape, and alignment produced by the carding process. The conditions for calendar bonding can be readily determined by one of ordinary skill in the art. In general, if the heat and/or pressure applied is too low, the fibers will not sufficiently bind to form a free-standing web and if the heat and/or pressure is too high, the fibers will begin to meld together. The fiber chemistry dictates the upper and lower limits of heat and/or pressure for calendar bonding. Without intending to be bound by theory, it is believed that at temperatures above 235° C., polyvinyl alcohol based fibers degrade. Methods of embossment for calendar bonding of fibers are known. The embossing can be a one-sided embossing or a double-sided embossing. Typically, embossing of water-soluble fibers includes one-sided embossing using a single embossing roll consisting of an ordered circular array and a steel roll with a plain surface. As embossing is increased (e.g., as surface features are imparted to the web), the surface area of the web is increased. Without intending to be bound by theory it is expected that as the surface are of the web is increased, the solubility of the web is increased. Accordingly, the solubility properties of the nonwoven web can be advantageously tuned by changing the surface area through embossing.

In contrast to calendar bonding, chemical bonding typically uses a binder solution of the waste polymer left over from preparing the fibers to coat the carded fibers under pressure, which can result in smaller, less ordered pores relative to the pores as carded. Generally, the solvent can be any solvent that solubilizes the binder. Typically, the solvent of the chemical bonding solution is water. Without intending to be bound by theory, it is believed that if the polymer solution used for chemical bonding is sufficiently concentrated and/or sufficient pressure is applied, a nonporous water-dispersible nonwoven web can be formed. The solvent used in chemical bonding induces partial solubilization of the existing fibers in the web to weld and bond the fibers together. The polyvinyl alcohol binder provided in the solution assists in the welding process to provide a more mechanically robust web. The temperature of the polymer solution is not particularly limited and can be provided at room temperature (about 23° C.).

In some embodiments, a second layer of fibers can be used to bond the nonwoven web. Without intending to be bound by theory, it is believed that fibers prepared from by a melt blown process, for example, water-soluble fibers, can be used to bond the nonwoven web using an in-line process. In particular, a nonwoven web can be passed under a melt blown process station such that the melt blown fibers are deposited after melt extrusion and as the melt blown fibers cool and solidify, they bond to each other and to the nonwoven web on which they are deposited. Melt blown fibers can be micro- to nano-scale in length and can be provided on the nonwoven web such that the melt blown fibers make up about 15%, about 12%, about 10%, about 8%, about 6%, or about 5%, by weight of the final nonwoven web, based on the total weight of the fibers in the final nonwoven web. Without intending to be bound by theory it is believed that the inclusion of about 5% to about 15% of melt blown fibers can increase the mechanical integrity of the nonwoven web, without substantially changing the solubility properties of the nonwoven web. In general, when a polyvinyl alcohol fiber forming material is used to prepare a melt blown fiber, the polyvinyl alcohol polymer will be a homopolymer as melt blown processes require low viscosity and high melt flow index polymers.

Pore sizes can be determined using high magnification and ordered surface analysis techniques including, but not limited to Brunauer-Emmett-Teller theory (BET), small angle X-ray scattering (SAXS), and molecular adsorption.

In general, the fibers of the disclosure can be formed by any fiber process known in the art and are then post-process treated by chemical modification, wherein the chemical modification does not include hydrolyzing the polymer.

The disclosure provides a method of treating a fiber including a polymer such as a polymer comprising at least one of a vinyl acetate moiety or a vinyl alcohol moiety, e.g., only at least one vinyl acetate moiety, only at least one vinyl alcohol moiety, or both a vinyl acetate moiety and a vinyl alcohol moiety, as described herein. In embodiments, the method includes contacting a surface of a fiber comprising a polymer comprising at least one of a vinyl acetate moiety or a vinyl alcohol moiety as described herein with a modification agent to chemically modify at least a portion of the polymer with the modification agent in a region of the fiber comprising at least a surface of the fiber so as to form a modified fiber. In embodiments, the method includes admixing a fiber comprising a polymer comprising at least one of a vinyl acetate moiety or a vinyl alcohol moiety as described herein, a modification agent, and optionally a solvent for the modification agent to chemically modify at least a portion of the polymer with the modification agent and form a modified fiber. In embodiments, the fiber is not soluble in the solvent for the modification agent. The degree of modification after contacting a surface of the fiber with a modification agent or after admixing with the modification agent and a solvent for the modification agent can be determined by any suitable method known to one of ordinary skill in the art, such as, attenuated total reflection (ATR), fourier transform infrared spectroscopy (FTIR), differential scanning calorimetry (DSC), solubility testing (e.g., the example Dissolution and Disintegration Test Method disclosed herein), titration (e.g., the example Titration Method disclosed herein), or the like or combinations thereof. The Titration Method determines an average degree of hydrolysis or chemical modification for a fiber. For a fiber characterized by a constant degree of hydrolysis or modification across a transverse cross-section of the fiber, the constant degree of hydrolysis or modification is the average degree of hydrolysis for the fiber. For a fiber characterized by a transverse cross-section of the fiber having a core-sheath or core-shell type distribution or a gradient distribution of the degree of hydrolysis or modification, the Titration test provides the average degree of hydrolysis or modification across all sections of the fiber. As used herein, and unless specified otherwise, at least a portion of a fiber has a decreased degree of hydrolysis if any portion of the fiber (e.g., an exterior surface or portion, a shell surface or portion, and/or an interior portion) has an increased degree of modification after admixing, relative to the degree of hydrolysis of the starting fiber. It will be understood that a decrease in degree of hydrolysis to any portion of the fiber will result in a decrease in the average degree of hydrolysis of the fiber as determined by the Titration Method. Thus, it will be understood that the degree of hydrolysis of at least a portion of the polyvinyl alcohol polymer in the fiber will have decreased if the average degree of hydrolysis of the fiber, as determined by the Titration Method, is less after admixing the fiber with the modification agent, relative to the average degree of hydrolysis of the fiber prior to admixing.

As used herein, and unless specified otherwise, at least a portion of a fiber has an increased degree of modification if any portion of the fiber (e.g., an exterior surface or portion, a sheath (shell) surface or portion, and/or an interior portion) has an decreased degree of hydrolysis after contacting or admixing, relative to the degree of modification of the starting fiber.

In general, contacting or admixing can include immersing the fibers in a mixture of the modification agent and a solvent for the modification agent. In embodiments, contacting or admixing can include immersing the fibers in a bi-phasic solvent system including the solvent for the modification agent and the modification agent. In embodiments, the bi-phasic solvent system can include water and an organic solvent. In embodiments, admixing can include stirring the mixture of the fibers, the modification agent, and the solvent for the modification agent. In embodiments, contacting can include applying an energy source such as a corona treatment, electron beam radiation, or UV radiation, to the fibers.

In embodiments, the method comprises admixing the modification agent and the fiber under conditions sufficient to provide a controlled amount of chemical modification (degree of modification) to the polymer and/or a controlled increase of chemical modification (degree of modification) to the polymer. In embodiments, the method further comprises admixing a solvent for the modification agent with the modification agent and the fiber. In embodiments, the method comprises admixing the modification agent, the fiber, and the modification agent solvent under conditions sufficient to provide a controlled amount of chemical modification (degree of modification) to the polymer and/or a controlled increase of chemical modification (degree of modification) to the polymer. In embodiments, the method further comprises admixing a solvent for the modification agent with the modification agent and the fiber. In general, the amount of chemical modification of the treated fiber and/or the increase of the chemical modification of the treated fiber can be designed and controlled by varying the reaction conditions. Reaction conditions that can be modified to provide a controlled amount of chemical modification and/or increase in chemical modification include the selection of the modification agent, selection of the solvent for the modification agent, selection of the concentration of the modification agent in the solvent, reaction (admixing or contacting) time, reaction (admixing or contacting) temperature, and optional inclusion of an activator.

In general, as the reaction time increases, the chemical modification will increase. Thus, the reaction time can be selected to provide a desired increase in the chemical modification of the polymer that makes up the fiber, e.g., polyvinyl alcohol, a copolymer of vinyl acetate and vinyl alcohol, or an anionically modified vinyl alcohol copolymer. The reaction time can be up to about 48 hours, for example, about 1 minutes to about 36 hours, about 2 minutes to about 24 hours, about 2 minutes to about 12 hours, about 2 minutes to about 6 hours, about 2 minutes to about 4 hours, about 2 minutes to about 2 hours, about 2 minutes to about 1 hour, about 5 minutes to about 1 hour, about 5 minutes to about 2 hours, about 5 minutes to about 5 hours, about 5 minutes to about 10 hours, about 5 minutes to about 12 hours, about 5 minutes to about 24 hours, about 10 minutes to about 24 hours, about 15 minutes to about 24 hours, about 30 minutes to about 24 hours, about 1 hour to about 24 hours, about 2 hours to about 24 hours, about 3 hours to about 24 hours, about 4 hours to about 24 hours, about 5 hours to about 24 hours, about 6 hours to about 24 hours, about 8 hours to about 24 hours, about 10 hours to about 24 hours, about 12 hours to about 24 hours, about 12 hours to about 18 hours, about 14 hours to about 20 hours, or about 16 hours to about 24 hours. In embodiments, the admixing can be for about 1 minutes to about 48 hours. In embodiments, the admixing can be for about 1 hour to about 36 hours. In embodiments, the admixing can be for about 2 hours to about 8 hours.

In general, as the temperature of the reaction is increased, the rate of chemical modification will increase. Thus, the temperature of the reaction can be selected in combination with reaction time to provide a desired increase in the amount of chemical modification of the polymer that makes up the fiber, e.g., polyvinyl alcohol, a copolymer of vinyl acetate and vinyl alcohol, or an anionically modified vinyl alcohol copolymer. The temperature of the reaction is not particularly limited so long as the fiber does not dissolve or decompose and the solvent, if present, remains a liquid under the heating conditions. The reaction temperature can be from about 10° C. to about 200° C., about 10° C. to about 190° C., about 10° C. to about 180° C., about 10° C. to about 170° C., about 10° C. to about 160° C., about 10° C. to about 150° C., about 10° C. to about 140° C., about 10° C. to about 130° C., about 10° C. to about 120° C., about 10° C. to about 110° C., about 10° C. to about 100° C., about 10° C. to about 90° C., about 10° C. to about 80° C., about 10° C. to about 70° C., about 10° C. to about 60° C., about 10° C. to about 50° C., about 10° C. to about 40° C., about 10° C. to about 30° C., about 20° C. to about 100° C., about 20° C. to about 90° C., about 20° C. to about 80° C., about 30° C. to about 100° C., about 30° C. to about 90° C., about 30° C. to about 80° C., about 40° C. to about 80° C., about 50° C. to about 80° C., or about 60° C. to about 80° C. Without intending to be bound by theory, it is believed that at higher temperatures as the polarity of the solvent increases the fibers may begin to swell, gel, and/or dissolve. Accordingly, the temperature of the reaction can be selected in combination with the solvent such that the fiber will remain insoluble and will not decompose. In embodiments, the method further comprises heating the fiber in a solvent for the modification agent prior to admixing the modification agent with the fiber and solvent. In embodiments, the method further comprises heating a mixture of the fiber, the modification agent, and the solvent for the modification agent.

The selection of the modification agent can affect the rate of the modification reaction. Thus, the modification agent can be selected in combination with the reaction time and temperature to provide a desired increase in the amount of chemical modification of the polymer that makes up the fiber, e.g., polyvinyl alcohol, a copolymer of vinyl acetate and vinyl alcohol, or an anionically modified vinyl alcohol copolymer. In embodiments wherein the modification occurs by acid or base catalyzed transesterification of an ester or amide, the rate of the reaction can be modified based on the nucleophilic strength of the modification agent.

The chemical modification can generally be any desired chemical modification of a functional group on the polymer backbone of a fiber to a desired functional group. Non-limiting examples of contemplated chemical modifications include one or more of an esterification, amidation, amination, carboxylation, nitration, acyloin condensation, allylation, acetylaction, imidization, halogenation, sulfonation, alkylation, acetalyzation, enolyzation, nitrosation, silane coupling, and crosslinking. In embodiments, the methods can comprise admixing under conditions sufficient to chemically modify the polymer comprising at least one of a vinyl acetate moiety or vinyl alcohol moiety, e.g., only at least one vinyl acetate moiety, only at least one vinyl alcohol moiety, or both a vinyl acetate moiety and a vinyl alcohol moiety, wherein the chemical modification comprises one or more of an esterification, amidation, amination, carboxylation, nitration, acyloin condensation, allylation, acetylaction, imidization, halogenation, sulfonation, alkylation, acetalyzation, enolyzation, nitrosation, and silane coupling. In embodiments, the methods can comprising contacting under conditions sufficient to crosslink the polymers, wherein the modification agent comprises a corona treatment, electron beam radiation, or UV radiation. In some embodiments, the polymer after chemical modification is not crosslinked.

The modification agent can generally be any agent that can chemically modify a functional group on the polymer backbone to the desired functional group, and/or catalyze same. Non-limiting examples of modification agents include, but are not limited to, an anhydride, a carboxylic acid, an alcohol, an ester, an ether, a sulfonic acid, a sulfonate, a click chemistry reagent, an amide, an amine, a lactam, a nitrile, a ketone, an allyl compound, an acetyl compound, a halogen compound, an alkyl containing compound, an imide, an acetal containing compound, an enolate, a nitro containing compound, a silane, an aziridine, an isocyanate, or any combination thereof. In embodiments, the modification agent comprises an anhydride, a carboxylic acid, an alcohol, an ester, an ether, a sulfonic acid, a sulfonate, a click chemistry reagent, an amide, an amine, a nitrile, a ketone, an allyl compound, an acetyl containing compound, a halogen containing compound, an alkyl containing compound, an imide, an acetal containing compound, an enolate, a nitro containing compound, a silane, an aziridine, an isocyanate, an energy source, or any combination thereof. In embodiments, the modification agent comprises an anhydride, an amine, a sulfonate, a sulfonic acid, a monocarboxylic acid, a dicarboxylic acid, or any combination thereof. In embodiments, the modification agent comprises a sulfonate. In embodiments, the sulfonate comprises aminopropyl sulfonate. In embodiments, the modification comprises an amine or lactam. In embodiments, the lactam comprises a pyrrolidone or a caprolactam. In embodiments, the modification agent comprises a sulfonic acid. In embodiments, the sulfonic acid comprises 2-acrylamido-2-methylpropanesulfonic acid (AMPS). In embodiments, the modification agent comprises a monocarboxylic acid or dicarboxylic acid. In embodiments, the monocarboxylic acid or dicarboxylic acid comprises acetic acid, maleic acid, monoalkyl maleate, dialkyl maleate, fumaric acid, monoalkyl fumarate, dialkyl fumarate, itaconic acid, monoalkyl itaconate, dialkyl itaconate, citraconic acid, monoalkyl citraconate, dialkyl citraconate, mesaconic acid, monoalkyl mesaconate, dialkyl mesaconate, glutaconic acid, monoalkyl glutaconate, dialkyl glutaconate, alkyl (alkyl)acrylates, alkali metal salts of the foregoing, hydrolyzed alkali metal salts thereof, esters thereof, or combinations thereof. In embodiments, the modification agent comprises an anhydride. In embodiments, the anhydride is an organic acid anhydride and the organic acid anhydride comprises acetic anhydride, propionic anhydride, isobutyric anhydride, maleic anhydride, phthalic anhydride, glutaric anhydride, itaconic anhydride, citraconic anhydride, glutaconic anhydride, or any combination thereof. In embodiments, the organic acid anhydride comprises maleic anhydride. In embodiments, the modification agent comprises an aziridine. In embodiments, the aziridine is an oligomer. In embodiments, the modification agent comprises an isocyanate. In embodiments, the isocyanate is an oligomer. In some embodiments, the starting fiber comprises a copolymer of vinyl acetate and vinyl alcohol, and the modification agent comprises an organic acid anhydride. The hydroxyl group (—OH) from the vinyl alcohol moieties reacts with the modification agent and chemically bonds and attaches the modification moiety onto the polymer chain. In certain instances, the degree of modification is the same as (equal to) the degree of hydrolysis of the polymer before modification when the hydroxyl group is fully reacted.

As used herein, the term "click chemistry reagent" refers to a reagent that can chemically modify a polymer backbone of a fiber to a first functional group of a click chemistry reactive pair. As used herein, the term "click chemistry reactive pair" refers to a pair of complementary functional groups that is capable of undergoing a "click chemistry" reaction. As used herein, "first functional group of a click chemistry reactive pair" refers to one of the pair of complementary functional groups that is capable of undergoing a "click chemistry" reaction. In general, there are four main classes of click chemistry reactions: 1) cycloadditions, 2) nucleophilic ring-openings, 3) carbonyl chemistry of the non-aldol type, and 4) additions to carbon-carbon multiple bonds. The click chemistry reactive pair can be a pair of complementary functional groups that are compatible with the four classes of click chemistry reactions shown above, such as thiol/alkene, azide/alkynes, azide/alkene, alkene/tetrazine, isonitrile/tetrazine, etc. Further examples of click chemistry reactive pairs can be found in Wang et. al., *Pharm Res.*, 2008, 25(10): 2216-2230; Bowman et al., *Adv. Funct. Mater.*, 2014, 24, 2572-2590; and Jozwiak et al., *Chem. Rev.*, 2013, 113, 4905-4979.

In general, as the concentration of modification agent in the solvent for the modification agent increases, the rate of reaction will increase. Thus, the concentration of the modification agent can be selected in combination with the reaction time, reaction temperature, and selection of the modification agent to provide a desired increase in the degree of modification of the polymer that makes up the fiber, e.g., polyvinyl alcohol, a polyvinyl alcohol copolymer, or a modified polyvinyl alcohol copolymer. In general, the concentration of the modification agent in the solvent for the modification agent can be any concentration. Typically, the concentration will be selected such that all of the modification agent provided is in solution. In embodiments, the modification agent can be provided in an amount of about 0.2% to about 75% (w/w) based on the weight of the solvent, for example, about 0.2% to about 75%, about 0.2% to about 50%, about 0.2% to about 25%, about 0.5% to about 20%, about 1% to about 18%, about 2% to about 16%, about 5% to about 15%, about 8% to about 12%, or about 10%. In embodiments, the modification agent is provided in an amount of about 0.2% to about 25% (w/w), based on the weight of the solvent. In embodiments, the modification agent is provided in an amount of about 2% to about 25% (w/w), based on the weight of the solvent. In embodiments, the modification agent is provided in an amount of about 5% to about 15% (w/w), based on the weight of the solvent. In embodiments wherein the modification agent is an energy source, in general, as the intensity of the energy source increases, the rate of reaction will increase. Thus, the energy intensity can be selected in combination with reaction time, reaction temperature, and selection of the modification agent to provide a desired increase in the degree of modification of the polymer that makes up the fiber, e.g., polyvinyl alcohol.

The solvent for the modification agent can generally be any solvent in which the modification agent is soluble and the fiber to be treated is insoluble at the temperature at which the treatment takes place for the duration of contact of the fiber with the solvent. In embodiments, the fiber is insoluble in the solvent prior to treatment. In embodiments, the fiber is insoluble in the solvent during treatment. In embodiments, the fiber is insoluble in the solvent after treatment. In general, the solvent can be selected in combination with the reaction time, reaction temperature, selection of the modification agent and concentration thereof to provide a desired increase in the degree of modification of the polymer that makes up the fiber, e.g., polyvinyl alcohol. As the polarity of the solvent increases, the diffusion of the solvent into the polymer matrix of the fiber generally increases, resulting in an increase in the diffusion of the modification agent into the polymer matrix. Without intending to be bound by theory, it is believed that as the polarity of the solvent increases, the degree of modification of the inner/core section of the fiber can increase, such that the degree of modification can be increased across a transverse cross-section of the fiber. Further, without intending to be bound by theory, as the polarity of the solvent decrease, the diffusion of the solvent into the polymer matrix of the fiber generally decreases, such that the degree of modification can be increased at a portion of the surface, exterior, or sheath of the fiber. Modification of the polymer of the fiber at a portion of the surface, exterior, or sheath of the fiber also results in an average increase in the degree of modification across a transverse cross-section of the fiber. Further, without intending to be bound by theory, a combination of solvents can be used to provide a diffusion controlled radiant gradient of the degree of modification of the polymers of the treated fiber. In embodiments, the combination of solvents can be a bi-phasic solvent system. In embodiments, the bi-phasic solvent system can comprise water and an organic solvent. In embodiments, the bi-phasic solvent system can comprise water and an alcohol (e.g., methanol, ethanol, isopropanol, butanol, pentanol). In embodiments, the bi-phasic solvent system comprises water and methanol.

In embodiments, the solvent for the modification agent solution can be characterized by the Hansen Solubility Parameter (HSP). Without intending to be bound by theory, it is believed that the three HSP values, dispersion, molar volume, and hydrogen-bonding, are indicators of miscibility and, thus, solvation or swelling of polyvinyl alcohol by a particular solvent. Further, without intending to be bound by theory, it is believed that while hydrogen bonding is the largest predictor of expected behavior, the summation of all the parameters, $H_{total}$, is also predictive. In general, when the HSP values of the solvent are less than the HSP values of the polyvinyl alcohol, the more dissimilar the HSP values are between the solvent and the polyvinyl alcohol, the lower the diffusivity of the solvent into the polyvinyl alcohol. Without intending to be bound by theory, it is believed that when the $H_{total}$ value of the solvent is about 4 to about 15 units lower than the $H_{total}$ value of the polyvinyl alcohol, the rate of solvent uptake and diffusivity of the solvent into the polyvinyl alcohol is such that a gradient of solvent uptake and, thus, modification agent uptake, will occur, providing a gradient in the degree of modification of the polyvinyl alcohol fiber across a transverse cross section with a higher degree of modification at a surface region, relative to an inner, core region. Without intending to be bound by theory, it is believed that when the $H_{total}$ value of the solvent is about 4 to about 15 units higher than the $H_{total}$ value of the polyvinyl alcohol, the rate of solvent uptake and diffusivity of the solvent into the polyvinyl alcohol is such that solvent uptake and, thus, modification agent uptake, will occur quickly providing a uniform degree of modification across a transverse cross-section of the polyvinyl alcohol fiber. Further, without intending to be bound by theory, it is believed that when the $H_{total}$ value of the solvent is more than 15 units lower than that of the polyvinyl alcohol of the fiber the diffusivity will be limited such that only an outer surface of the fiber will be treated with the modification agent and when the $H_{total}$ value of the solvent is more than 15 units higher than that of the polyvinyl alcohol of the fiber, the solvent will dissolve the polyvinyl alcohol of the fiber.

In embodiments, the solvent for the modification agent comprises a polar solvent. In embodiments, the solvent comprises octanol, heptanol, hexanol, pentanol, butanol, propanol, tetrahydrofuran, dichloromethane, acetone, ethanol, N-methylpyrrolidone, methanol, acetonitrile, ethylene glycol, N,N-dimethylformamide, glycerol, dimethyl sulfoxide, formic acid, water, or any combination thereof. In embodiments, the solvent comprises n-octanol, n-heptanol, n-hexanol, n-pentanol, n-butanol, isobutanol, sec-butanol, tert-butanol, n-propanol, isopropanol, acetone, ethanol, N-methylpyrrolidone, methanol, acetonitrile, N,N-dimethylformamide, dimethyl sulfoxide, formic acid, water, or any combination thereof. In embodiments, the solvent comprises n-propanol, acetone, ethanol, N-methylpyrrolidone, methanol, acetonitrile, N,N-dimethylformamide, dimethyl sulfoxide, formic acid, water, or any combination thereof. In embodiments, the solvent comprises one or more solvents selected from the group consisting of methanol, ethanol, n-propanol, isopropanol, acetone, N-methylpyrrolidone, acetonitrile, N,N-dimethylformamide, dimethyl sulfoxide, formic acid, water, and any combination thereof. In embodiments, the solvent comprises an alcohol that is a liquid under the admixing conditions. In embodiments, the solvent comprises methanol. In embodiments, the solvent comprises methanol and at least one additional solvent. In embodiments, the solvent comprises methanol and water. In embodiments, the solvent comprises at least one of butanol, pentanol, hexanol, heptanol, and octanol in combination with water. In embodiments, the solvent comprises a mixture of a first solvent and a second solvent. In embodiments, the first solvent comprises water and the second solvent comprises an alcohol. In embodiments, the second solvent comprises methanol, ethanol, n-propanol, isopropanol, or any combination thereof. In embodiments, the solvent comprises DMSO and water. In embodiments, the solvent comprises DMSO and water and the DMSO and water are provided in a weight ratio of about 40/60 to 80/20. Without intending to be bound by theory, it is believed that as the amount of water increases above 60% or the amount of DMSO increases above about 80%, the interaction of the respective solvents with polyvinyl alcohol increases, resulting in increased swelling and gelling of the polymer.

In embodiments, the solvent comprises a nonpolar solvent. In embodiments, the solvent comprises hexanes, cyclohexane, methylpentane, pentane, cyclopropane, dioxane, benzene, pyridine, xylene, toluene, diethyl ether, chloroform, or any combination thereof.

In embodiments, the solvent comprises a mixture of a first solvent and a second solvent. In embodiments, the first solvent comprises a polar solvent and the second solvent comprises a nonpolar solvent. In embodiments, the first solvent has a first dielectric constant and the second solvent has a second dielectric constant and the dielectric constant of the first solvent is higher than the dielectric constant of the second solvent. In embodiments, the first dielectric constant is 5 or less, 4 or less, 3 or less, or 2 or less. In embodiments, the second dielectric constant is greater than 5, greater than 7.5, greater than 10, greater than 15, greater than 18, greater than 20, greater than 25, or greater than 30. In embodiments, the difference between the first dielectric constant and the second dielectric constant is at least 3, at least 5, at least 8, or at least 10. In embodiments, wherein the solvent comprises a mixture of a first solvent and a second solvent, the first solvent and the second solvent can be provided in any ratio provided that the hydrolysis agent is soluble in the mixture and the fiber is not soluble in the mixture prior to treatment, during treatment, and after treatment. In embodiments, the first solvent and second solvent can be provided in a weight ratio of about 99/1 to about 1/99, about 95/5 to about 5/95, about 90/10 to 10/90, about 85/15 to about 15/85, about 80/20 to about 20/80, about 75/25 to about 25/75, about 70/30 to about 30/70, about 65/35 to about 35/65, about 60/40 to about 40/60, about 55/45 to about 45/55, or about 50/50.

In embodiments, the methods of the disclosure further include admixing the fiber, the modification agent, and the optional solvent with an activator. The activator can generally be any additive that facilitates the treatment of the fiber by the modification agent. The activator can generally include a catalyst for reducing the activation energy of the reaction between the polymer of the fiber and the modification agent or a compound that facilitates diffusion of the modification agent into the polymer matrix, for example. In embodiments, the activator can comprise an acid, a base, an aziridine, a free radical initiator, or a combination thereof. In embodiments, the activator is a free radical initiator. In embodiments, the free radical initiator can comprise a peroxide. In embodiments, the peroxide can comprise benzoic peroxide, hydrogen peroxide, dibenzoyl peroxide (BPO), didodecanoyl (dilauroyl) peroxide (LPO), or a combination thereof. In embodiments, the free radical initiator can comprise an azo compound, such as, 2,2'-Azobisisobutyronitrile (AIBN). In embodiments, the activator is an acid. In embodiments, the acid can comprise an organic acid, inorganic acid, or a combination thereof. In embodiments, the organic acid can comprise carboxylic acids such as formic acid, acetic acid, oxalic acid, malonic acid, or a combination thereof. In embodiments, the inorganic acid can comprise boric acid, nitric acid, nitrous acid, phosphoric acid, phosphorous acid, sulfuric acid, hydrosulfuric acid, chloric acid, chlorous acid, hypochlorous acid, a hydrohalic acid, or a combination thereof. In embodiments, the hydrohalic acid can comprise hydrofluoric acid, hydrochloric acid, hydrobromic acid, hydroiodic acid, or a combination thereof. In embodiments, the activator is a base. In embodiments, the base can comprise a metallic hydroxide. In embodiments, the metallic hydroxide can comprise lithium hydroxide, sodium hydroxide, potassium hydroxide, rubidium hydroxide, caesium hydroxide, or a combination thereof.

The modified fiber can generally be a fiber that includes a chemical modification after admixing with the modification agent. Non-limiting examples of chemical modifications that the modified fiber can comprise, includes a monocarboxylic acid, a dicarboxylic acid, a sulfonic acid, a sulfonate, a first functional group of a click chemistry reactive pair, an amide, an amine, a carbamate, a nitrile, a ketone, an ester, an allyl, an acetyl, a halogen, an alkyl, an imide, an acetal, an enolate, a nitro, a silane, a crosslink, or any combination thereof. In embodiments, the modified fiber comprises a monocarboxylic acid, a dicarboxylic acid, a sulfonic acid, a sulfonate, a first functional group of a click chemistry reactive pair, an amide, an amine, a nitrile, a ketone, an ester, an allyl, an acetyl, a halogen, an alkyl, an imide, an acetal, an enolate, a nitro, a silane or a combination thereof. In embodiments, the modified fiber comprises a sulfonate, a sulfonic acid, or both. In embodiments, the modified fiber comprises vinyl sulfonic acid, allyl sulfonic acid, ethylene sulfonic acid, 2-acrylamido-1-methylpropanesulfonic acid, 2-acrylamido-2-methylpropanesufonic acid, 2-methacrylamido-2-methylpropanesulfonic acid, 2-sulfoethyl acrylate, alkali metal salt derivatives of the foregoing, or combinations thereof. In embodiments, the modified fiber comprises a sulfonate. In embodiments, the sulfonate comprises aminopropyl sulfonate. In embodiments, the modified fiber comprises a sulfonic acid. In embodiments, the sulfonic acid comprises 2-acrylamido-2-methylpropanesulfonic acid (AMPS) and/or the sodium salt of AMPS. In embodiments, the modified fiber comprises an amine or a carbamate as a moiety from a lactam. In embodiments, such a carbamate can be from a lactam comprising a pyrrolidone or a caprolactam. In embodiments, the modified fiber comprises a monocarboxylic acid or dicarboxylic acid. In embodiments, the monocarboxylic acid or dicarboxylic acid comprise acetic acid, maleic acid, monoalkyl maleate, dialkyl maleate, fumaric acid, monoalkyl fumarate, dialkyl fumarate, itaconic acid, monoalkyl itaconate, dialkyl itaconate, citraconic acid, monoalkyl citraconate, dialkyl citraconate, mesaconic acid, monoalkyl mesaconate, dialkyl mesaconate, glutaconic acid, monoalkyl glutaconate, dialkyl glutaconate, alkyl (alkyl)acrylates, alkali metal salts of the foregoing, hydrolyzed alkali metal salts thereof, esters thereof, or combinations thereof. In embodiments, the dicarboxylic acid comprises a monomethyl maleate. In embodiments, the modified fiber comprises a first functional group of a click chemistry reactive pair as disclosed above. In embodiments, the modified fiber comprises a first functional group of a click chemistry reactive pair and an active agent as disclosed herein comprises a second functional group of the click chemistry reactive pair. Thus, a modification agent can be contemplated to modify a fiber with a particular first functional group of a click chemistry reactive pair, such that the desired active agent comprising the second functional group of the click chemistry reactive pair can be readily reacted with the modified fiber to form a fiber bonded to the desired active agent. In embodiments, the modified fiber comprises an amide. In embodiments, the modified fiber comprises an ester. In embodiments, the modified fiber comprises an amine.

In general, an increase in the amount of chemical modification (degree of modification) of the modified fiber, relative to the fiber prior to the post-processing methods disclosed herein, can be in a range of 0.1 mol % to about 50 mol %. For example, the degree of modification from the methods disclosed herein can be about 1 mol %, about 2 mol %, about 3 mol %, about 4 mol %, about 5 mol %, about 6 mol %, about 7 mol %, about 8 mol %, about 9 mol %, about 10 mol %, about 11 mol %, about 12 mol %, about 13 mol %, about 14 mol %, about 15 mol %, about 20 mol %, about 30 mol %, about 40 mol % or about 50 mol %, such as, in a range of 1 mol % to 15 mol %, about 1 mol % to about 10 mol %, about 1 mol % to about 8 mol %, about 2 mol % to about 8 mol %, about 2 mol % to about 8 mol %, about 3 mol % to about 8 mol %, about 3 mol % to about 6 mol %, or about 1 mol % to about 4 mol %.

Figure 2C:
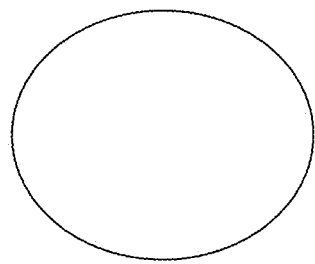
FIG. 2C shows a transverse cross-section of a round fiber characterized by the polymer having the same or equal degree of modification across the transverse cross-section, according to example embodiments.
Figure 2B:
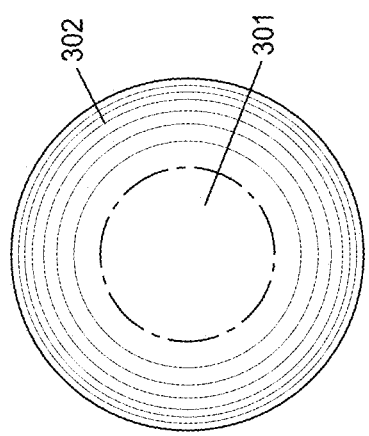
FIG. 2B shows a transverse cross-section of a round fiber characterized by an increasing gradient in the degree of modification of the polymer from an interior region 301 to a surface region 302, according to example embodiments.
Figure 2A:
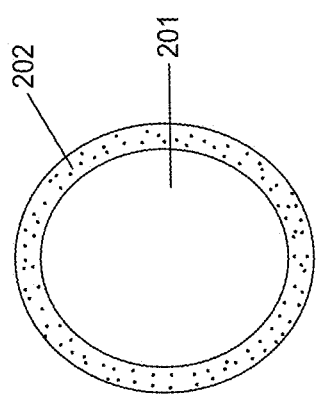
FIG. 2A shows a transverse cross-section of a round fiber characterized by a core-sheath structure, wherein the polymer of the sheath (shell) 202 has chemical modification or a higher degree of modification than the polymer of the core 201, according to example embodiments.
Figure 3:
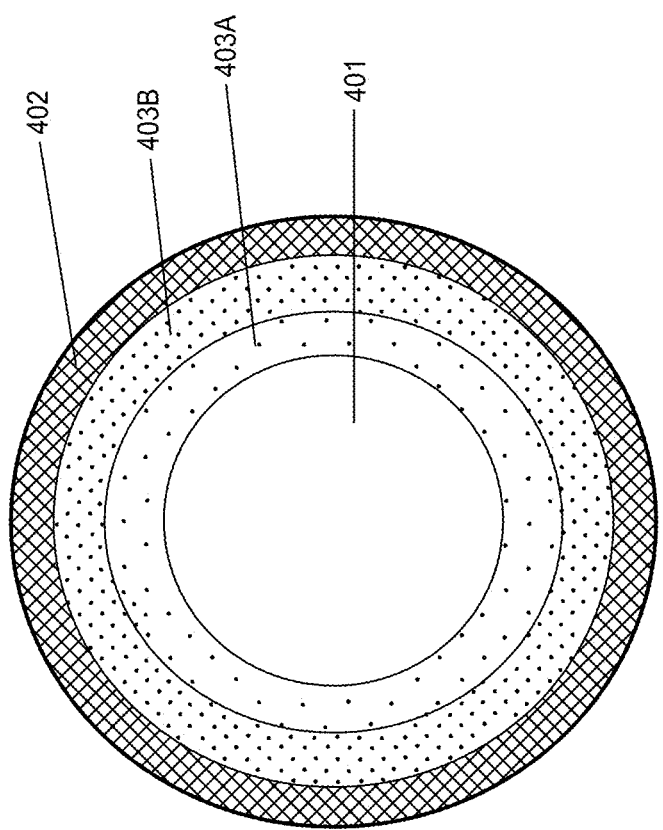
FIG. 3 shows a transverse cross-section of a round fiber having a first region, e.g., core region, 401, a second region, e.g., a sheath (shell) region 402, and at least one third region, e.g., two intermediate regions 403a and 403b, disposed between the first region and the second region, the cross section of the fiber characterized by an increasing gradient in the degree of modification of the polymer from the first region to the second region, according to example embodiments.

The reaction conditions can also be selected to design and control the solubility mechanism and/or absorption capacity and retention of the treated fiber. For example, the reaction conditions can be selected to provide a fiber having a transverse cross-section characterized by: (a) a core-sheath structure, wherein the polymer of the sheath has a different, e.g., greater, degree of modification than the polymer of the core (FIG. 2A), (b) a radial gradient in the degree of modification of the polymer, for example, in an order of increasing degree of modification, from an interior region to a surface region (FIG. 2B; FIG. 3), or (c) a consistent degree of modification across the transverse cross-section (FIG. 2C). The resulting fibers can have different solubility mechanisms (for example, immediate release, delayed release, or triggered release), chemical compatability/resistance, and/or absorption capacity and retention properties. Reaction conditions that can be modified to provide a controlled fiber structure include the selection of the modification agent, selection of the concentration of the modification agent in the solvent for the modification agent, reaction (contacting or admixing) time, reaction (contacting or admixing) temperature, selection of solvent for the modification agent, and optional inclusion of an activator.

A fiber having a core-sheath structure or core-shell structure can be prepared by treating a fiber having a polymer such as polyvinyl alcohol with a modification agent and a solvent under conditions sufficient to minimize the radial diffusion of the solvent and the modification agent into an inner core region of the fiber. Diffusion of the solvent and modification agent into an inner core region of the fiber can be minimized, for example, by selecting a short reaction time, a low reaction temperature, and/or including a nonpolar solvent. In embodiments, the contacting of the methods of the disclosure is performed under conditions sufficient to provide a fiber comprising a polymer having vinyl alcohol moieties having a transverse cross-section characterized by a core-sheath structure, wherein the polymer of the sheath has a greater degree of modification than the polymer of the core. In embodiments, the conditions sufficient to provide a fiber having a transverse cross-section characterized by a core/sheath structure, wherein the polymer of the sheath has a greater degree of modification than the polymer of the core comprises including a solvent having a dielectric constant of 20 or less, 18 or less, 14 or less, or 10 or less. In embodiments, the conditions sufficient to provide a fiber having a transverse cross-section characterized by a core-sheath structure, wherein the polymer of the sheath has a greater degree of modification than the of the core comprises admixing the fiber and the modification agent solution at a temperature in a range of about 10° C. to about 30° C., about 10° C. to about 25° C., or about 15° C. to about 25° C. In embodiments, the conditions sufficient to provide a fiber having a transverse cross-section characterized by a core-sheath structure, wherein the polymer of the sheath has a greater degree of modification than the polymer of the core comprises admixing the fiber and the modification agent for a time of about 2 minutes to about 6 hours, about 2 minutes to about 4 hours, about 5 minutes to about 3 hours, about 10 minutes to about 2 hours, or about 15 minutes to about 1 hour. In embodiments, the conditions sufficient to provide a fiber having a transverse cross-section characterized by a core-sheath structure, wherein the polymer of the sheath has a greater degree of modification than the polymer of the core comprises including a solvent having a dielectric constant of 20 or less, 18 or less, 14 or less, or 10 or less, admixing the fiber, the modification agent, and the solvent at a temperature in a range of about 10° C. to about 30° C., about 10° C. to about 25° C., or about 15° C. to about 25° C., and admixing the fiber, the modification agent, and the solvent for a time of about 2 minutes to about 6 hours, about 2 minutes to about 4 hours, about 5 minutes to about 3 hours, about 10 minutes to about 2 hours, or about 15 minutes to about 1 hour. Such fibers having a transverse cross-section characterized by a core-sheath structure wherein the polymer of the sheath has a greater degree of modification than the polymer of the core can provide delayed release properties of an active agent provided in the interior of the fiber, controlled release properties of an active agent conjugated to the modified polymer, triggered release of an active agent provided in the interior of the fiber and/or conjugated to the modified polymer, and/or enhanced chemical resistance relative to a fiber having no modification. In embodiments, the modified sheath region can be substantially continuous. As used herein and unless specified otherwise, "substantially continuous" refers to a homogeneous distribution of modifications across the surface area of the fiber such that at least about 60% of the surface area of the fiber comprises a modification. In embodiments, at least about 75%, at least about 80%, at least about 90%, or at least about 95% of the surface area of the fiber comprises a modification. Without intending to be bound by theory, it is believed that when the modified sheath region is substantially continuous, the fiber can demonstrate enhanced chemical resistance when in contact with harsh chemicals such as oxidizing agents, such that the fiber is protected from discoloration and reduced solubility. Further, without intending to be bound by theory, it is believed that areas of discontinuation of the modified sheath region are areas susceptible to harsh chemical that allow infiltration of the harsh chemical and deterioration of the fiber by the harsh chemical over time, when the fiber is in contact with the harsh chemical.

As used herein and unless specified otherwise, "delayed release" of an active agent from a fiber means that the entirety of the active agent is not immediately released from the fiber when contacted with a solvent (usually water) under the conditions of an end use application of the fiber. For example, a fiber containing an active agent and used in a laundry application may not immediately release the entirety of the active under wash conditions. Rather, the active can diffuse from the fiber over time. As used herein and unless specified otherwise, "triggered release" of an active agent from a fiber means that none of the active is released from the fiber until a trigger condition is met. For example, a fiber containing an active agent and used in a laundry application may not release the active agent until the wash water reaches a predetermined temperature and/or pH.

Trigger conditions can include, but are not limited to, temperature, pH, UV/VIS radiation, IR radiation, presence of ions, presence of catalysts, or a combination thereof.

As the thickness of the sheath structure increases, the stability of a fiber having a core swollen and saturated with a fluid increases but the amount of polymer available in the core for absorbing a fluid decreases. The thickness of the sheath can be controlled by controlling the diffusion of the modification agent into the polymer structure of the fiber. It will be understood that because treatment of the inner portions of the fiber is diffusion controlled, the sheath may have a variation in thickness around a perimeter of the fiber and the inner portion of the sheath may have a degree of modification that is less than the degree of modification of the polymer at the exterior surface of the sheath but greater than the degree of modification of the polymer at the center of the fiber. Thus in some embodiments, the transverse cross-section of the fiber can be characterized by a core/sheath structure and can also be characterized as having an increasing gradient from an inner portion of the fiber to an exterior portion of the fiber.

A fiber having a transverse cross-section characterized by an increasing radial gradient structure can be prepared by treating a fiber having a polymer such as polyvinyl alcohol or copolymer of vinyl acetate and vinyl alcohol having no degree of modification with a modification agent and a solvent under conditions sufficient to modify the radial diffusion of the solvent and the modification agent into an inner region of the fiber. In embodiments, a fiber having a transverse cross-section characterized by an increasing radial gradient structure from an inner region to an exterior region can be prepared using multiple solvents having different rates of diffusion (concurrently or step-wise), changing the temperature during admixing to modify the rate of diffusion of the solvent and modification agent into the fiber, and/or selecting the reaction time such that it is long enough to allow some modification agent diffuses into the inner region to modify the degree of modification of the polymer but is not so long as to allow the polymer of the inner portion to be chemically modified to the same extent as the polymer of the exterior/surface portion. In embodiments, the admixing of the methods of the disclosure is performed under conditions sufficient to provide a fiber having a transverse cross-section characterized by an increasing gradient in the degree of modification of the polymer from an interior region of the fiber to a surface region of the fiber. Such fibers having a transverse cross-section characterized by an increasing gradient of degree of modification can provide delayed release properties of an active agent provided in the interior of the fiber, triggered release of an active agent provided in the interior of the fiber, increased absorbance relative to a fiber having a consistent degree of modification across a transverse cross-section, and/or improved retention of absorbed fluids.

Fibers having a transverse cross-section characterized by a core/sheath structure and/or an increasing radial structure can have active agents loaded in the core/inner regions. Actives can be loaded to the core/inner regions by contacting a fiber with a solution of an active agent and allowing the active agent solution to diffuse into the polymer structure, resulting in the core/inner regions of the fiber to absorb the active agent solution and swell. The active agent can be any active agent disclosed herein that is soluble in the active agent solution solvent. The solvent can be any solvent disclosed herein. Without intending to be bound by theory, it is believed that as the polarity of the solvent increases, the rate of diffusion to the core/inner regions of the fiber increases. An exemplary solvent is water provided that the water of the active agent solution is maintained at a temperature below the solubility temperature of the polymer that makes up the core/inner region of the fiber and the sheath/exterior region of the fiber.

A fiber having a transverse cross-section characterized by the polymer having the same degree of modification across (throughout) the transverse cross-section can be prepared by treating a fiber having a polymer such as polyvinyl alcohol or a polyvinyl alcohol copolymer with a modification agent and a solvent under conditions sufficient to maximize the radial diffusion of the solvent and the modification agent into an inner core region of the fiber. Diffusion of the solvent and modification agent into an inner core region of the fiber can be maximized, for example, by selecting a long reaction time, a high reaction temperature, and/or including a highly polar solvent. In embodiments, the admixing of the methods of the disclosure is performed under conditions sufficient to provide a fiber having a transverse cross-section characterized by the polymer having the same degree of modification across the transverse cross-section.

Advantageously, in some embodiments, without intending to be bound by theory, as the degree of modification of the polymer at the surface region of a fiber increases, relative to the degree of modification (if any) of the polymer in the inner region of the fiber, the bulk solubility of the fiber can increase or be maintain at the same level, allowing for more precise tuning of the solubility parameters of the fibers and different solubility characteristics of the fibers, relative to merely selecting a fiber having a consistent degree of modification or no degree of modification throughout the fiber.

The disclosure further provides a method of treating a fiber comprising contacting a surface of a fiber comprising a polymer comprising at least one of a vinyl acetate moiety or a vinyl alcohol moiety, e.g., only at least one vinyl acetate moiety, only at least one vinyl alcohol moiety, or both a vinyl acetate moiety and a vinyl alcohol moiety, with a modification agent and a solvent for the modification agent to chemically modify at least a portion of the polymer with the modification agent in a region of the fiber comprising at least the surface of the fiber. In embodiments, the contacting can be performed by immersion, spraying, transfer coating, wicking, foaming, brushing, rolling, humidification, vapor deposition, printing, or a combination thereof. In embodiments, the polymer is selected from the group consisting of a polyvinyl alcohol homopolymer, a polyvinyl alcohol copolymer, a modified polyvinyl alcohol copolymer, or a combination thereof. The modification agent can include any modification agent disclosed herein and the solvent for the modification agent can include any solvent disclosed herein. In embodiments, the method can further comprise contacting the surface of the fiber with the modification agent after formation of the fiber as part of a continuous inline process. For example, the fiber can be formed from a polymer mixture at a first station and then transferred to a second station where the surface of the fibers can be treated. In another example, the fiber can be treated on an apparatus including a fiber supply station, a fiber treating station, and a fiber collection station. In embodiments, the fiber is in motion during the contacting of the surface of the fibers. In embodiments, the contacting the surface of the fiber with the modification agent and a solvent is performed in a batch-by-batch process or a continuous in-line process. For example, the fibers can be prepared in bulk and can be treated with the modification agent prior to formation of the fibers into nonwoven webs. In embodiments, the fiber comprises staple fiber, staple yarn, fiber fill, needle punch fabrics, bonding fibers, or a combination thereof. In embodiments, the fiber comprises staple fiber. In embodiments, the method further comprises washing and drying the fiber after contacting the surface of the fiber with the modification agent. The washing can be by rinsing the fiber with a non-solvent. A non-solvent refers to a liquid that does not solubilize the fibers, but remove unreactive chemicals such as the modification agent. Examples of a non-solvent includes either polar or aprotic solvents. For example, acetone can be used. The drying the fiber can be by air jet drying, agitating, vortexing, or centrifuging.

In embodiments, the methods disclosed herein of treating a fiber comprising the polymer comprising a polyvinyl alcohol copolymer having a degree of hydrolysis in a range of from about 79% to about 99.9%, e.g., a degree of hydrolysis of 88%, 92%, or 96%, the modification agent comprises maleic anhydride, and the solvent comprises methanol, and the method further comprises admixing an activator comprising sodium hydroxide with the fiber, modification agent, and solvent. In embodiments, the methods disclosed herein of treating a fiber comprising the fiber comprises a polyvinyl alcohol copolymer having a degree of hydrolysis of 88%, 92%, or 96%, the modification agent comprises maleic anhydride, and the solvent comprises methanol, and admixing comprises combining the fiber and the solvent and heating the mixture to about 65° C. to about 75° C. to form a heated mixture; adding to the heated mixture the maleic anhydride and an activator comprising sodium hydroxide to form a reaction mixture; and stirring the reaction mixture at about 65° C. to about 75° C., for about 3 to 7 hours.

The disclosure provides a fiber treated according to the methods of the disclosure.

The disclosure provides a fiber having a surface region and an interior region. The fiber comprises a polymer comprising at least one of a vinyl acetate moiety or a vinyl alcohol moiety, e.g., only at least one vinyl acetate moiety, only at least one vinyl alcohol moiety, or both a vinyl acetate moiety and a vinyl alcohol moiety, chemically modified with a modification agent as described herein. The polymer in the fiber is chemically modified with the modification agent, for example, chemically bonded with the modification agent moiety through a reaction with the hydroxyl group in the vinyl alcohol moiety. In embodiments, the fiber has a transverse cross-section including an interior region having a first degree of modification and a surface region having a second degree of modification different from, e.g., greater than, the first degree of modification of the polymer in the interior region. The first degree of modification may be zero or greater than zero. When the first degree of modification is zero, the interior region of the fiber comprises the polymer including at least one a vinyl acetate moiety or a vinyl alcohol moiety, e.g., only at least one vinyl acetate moiety, only at least one vinyl alcohol moiety, or both a vinyl acetate moiety and a vinyl alcohol moiety, without modification, for example, polyvinyl alcohol, a polyvinyl alcohol copolymer, an anionically modified polyvinyl alcohol copolymer, or a combination thereof. In embodiments, the disclosure provides a fiber having a surface region and an interior region. In embodiments, the fiber comprises a polymer comprising vinyl acetate moieties and vinyl alcohol moieties modified with a modification agent. The fiber has a transverse cross-section including the interior region having the first degree of modification and the surface region having a second degree of modification greater than the first degree of modification.

The fiber of the disclosure can have a transverse cross-section of the fiber having an increasing gradient in the degree of modification of the polymer from the interior region to the surface region. In embodiments, the fiber of the disclosure can have a transverse cross-section of the fiber having the same degree of modification of the polymer from the interior region to the surface region. In some embodiments, the polymer before modification comprises polyvinyl alcohol, a copolymer of vinyl acetate and vinyl alcohol, an anionically modified polyvinyl alcohol copolymer, or a combination thereof. After the modification, the polymer is chemically bonded with the modification agent moieties through reaction between the hydroxyl groups in the vinyl alcohol and the modification agent.

As shown in FIG. 3, the disclosure provides a fiber comprising a transverse cross-section having a core-sheath structure or a core-shell structure. The fiber comprises a first region, e.g., a core region (denoted 401 in FIG. 3), comprising a polymer comprising at least one of a vinyl acetate moiety or a vinyl alcohol moiety, e.g., only at least one vinyl acetate moiety, only at least one vinyl alcohol moiety, or both a vinyl acetate moiety and a vinyl alcohol moiety. Such a polymer in the core region has no modification or has a first degree of modification with a modification agent. The first degree of modification can be zero or greater than zero. The fiber also comprises a second region, e.g., a sheath region (denoted 402 in FIG. 3), comprising such a polymer modified with the modification agent and having a second degree of modification, greater than the first degree of modification for the polymer of the first region. In embodiments, the fiber can comprise a transverse cross-section having a core-sheath structure. The fiber comprises a first region, e.g., a core region, comprising polyvinyl alcohol or a polyvinyl alcohol copolymer, and a second region, e.g., a sheath region, comprising such a polymer modified with a second degree of modification different than the first degree of modification in the first region. In embodiments, the fiber can comprise a transverse cross-section having a core-sheath structure. The fiber comprises a first region, e.g., a core region, comprising polyvinyl alcohol or a polyvinyl alcohol copolymer, and a second region, e.g., a sheath region, comprising such a polymer having a second degree of modification greater than the first degree of modification of the polymer in the first region. In some embodiments, the polyvinyl alcohol copolymer is a copolymer of vinyl acetate and vinyl alcohol before modification. The polymer in the fiber is chemically modified with the modification agent, for example, chemically bonded with the modification agent moiety through a reaction with the hydroxyl group in the vinyl alcohol moiety. In embodiments, the fiber further comprises at least one third region, e.g., at least one intermediate region (denoted 403 in FIG. 3), disposed between the first region and the second region and comprising the polymer having a third degree of modification intermediate between the first degree of modification of the polymer of the first region and the second degree of modification of the polymer of the second region. In embodiments, the fiber further comprises at least one third region, e.g., at least one intermediate region (denoted 403 in FIG. 3), disposed between the first region and the second region and comprising a polymer having a third degree of modification greater than the first degree of modification in the first region and less than the second degree of modification in the second region. In embodiments, the fiber can comprise a plurality of third regions, e.g., a plurality of intermediate regions (denoted 403*a*, 403*b* in FIG. 3), disposed between the first region and the second region. The transverse cross-section of the fiber has an increasing gradient in the degree of modification of the polymer from the first region to the second region. In embodiments, the plurality of third regions includes a polymer modified from polyvinyl alcohol or a polyvinyl alcohol copolymer with a modification agent. The transverse cross-section of the fiber has an increasing gradient in the degree of modification of the polymer from the first region to the second region.

In embodiments, the fibers of the disclosure can have a difference in the degree of modification of the polymers in the first and second regions of about 0.1%, about 0.3%, about 0.5%, about 0.7%, about 1%, about 2%, about 3%, about 4%, about 5%, about 6%, about 7%, about 8%, about 9%, about 10%, about 11%, about 12%, about 13%, about 14%, or about 15%, for example, in a range of 0.1% to 15%, about 0.3% to about 10%, about 0.5% to about 8%, about 1% to about 8%, about 2% to about 5%, about 1% to about 4%, or about 0.5% to about 5%. In embodiments, the transverse cross-section of the fiber can be characterized by a mean radius and the second region can comprise about 0.5% of the mean radius of the fiber, for example, about 1%, about 2%, about 3%, about 5%, about 7%, about 9%, about 10%, about 12%, about 15%, about 20%, about 25%, about 50%, about 75%, about 80%, about 85%, about 90%, about 92%, about 94%, about 96%, or about 98%, for example in a range of about 1% to about 98%, about 1% to about 90%, about 1% to about 75%, about 1% to about 50%, about 1% to about 25%, about 1% to about 20% about 1% to about 15%, about 1% to about 12% about 1% to about 10%, about 1% to about 8%, about 1% to about 6%, about 1% to about 5%, about 1% to about 4%, about 2% to about 25%, about 4% to about 25%, about 6% to about 35%, or about 8% to about 20%.

In embodiments, the polymer in the first, second, and optional third regions have the same degree of polymerization. In embodiments, the polymer in the first, second, and optional third regions can have the same degree of hydrolysis.

Although the fibers disclosed herein having a transverse cross-section characterized by a core-sheath structure or gradient degree of modification are described as having a greater degree of modification in the sheath and/or surface region of the fiber, it will be understood that the fibers can be prepared such that the degree of modification in the polymer of the sheath and/or surface region of the fiber is less than the degree of modification of the polymer of the core and/or inner surface region. Thus, the disclosure further provides a fiber having a surface region and an interior region. The fiber comprises a polymer comprising at least one of a vinyl acetate moiety or a vinyl alcohol moiety, e.g., only at least one vinyl acetate moiety, only at least one vinyl alcohol moiety, or both a vinyl acetate moiety and a vinyl alcohol moiety, chemically modified with a modification agent. The fiber has a transverse cross-section including the surface region having a lesser degree of modification than the degree of modification in the interior region. In embodiments, the disclosure provides a fiber having a surface region and an interior region. The fiber comprises polyvinyl alcohol and a polyvinyl alcohol copolymer. The fiber has a transverse cross-section including the polymer of the surface region having a lesser degree of modification than the degree of modification in the interior region.

The fiber of the disclosure can have a transverse cross-section of the fiber having a decreasing gradient in the degree of modification of the polymer from the interior region to the surface region. In embodiments, the fiber of the disclosure can have a transverse cross-section having a decreasing gradient in the degree of modification of the polyvinyl alcohol copolymer from the interior region to the surface region.

Nonwoven Webs

The nonwoven webs of the disclosure are generally sheet-like structures having two exterior surfaces, the nonwoven webs including a plurality of fibers. As used herein, and unless specified otherwise, the "exterior surface" of a nonwoven web refers to the faces of the sheet-like structure, denoted 100 and 101 in FIG. 5. A nonwoven web generally refers to an arrangement of fibers bonded to one another, wherein the fibers are neither woven nor knitted. In general, the plurality of fibers can be arranged in any orientation. In embodiments, the plurality of fibers are arranged randomly (i.e., do not have an orientation). In embodiments, the plurality of fibers are arranged in a unidirectional orientation. In embodiments, the plurality of fibers are arranged in a bidirectional orientation. In some embodiments, the plurality of fibers are multi-directional, having different arrangements in different areas of the nonwoven web. In embodiments, the nonwoven web can include a single type of water-soluble fiber. In embodiments, the nonwoven web can include a single type of water-insoluble fiber. In embodiments, the nonwoven web can include a single type of water-soluble fiber and one or more different types of water-insoluble fibers. In embodiments, the nonwoven web can include one or more different types of water-soluble fibers and one or more different types of water-insoluble fibers. In embodiments, the nonwoven web can consist of or consist essentially of water-soluble fibers. In embodiments, the nonwoven web can consist of or consist essentially of water-insoluble fibers. In some embodiments, the nonwoven web can include a single type of fiber forming material (i.e., all fibers have the same composition of fiber forming material), but can include fibers prepared by one or more fiber forming processes, e.g., wet cooled gel spinning, thermoplastic fiber spinning, melt blowing, spun bonding, or a combination thereof. In some embodiments, the nonwoven web can include a single type of fiber forming material and the fibers are made from a single fiber forming process. In some embodiments, the nonwoven web can include two or more fiber forming materials (e.g., blends of fibers having different compositions of fiber forming materials, fibers including blends of fiber forming materials, or both) and the fibers can be prepared by one or more fiber forming processes, e.g., wet-cool gel spinning, thermoplastic fiber spinning, melt blowing, spun bonding, or a combination thereof. In some embodiments, the nonwoven web can include two or more fiber forming materials and the fibers are made from a single fiber forming process. In embodiments, the fibers of the nonwoven web can have substantially the same diameters or different diameters.

In embodiments wherein the nonwoven webs of the disclosure include a blend of fibers including a first fiber and a second fiber, the first and second fibers can have a difference in length to diameter (L/D) ratio, tenacity, shape, rigidness, elasticity, solubility, melting point, glass transition temperature ($T_g$), fiber forming material, color, or a combination thereof.

As is well understood in the art, the term machine-direction (MD) refers to the direction of web travel as the nonwoven web is produced, for example on commercial nonwoven making equipment. Likewise, the term cross-direction (CD) refers to the direction in the plane of the web perpendicular to the machine-direction. With respect to nonwoven composite articles, wipes, absorbent articles or other article comprising a nonwoven composite article of the disclosure, the terms refer to the corresponding directions of the article with respect to the nonwoven web used to produce the article.

The tenacity of the nonwoven web can be the same or different from the tenacity of the fibers used to prepare the web. Without intending to be bound by theory, it is believed that the tenacity of the nonwoven web is related to the strength of the nonwoven web, wherein a higher tenacity provides a higher strength to the nonwoven web. In general, the tenacity of the nonwoven web can be modified by using fibers having different tenacities. The tenacity of the nonwoven web may also be affected by processing. In general, water-dispersible webs of the disclosure can have relatively high tenacities, i.e., the water-dispersible nonwoven web is a self-supporting web that can be used as the sole material for preparing an article and/or pouch. In embodiments, the nonwoven web is a self-supporting web. In contrast, the nonwoven webs that are prepared according to melt blowing, electro-spinning, and/or rotary spinning processes typically have low tenacities, and may not be self-supporting or capable of being used as a sole web for forming an article or pouch. Thus, in some embodiments, the nonwoven web is not self-supporting and is used in combination with a second nonwoven web and/or water-soluble film.

In embodiments, the nonwoven webs of the disclosure can have a ratio of tenacity in the machine direction to the tenacity in the cross direction (MD:CD) of in a range of about 0.5 to about 1.5, about 0.75 to about 1.5, about 0.80 to about 1.25, about 0.90 to about 1.1, or about 0.95 to about 1.05, or about 1. In embodiments, the nonwoven webs of the disclosure have a tenacity ratio MD:CD of about 0.8 to about 1.25. In embodiments the nonwoven webs of the disclosure have a tenacity ratio MD:CD of about 0.9 to about 1.1. In embodiments, the nonwoven webs of the disclosure have a tenacity of about 1. Without intending to be bound by theory, it is believed that as the tenacity ratio MD:CD approaches 1, the durability of the nonwoven is increased, providing superior resistance to breakdown of the nonwoven when stress is applied to the nonwoven during use, e.g., scrubbing with a flushable wipe comprising a nonwoven web of the disclosure, or pulling/tugging on the nonwoven caused by movement while wearing a wearable absorbent article.

The nonwoven webs of the disclosure have a rougher surface relative to a water-soluble film, which provides decreased contact between a surface and the nonwoven web than between a surface and the water-soluble film. Advantageously, this surface roughness can provide an improved feel to the consumer (i.e., a cloth-like hand-feel instead of a rubbery hand-feel), improved aesthetics (i.e., less glossy than a water-soluble film), and/or facilitate processability in preparing thermoformed, and/or vertical formed, filled, and sealed, and/or multichamber packets which require drawing the web along a surface of the processing equipment/mold. Accordingly, the fibers should be sufficiently coarse to provide a surface roughness to the resulting nonwoven web without being so coarse as to produce drag.

Nonwoven webs can be characterized by basis weight. The basis weight of a nonwoven is the mass per unit area of the nonwoven. Basis weight can be modified by varying manufacturing conditions, as is known in the art. A nonwoven web can have the same basis weight prior to and subsequent to bonding. Alternatively, the bonding method can change the basis weight of the nonwoven web. For example, wherein bonding occurs through the application of heat and pressure, the thickness of the nonwoven (and, thus, the area of the nonwoven) can be decreased, thereby increasing the basis weight. For another example, bonding among fibers can also occur during a through-air process at a suitable temperature, for example, in a range of from about 100° C. to about 200° C. (e.g., from 120° C. to 180° C.). Accordingly, as used herein and unless specified otherwise, the basis weight of a nonwoven refers to the basis weight of the nonwoven subsequent to bonding.

The nonwoven webs of the disclosure can have any basis weight in a range of about 0.1 g/m$^2$ to about 700 g/m$^2$, about 0.5 g/m$^2$ to about 600 g/m$^2$, about 1 g/m$^2$ to about 500 g/m$^2$, about 1 g/m$^2$ to about 400 g/m$^2$, about 1 g/m$^2$ to about 300 g/m$^2$, about 1 g/m$^2$ to about 200 g/m$^2$, about 1 g/m$^2$ to about 100 g/m$^2$, about 30 g/m$^2$ to about 100 g/m$^2$, about 20 g/m$^2$ to about 100 g/m$^2$, about 20 g/m$^2$ to about 80 g/m$^2$, or about 25 g/m$^2$ to about 70 g/m$^2$.

In embodiments, the nonwoven web can be carded and have a basis weight of about 5 g/m$^2$ to about 15 g/m$^2$, about 7 g/m$^2$ to about 13 g/m$^2$, about 9 g/m$^2$ to about 11 g/m$^2$, or about 10 g/m$^2$. In embodiments, the nonwoven web can be carded and can have a basis weight of 30 g/m$^2$ or more, for example in a range of 30 g/m$^2$ to about 70 g/m$^2$, about 30 g/m$^2$ to about 60 g/m$^2$, about 30 g/m$^2$ to about 50 g/m$^2$, about 30 g/m$^2$ to about 40 g/m$^2$, or about 30 g/m$^2$ to about 35 g/m$^2$. In embodiments, the nonwoven web can be melt-spun and have a basis weight in a range of about 1 g/m$^2$ to about 20 g/m$^2$, about 2 g/m$^2$ to about 15 g/m$^2$, about 3 g/m$^2$ to about 10 g/m$^2$, about 5 g/m$^2$ to about 15 g/m$^2$, about 7 g/m$^2$ to about 13 g/m$^2$, about 9 g/m$^2$ to about 11 g/m$^2$, or about 10 g/m$^2$. In embodiments, the nonwoven web can be melt-spun and can have a basis weight of about 0.1 g/m$^2$ to about 10 g/m$^2$, about 0.1 g/m$^2$ to about 8 g/m$^2$, about 0.2 g/m$^2$ to about 6 g/m$^2$, about 0.3 g/m$^2$ to about 4 g/m$^2$, about 0.4 g/m$^2$ to about 2 g/m$^2$, or about 0.5 g/m$^2$ to about 1 g/m$^2$.

Related to the basis weight is the fiber volume density and porosity of a nonwoven. Nonwoven webs, as prepared and prior to bonding, have a fiber density of about 30% or less by volume, i.e., for a given volume of nonwoven, 30% or less of the volume is made up of the fibers and the remaining volume is air. Thus, the nonwoven webs are highly porous. Fiber volume density and porosity of the nonwoven are inversely related characteristics of a nonwoven, for example, a nonwoven having a fiber volume density of about 30% by volume would have a porosity of about 70% by volume. It is well understood in the art that as the fiber volume density increases, the porosity decreases. Fiber volume density can be increased by increasing the basis weight of a nonwoven, for example, by bonding through the application of heat and pressure or hot through-air, potentially reducing the thickness (and, thus, the volume) of the nonwoven. Accordingly, as used herein and unless specified otherwise, the fiber volume density and porosity of a nonwoven refers to the fiber volume density and porosity of the nonwoven subsequent to bonding.

The nonwoven webs of the disclosure can have any porosity in a range of about 50% to about 95%, for example, at least about 50%, at least about 60%, at least about 70%, at least about 75%, or at least about 80% and up to about 95%, up to about 90%, up to about 85%, up to about 80%, up to about 75%, up to about 70%, or in a range of about 50% to about 95%, about 50% to about 80%, about 50% to about 70%, about 60% to about 75%, about 60% to about 80%, about 60% to about 90%, about 75% to about 85%, about 75% to about 90%, or about 75% to about 95%.

Pore sizes can be determined using high magnification and ordered surface analysis techniques including, but not limited to Brunauer-Emmett-Teller theory (BET), small angle X-ray scattering (SAXS), and molecular adsorption.

The nonwoven webs of the disclosure can have any thickness. Suitable thicknesses can include, but are not limited to, about 5 to about 10,000 μm (1 cm), about 5 to about 5,000 μm, about 5 to about 1,000 μm, about 5 to about 500 μm, about 200 to about 500 μm, about 5 to about 200 μm, about 20 to about 100 μm, or about 40 to about 90 μm, or about 50 to 80 μm, or about or about 60 to 65 μm for example 50 μm, 65 μm, 76 μm, or 88 μm. The nonwoven webs of the disclosure can be characterized as high loft or low loft. In general, loft refers to the ratio of thickness to basis weight. High loft nonwoven webs can be characterized by a high ratio of thickness to basis weight. As used herein, "high loft" refers to a nonwoven web of the disclosure having a basis weight as defined herein and a thickness exceeding 200 μm. The thickness of the nonwoven web can be determined by according to ASTM D5729-97, ASTM D5736, and ISO 9073-2:1995 and can include, for example, subjecting the nonwoven web to a load of 2 N and measuring the thickness. High loft materials can be used according to known methods in the art, for example, thru-air bonding or cross-lapping, which uses a cross-lapper to fold the unbounded web over onto itself to build loft and basis weight. Without intending to be bound by theory, in contrast to water-soluble films wherein the solubility of the film can be dependent on the thickness of the film; the solubility of a nonwoven web including water-soluble fibers is not believed to be dependent on the thickness of the web. In this regard, it is believed that because the individual fibers provide a higher surface area than a water soluble film, regardless of the thickness of the film, the parameter that limits approach of water to the fibers and, thereby, dissolution of the fibers in a water-soluble nonwoven web is the basis weight.

The water-solubility of the nonwoven webs of the disclosure can be a function of the type of fiber(s) used to prepare the web as well as the basis weight of the water-dispersible web. Without intending to be bound by theory, for a nonwoven web comprising a sole fiber type comprising a sole fiber forming material, it is believed that the solubility profile of a nonwoven web follows the same solubility profile of the fiber(s) used to prepare the nonwoven web, and the solubility profile of the fiber follows the same solubility profile of the fiber forming polymer(s) from which the fiber is prepared. For example, for nonwoven webs comprising PVOH fibers, the degree of hydrolysis and the degree of modification of the PVOH or PVOH copolymer can be chosen such that the water-solubility of the nonwoven web is also influenced. In general, at a given temperature, as the degree of modification of the PVOH or PVOH copolymer increases, water solubility of the polymer generally increases.

Modification of PVOH or PVOH copolymer increases the solubility of the polymer. Thus, it is expected that at a given temperature the solubility of a water-dispersible nonwoven web prepared from a modified PVOH copolymer, would be higher than that of a nonwoven web prepared from a PVOH copolymer without modification and having the same degree of hydrolysis as the PVOH copolymer. Further, it is expected that at a given temperature the solubility of a water dispersible nonwoven web prepared from a PVOH copolymer or a modified PVOH copolymer, that is treated by the methods as described herein to increase the degree of modification of the fibers, would be higher than that of a nonwoven web prepared without post-modification of the fibers as disclosed herein. Following these trends, a water-dispersible nonwoven web having specific solubility characteristics can be designed. In some embodiments, the water solubility of the fiber is maintained after modification with a modification agent, and the water solubility of the fiber can be approximately the same before and after the chemical modification with the modification agent.

Surprisingly, for a nonwoven web including a blend of fiber types, each fiber type having a sole fiber forming material, the solubility of the nonwoven web does not follow the rule of mixtures as would be expected for a blend of fiber types. Rather, for a nonwoven web including blend of two fiber types, when the two fiber types were provided in a ratio other than 1:1, the solubility of the nonwoven tended toward the solubility of the less soluble fiber (i.e., the fiber that requires higher temperatures to completely dissolve, and dissolves more slowly at temperatures below the complete dissolution temperature). For nonwoven webs including 1:1 blends of fibers, the solubility of the nonwoven web was generally lower than the solubility of the nonwoven webs including blends other than 1:1 blends (i.e., at a given temperature, the nonwoven webs including the 1:1 blends took longer to rupture, disintegrate, and dissolve than the nonwoven webs including, e.g., 3:1 and 1:3 ratios of fiber types). This trend was especially pronounced at temperatures lower than the complete dissolution temperature of the less soluble fiber.

Inclusion of a water-insoluble fiber in a nonwoven web can also be used to design a nonwoven web having specific solubility and/or delayed release properties (e.g., when the nonwoven web is included in a water-dispersible pouch). Without intending to be bound by theory, it is believed that as the weight percent of water-insoluble fiber included in a nonwoven web is increased (based on the total weight of the nonwoven web), the solubility of the nonwoven web generally decreases and the delayed release properties of a pouch comprising a nonwoven web generally increase. Upon contact with water at a temperature at or above the solubility temperature of the water-soluble fiber, a nonwoven web comprising a water-soluble fiber and water-insoluble fiber will begin to thin as the water-soluble fiber dissolves, thereby breaking down the web structure and/or increasing the pore size of the pores of the nonwoven web. In general, the larger the break-down of the web structure or increase in the pore size, the faster the water can access the contents of the pouch and the faster the contents of the pouch will be released. Similarly, delayed release of the contents of a pouch comprising the nonwoven web of the disclosure can be achieved by using a blend of water-soluble fibers having different solubility properties and/or different solubility temperatures. In general, for nonwoven webs including water-soluble fibers comprising a polyvinyl alcohol fiber forming materials, at water temperatures of 50% or more of the complete dissolution temperature of the water-soluble fibers (e.g., at 40° C. for a fiber having a complete dissolution temperature of 70° C.), the fibers will undergo polymer network swelling and softening, but the overall structure will remain intact. In embodiments wherein the nonwoven web includes a water-soluble fiber and a water-insoluble fiber, the ratio of soluble fiber to insoluble fiber is not particularly limited. The water-soluble fiber can comprise about 1% to about 99%, about 20% to about 80%, about 40% to about 90%, about 50% to about 90%, or about 60% to about 90% by weight of the total weight of the fibers and the water-insoluble fiber can comprise about 1% to about 99%, about 20% to about 80%, about 10% to about 60%, about 10% to about 50%, or about 10% to about 40% by weight of the total weight of the fibers.

Further, as the basis weight of the nonwoven web increases the rate of dissolution of the web decreases, provided the fiber composition and bonding parameters remain constant, as there is more material to be dissolved. For example, at a given temperature, a water-soluble web prepared from fibers comprising PVOH polymer(s) and having a basis weight of, e.g., 40 g/m$^2$, is expected to dissolve slower than an otherwise-identical nonwoven web having a basis weight of, e.g., 30 g/m$^2$. This relationship was especially prominent when the temperature of the water for dissolution was lower than the complete dissolution temperature of the fibers that made up the nonwoven web. Accordingly, basis weight can also be used to modify the solubility characteristics of the water-dispersible nonwoven web. The nonwoven web can generally have any basis weight in a range of about 1 g/m$^2$ to about 700 g/m$^2$, about 1 g/m$^2$ to about 600 g/m$^2$, about 1 g/m$^2$ to about 500 g/m$^2$, about 1 g/m$^2$ to about 400 g/m$^2$, about 1 g/m$^2$ to about 300 g/m$^2$, about 1 g/m$^2$ to about 200 g/m$^2$, about 1 g/m$^2$ to about 100 g/m$^2$, about 30 g/m$^2$ to about 100 g/m$^2$, about 20 g/m$^2$ to about 100 g/m$^2$, about 20 g/m$^2$ to about 80 g/m$^2$, about 25 g/m$^2$ to about 70 g/m$^2$, or about 30 g/m$^2$ to about 70 g/m$^2$.

Additionally, calendar settings have a secondary impact on the solubility profile of a nonwoven web of the disclosure. For example, for nonwoven webs having identical fiber chemistry and similar basis weights, at a given calendar pressure, the solubility time of a nonwoven web generally increases with increasing calendar temperature. This relationship was especially prominent when the temperature of the water for dissolution was lower than the complete dissolution temperature of the fibers that made up the nonwoven web.

Without intending to be bound by theory, it is believed that solubility (in terms of time to dissolution, for example according to MSTM-205) of a water-soluble nonwoven web is expected to surpass that of a water-soluble film of the same size (L×W) and/or mass, prepared from the same PVOH polymer. This is due to the higher surface area found in the nonwoven compared to a film, leading to faster solubilization.

The nonwoven web of the disclosure can include any of the auxiliary agents disclosed herein. Auxiliary agents can be dispersed throughout the web, e.g., between fibers, or applied to one of more surfaces of the nonwoven web. Auxiliary agents can be added to the nonwoven web during the melt-spun process, using a "co-form" process developed by Kimberly Clark, as is well known in the art. Auxiliary agents can also be added to one or more faces of a nonwoven web or article prepared therefrom, by any suitable means.

In embodiments, the nonwoven webs of the disclosure are substantially free of auxiliary agents. As used herein and unless specified otherwise, "substantially free of auxiliary agents" means that the nonwoven web includes less than about 0.01 wt %, less than about 0.005 wt. %, or less than about 0.001 wt. % of auxiliary agents, based on the total weight of the nonwoven web.

In a one embodiment, one or more stationary powder spray guns are used to direct an auxiliary agent powder stream towards the web or article, from one or more than one direction, while the web or article is transported through the coating zone by means of a belt conveyor. In an alternative embodiment, an article is conveyed through a suspension of an auxiliary agent powder in air. In yet another alternative embodiment, the articles are tumble-mixed with the auxiliary agent powder in a trough-like apparatus. In another embodiment, which can be combined with any other embodiment, electrostatic forces are employed to enhance the attraction between the auxiliary agent powder and the article. This type of process can be based on negatively charging the powder particles and directing these charged particles to the grounded articles. In other alternative embodiments, the auxiliary agent powder is applied to the article by a secondary transferring tool including, but not limited to, rotating brushes, which are in contact with the powder or by powdered gloves, which can transfer the powder from a container to the article. In yet another embodiment, the auxiliary agent powder is applied by dissolving or suspending the powder in a non-aqueous solvent or carrier, which is then atomized and sprayed onto the nonwoven or article. In one type of embodiment, the solvent or carrier subsequently evaporates, leaving the auxiliary agent powder behind. In one class of embodiments, the auxiliary agent powder is applied to the nonwoven or article in an accurate dose. This class of embodiments utilizes closed-system dry lubricant application machinery, such as PekuTECH's powder applicator PM 700 D. In this process the auxiliary agent powder, optionally batch-wise or continuously, is fed to a feed trough of application machinery. The nonwoven webs or articles are transferred from the output belt of a standard rotary drum pouch machine onto a conveyor belt of the powder application machine, wherein a controlled dosage of the auxiliary agent is applied to the nonwoven web or article.

Liquid auxiliary agents can be applied to a nonwoven web or article, for example, by spin casting, spraying a solution such as an aerosolized solution, roll coating, flow coating, curtain coating, extrusion, knife coating, or any combination thereof.

In embodiments, the nonwoven web can be colored, pigmented, and/or dyed to provide an improved aesthetic effect relative to water-soluble films. Suitable colorants can include an indicator dye, such as a pH indicator (e.g., thymol blue, bromothymol, thymolphthalein, and thymolphthalein), a moisture/water indicator (e.g., hydrochromic inks or leuco dyes), or a thermochromic ink, wherein the ink changes color when temperature increases and/or decreases. Suitable colorants include, but are not limited to, a triphenylmethane dye, an azo dye, an anthraquinone dye, a perylene dye, an indigoid dye, a food, drug and cosmetic (FD&C) colorant, an organic pigment, an inorganic pigment, or a combination thereof. Examples of colorants include, but are not limited to, FD&C Red #40; Red #3; FD&C Black #3; Black #2; Mica-based pearlescent pigment; FD&C Yellow #6; Green #3; Blue #1; Blue #2; titanium dioxide (food grade); brilliant black; and a combination thereof.

When included in a water-soluble fiber, the colorant can be provided in an amount of 0.01% to 25% by weight of the water-soluble polymer mixture, such as, 0.02%, 0.05%, 0.1%, 0.5%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, and 24% by weight of the water-soluble polymer mixture.

Advantageously, the nonwoven webs of the disclosure can demonstrate preferential shrinking in the presence of heat and/or water (e.g., humidity). Accordingly, the nonwoven webs can be heat and/or water shrunk when formed into packets. Further advantageously, the nonwoven webs of the disclosure can demonstrate increased robustness (i.e., mechanical properties) and improved solubility performance after storage in high heat and moisture environments (e.g., 38° C. and 80% relative humidity (RH)). Such increased robustness and improved solubility performance is surprising as the expectation based on compositionally similar water-soluble films is that the robustness and solubility performance would be unaffected by storage in high heat and moisture conditions. In particular, after removal of comparable water-soluble films from a conditioning environment, the water-soluble films will re-equilibrate with the surrounding environment leading to no long term or permanent changes in the performance properties of the films.

The nonwoven web of the disclosure can be used as a single layer or can be layered with other nonwoven webs and/or water-soluble films. In some embodiments, the nonwoven web includes a single layer of nonwoven web. In some embodiments, the nonwoven web is a multilayer nonwoven web comprising two or more layers of nonwoven webs. The one or more layers can be laminated to each other. In refinements of the foregoing embodiment, the two or more layers can be the same (e.g., be prepared from the same fibers and having the same basis weight). In refinements of the foregoing embodiment, the two or more layers can be different (e.g., be prepared from different types of fibers and/or have different basis weights). In embodiments, the nonwoven web can be laminated to a water-soluble film. In refinements of the foregoing embodiments, the nonwoven web and water-soluble film can be prepared from the same polymer (e.g., a PVOH copolymer a modified polymer having a specific viscosity, degree of hydrolysis, and amount of modification if a modified polymer). In refinements of the foregoing embodiments, the nonwoven web and water-soluble film can be prepared from different polymers (e.g., the polymer used to prepare the fibers of the nonwoven web can have different fiber chemistries (e.g., modifications), viscosities, degree of polymerization, degree of hydrolysis and/or solubility than the polymer that makes up the water-soluble film). Advantageously, multilayered nonwoven webs and laminates can be used to tune the moisture vapor transmission rate (MVTR) of a pouch or packet made therefrom. Multilayer materials can be prepared according to various processes known in the art, for example, melt extrusion, coating (e.g., solvent coating, aqueous coating, or solids coating), spray adhesion, material transfer, hot lamination, cold lamination, and combinations thereof.

A multilayer nonwoven web can have a basis weight that is the sum of the basis weights of the individual layers. Accordingly, a multilayer nonwoven web will take longer to dissolve than any of the individual layers provided as a single layer. In embodiments, the multilayer nonwoven can have a basis weight in a range of about 1 $g/m^2$ to about 100 $g/m^2$. Additionally, without intending to be bound by theory, it is believed that when pore sizes and pore arrangements are heterogeneous between layers, the pores in each layer will not align, thereby providing a multilayer nonwoven web having smaller pores than the individual layers. Accordingly, a nonporous water-dispersible nonwoven web can be prepared by layering multiple porous water-dispersible nonwoven webs.

The nonwoven web can also be laminated to a water-soluble film. The laminate can be formed using any known methods in the art including, but not limited to heat and pressure, hot through-air, chemical bonding, and/or solvent welding. Chemical bonding can include ionically or covalently functionalizing a surface of the nonwoven web and/or a surface of the water-soluble film such that when the surface of the nonwoven web comes in contact with the surface of the water-soluble film a chemical reaction occurs and covalently bonds the nonwoven web and water-soluble film together. The multilayer nonwoven web can include three or more layers. In embodiments, the multilayer nonwoven web can include a first layer comprising a water-soluble film, a second layer comprising a nonwoven web, and a third layer comprising a water-soluble film. In embodiments, the multilayer nonwoven web can include a first layer comprising a nonwoven web, a second layer comprising a water-soluble film, and a third layer comprising a nonwoven web.

Advantageously, the laminate can be prepared concurrently with pouch formation, e.g., using the heat applied during thermoforming to bond the nonwoven web and water-soluble film layers together. The water-soluble film can have the same solubility and/or chemical compatibility characteristics as the nonwoven web or the water-soluble film can have different solubility and/or chemical compatibility characteristics from the nonwoven web. In embodiments, the water-soluble film has the same solubility and/or chemical compatibility characteristics as the nonwoven web. In some embodiments, the water-soluble film has different solubility and/or chemical compatibility characteristics from the nonwoven web. Advantageously, when the water-soluble film has different solubility and/or chemical compatibility characteristics from the nonwoven web the laminate can be used to form a pouch having an interior surface with a first solubility and/or chemical compatibility and an exterior surface having a second solubility and/or chemical compatibility.

The water-soluble film used for a laminate can generally be any water-soluble film, e.g., one previously known in the art. The polymer used to form the water-soluble film can be any water-soluble polymer, or combination thereof, e.g., one described herein. The water-soluble film can contain at least about 50 wt. %, 55 wt. %, 60 wt. %, 65 wt. %, 70 wt. %, 75 wt. %, 80 wt. %, 85 wt. %, or 90 wt. % and/or up to about 60 wt. %, 70 wt. %, 80 wt. %, 90 wt. %, 95 wt. %, or 99 wt. % of a water-soluble polymer, e.g., a PVOH polymer, such as a PVOH copolymer, such a polymer modified with a modification agent, or any polymer blend thereof.

The water-soluble film can contain other auxiliary agents and processing agents, such as, but not limited to, plasticizers, plasticizer compatibilizers, surfactants, lubricants, release agents, fillers, extenders, cross-linking agents, anti-blocking agents, antioxidants, detackifying agents, anti-foams, nanoparticles such as layered silicate-type nanoclays (e.g., sodium montmorillonite), bleaching agents (e.g., sodium metabisulfite, sodium bisulfite or others), aversive agents such as bitterants (e.g., denatonium salts such as denatonium benzoate, denatonium saccharide, and denatonium chloride; sucrose octaacetate; quinine; flavonoids such as quercetin and naringen; and quassinoids such as quassin and brucine) and pungents (e.g., capsaicin, piperine, allyl isothiocyanate, and resinferatoxin), and other functional ingredients, in amounts suitable for their intended purposes. Embodiments including plasticizers are preferred. The amount of such agents can be up to about 50 wt. %, 20 wt %, 15 wt %, 10 wt %, 5 wt. %, 4 wt % and/or at least 0.01 wt. %, 0.1 wt %, 1 wt %, or 5 wt % of the film, individually or collectively.

The disclosure further provides a method of treating a nonwoven web comprising a plurality of fibers comprising a polymer comprising at least one of a vinyl acetate moiety or a vinyl alcohol moiety. The method comprises contacting at least a portion of the nonwoven web with a modification agent and a solvent to chemically modify the polymer in a region of each fiber therein with the modification agent or increase the degree of modification of the polymer of the fibers of the portion of the nonwoven web. The method provides a modified nonwoven web. In embodiments, the portion of the nonwoven web contacted with the modification agent can be a face of the nonwoven web. In embodiments, the contacting can be by immersion, spraying, transfer coating, wicking, foaming, brushing, rolling, humidification, vapor deposition, printing, or any combination thereof. In embodiments, the contacting occurs concurrently with bonding of the plurality of the fibers into the nonwoven web. In embodiments, the contacting and bonding comprises chemical bonding. In embodiments, the contacting and bonding comprises heat activated catalysis. The polymer comprising at least one of a vinyl acetate moiety or a vinyl alcohol moiety can be a polyvinyl acetate homopolymer, polyvinyl alcohol homopolymer, a polyvinyl alcohol copolymer, a modified polyvinyl alcohol copolymer, or any combination thereof as disclosed herein. In embodiments, the polymer is selected from a polyvinyl alcohol homopolymer, a polyvinyl alcohol copolymer, a modified polyvinyl alcohol copolymer, and any combination thereof. In embodiments, the polyvinyl alcohol copolymer is a copolymer of vinyl acetate and vinyl alcohol. In embodiments, the polyvinyl alcohol copolymer comprises an anionically modified copolymer. In embodiments, the anionically modified copolymer comprises a carboxylate, a sulfonate, or a combination thereof. In embodiments, the fiber further comprises an additional polymer. The modification agent can be any modification as disclosed herein. In embodiments, the modification agent can comprise an anhydride, a carboxylic acid, an alcohol, an ester, an ether, a sulfonic acid, a sulfonate, a click chemistry reagent, an amide, an amine, a lactam, a nitrile, a ketone, an allyl compound, an acetyl containing compound, a halogen containing compound, an alkyl containing compound, an imide, an acetal containing compound, an enolate, a nitro, a silane, an aziridine, an isocyanate, or a combination thereof. In embodiments, the modification agent can comprise an anhydride. Examples of a suitable anhydride are described above. In embodiments, the modification agent is provided in an amount of about 0.2% to about 75% (w/w) based on the weight of the solvent. In embodiments, the fiber is not soluble in the solvent prior to treatment, during treatment, and after treatment. In embodiments, the modification agent further comprises an activator as described herein.

The disclosure further provides a nonwoven web treated according to the method of the disclosure. The disclosure provides a nonwoven web comprising a plurality of fibers as described herein. The disclosure provides a multilayer nonwoven web comprising a first layer comprising a nonwoven web treated according to the method of the disclosure or a nonwoven web comprising the plurality of fibers of the disclosure. The polymer of the fibers in the nonwoven web is chemically modified, for example, bonded with the moiety of the modification agent through chemical reaction, for example, the reaction between the hydroxyl group (—OH) in the vinyl alcohol moiety and the modification agent.

Biodegradability

Polyvinyl alcohol polymers are biodegradable as they decompose in the presence of water and enzymes under aerobic, anaerobic, soil, and compost conditions (in the presence of water). In general, as the degree of hydrolysis of a polyvinyl alcohol polymer increases up to about 80%, the biodegradation activity of the polyvinyl alcohol polymer increases. Without intending to be bound by theory, it is believed that increasing the degree of hydrolysis above 80% does not appreciably affect biodegradability. Additionally, the stereoregularity of the hydroxyl groups of polyvinyl alcohol polymers has a large effect on the biodegradability activity level and the more isotactic the hydroxyl groups of the polymer sequence, the higher degradation activity becomes. Without intending to be bound by theory, for soil and/or compost biodegradation it is believed that a nonwoven web prepared from a polyvinyl alcohol fiber will have higher biodegradation activity levels relative to a water-soluble film prepared from a similar polyvinyl alcohol polymer, due to the increase in the polymer surface area provided by the nonwoven web, relative to a film. Further, without intending to be bound by theory, it is believed that while the degree of polymerization of the polyvinyl alcohol polymer has little to no effect on the biodegradability of a film or nonwoven web prepared with the polymer, the polymerization temperature may have an effect on the biodegradability of a film or nonwoven because the polymerization temperature can affect the crystallinity and aggregating status of a polymer. In particular as the crystallinity decreases, the polymer chain hydroxyl groups become less aligned in the polymer structure and the polymer chains become more disordered allowing for chains to accumulate as amorphous aggregates, thereby decreasing availability of ordered polymer structures such that the biodegradation activity is expected to decrease for soil and/or compost biodegradation mechanisms wherein the polymer is not dissolved. Without intending to be bound by theory, it is believed that because the stereoregularity of the hydroxyl groups of polyvinyl alcohol polymers has a large effect on biodegradability activity levels, the substitution of functionalities other than hydroxyl groups, such as with a modification agent (e.g., anionic AMPS functional groups, carboxylate groups, lactone groups, or the like) is expected to decrease the biodegradability activity level, relative to a polyvinyl alcohol copolymer without modification and having the same degree of hydrolysis, unless the functional group itself is also biodegradable, in which case biodegradability of the polymer can be increased with substitution. Further, it is believed that while the biodegradability activity level of a substituted polyvinyl alcohol can be less than that of the corresponding homopolymer, the substituted polyvinyl alcohol will still exhibit biodegradability.

Methods of determining biodegradation activity are known in the art, for example, as described in Chiellini et al., Progress in Polymer Science, Volume 28, Issue 6, 2003, pp. 963-1014, which is incorporated herein by reference in its entirety. Further methods and standards can be found in ECHA's Annex XV Restriction Report—Microplastics, Version number 1, Jan. 11, 2019, which is incorporated herein by reference in its entirety. Suitable standards include OECD 301B (ready biodegradability), OECD 301B (enhanced biodegradation), OECD 302B (inherent biodegradability), OECD 311 (anaerobic), ASTM D5988 (soil).

In embodiments, the fibers and nonwoven webs of the disclosure can be of the standard ready biodegradation, enhanced biodegradation, or inherent biodegradation. As used herein, the term "ready biodegradation" refers to a standard that is met if the material (e.g., a fiber) reached 60% biodegradation (mineralization) within 28 days of the beginning of the test, according to the OECD 301B test as described in said ECHA's Annex XV. As used herein, the term "enhanced biodegradation" refers to a standard that is met if the material (e.g., a fiber) reaches 60% biodegradation within 60 days from the beginning of the test, according to the OECD 301B test as described in said ECHA's Annex XV. In embodiments, the fibers and nonwoven webs of the disclosure meet the standards of ready biodegradation. In embodiments, the fibers and nonwoven webs of the disclosure meet the standards of ready biodegradation or enhanced degradation. In embodiments, the fibers and nonwoven webs of the disclosure meet the standards of inherent biodegradation. In embodiments, the fibers and nonwoven webs of the disclosure meet the standards of enhanced degradation. In embodiments, the fibers and nonwoven webs of the disclosure meet the standards of inherent biodegradation, enhanced biodegradation, or ready biodegradation. In embodiments, the laminate (nonwoven and film) of the disclosure meet the standards of ready biodegradation or enhanced biodegradation.

Uses

The nonwoven webs of the disclosure are suitable for a variety of commercial applications. Suitable commercial applications for the nonwoven webs of the disclosure can include, but are not limited to, water-dispersible or flushable pouches and packets; medical uses such as surgical masks, medical packaging, shoe covers, wound dressing, and drug delivery; filtration systems such as for gasoline and oil, mineral processing, vacuum bags, air filters, and allergen membranes or laminates; personal care products such as for baby wipes, makeup removing wipes, exfoliating clothes, makeup applicators, and wearable absorbent articles such as diapers and adult incontinence products; office products such as shopping bags or envelopes; and others such as lens cleaning wipes, cleanroom wipes, potting material for plants, antibacterial wipes, agricultural seed strips, fabric softener sheets, garment/laundry bags, food wrapping, floor care wipes, pet care wipes, polishing tools, dust removal, and hand cleaning.

Sealed Pouches

The disclosure further provides a pouch comprising a nonwoven web according to the disclosure in the form of a pouch defining an interior pouch volume. In some embodiments, the pouch can include a laminate comprising a water-soluble film and a nonwoven web of the disclosure. The pouch can be a water-dispersible pouch, optionally a water-soluble pouch and/or a flushable pouch. The disclosure further provides a method of preparing a packet comprising a nonwoven web of the disclosure, the method comprising forming a nonwoven web into the form of a pouch, filling the pouch with a composition to be enclosed therein, and sealing the pouch to form a packet. In some embodiments, sealing includes heat sealing, solvent welding, adhesive sealing, or a combination thereof.

The nonwoven webs and laminates disclosed herein are useful for creating a sealed article in the form of a pouch defining an interior pouch volume to contain a composition therein for release into an aqueous environment. A "sealed article" optionally encompasses sealed compartments having a vent hole, for example, in embodiments wherein the compartment encloses a solid that off-gasses, but more commonly will be a completely sealed compartment.

The pouches may comprise a single compartment or multiple compartments. A pouch can be formed from two layers of nonwoven web or laminate sealed at an interface, or by a single nonwoven web or laminate that is folded upon itself and sealed. The nonwoven web or laminate forms at least one sidewall of the pouch, optionally the entire pouch, and preferably an outer surface of the at least one sidewall. In another type of embodiment, the nonwoven web or laminate forms an inner wall of the packet, e.g., as a dividing wall between compartments. The nonwoven web or laminate can also be used in combination with a water-soluble film, e.g., as an exterior wall, inner wall, and/or compartment lid.

The composition enclosed in the pouch is not particularly limited, for example including any of the variety of compositions described herein. In embodiments comprising multiple compartments, each compartment may contain identical and/or different compositions. In turn, the compositions may take any suitable form including, but not limited to liquid, solid, gel, paste, mull, pressed solids (tablets) and combinations thereof (e.g., a solid suspended in a liquid).

In some embodiments, the pouches comprise multiple compartments. The multiple compartments are generally superposed such that the compartments share a partitioning wall interior to the pouch. The compartments of multi-compartment pouches may be of the same or different size(s) and/or volume(s). The compartments of the present multi-compartment pouches can be separate or conjoined in any suitable manner. In embodiments, the second and/or third and/or subsequent compartments are superimposed on the first compartment. In one embodiment, the third compartment may be superimposed on the second compartment, which is in turn superimposed on the first compartment in a sandwich configuration. Alternatively, the second and third compartments may be superimposed on the first compartment. However it is also equally envisaged that the first, the second and/or third and/or subsequent compartments are orientated side-by-side or in concentric orientations. The compartments may be packed in a string, each compartment being individually separable by a perforation line. Hence, each compartment may be individually torn-off from the remainder of the string by the end-user. In some embodiments, the first compartment may be surrounded by at least the second compartment, for example in a tire-and-rim configuration, or in a pouch-in-a-pouch configuration.

The geometry of the compartments may be the same or different. In embodiments the optionally third and subsequent compartments each have a different geometry and shape as compared to the first and second compartment. In these embodiments, the optionally third and subsequent compartments are arranged in a design on the first or second compartment. The design may be decorative, educative, or illustrative, for example to illustrate a concept or instruction, and/or used to indicate origin of the product.

Methods of Making Pouches

Pouches and packets may be made using any suitable equipment and method. For example, single compartment pouches may be made using vertical form filling, horizontal form filling, or rotary drum filling techniques commonly known in the art. Such processes may be either continuous or intermittent. The nonwoven web, layered nonwoven web and film, or laminate structure may be dampened, and/or heated to increase the malleability thereof. The method may also involve the use of a vacuum to draw the nonwoven web, layered nonwoven web and film, or laminate structure into a suitable mold. The vacuum drawing the nonwoven web or laminate into the mold can be applied for about 0.2 to about 5 seconds, or about 0.3 to about 3, or about 0.5 to about 1.5 seconds, once the nonwoven web, layered nonwoven web and film, or laminate structure is on the horizontal portion of the surface. This vacuum can be such that it provides an under-pressure in a range of 10 mbar to 1000 mbar, or in a range of 100 mbar to 600 mbar, for example.

The molds, in which packets may be made, can have any shape, length, width and depth, depending on the required dimensions of the pouches. The molds may also vary in size and shape from one to another, if desirable. For example, the volume of the final pouches may be about 5 ml to about 300 ml, or about 10 ml to 150 ml, or about 20 ml to about 100 ml, and that the mold sizes are adjusted accordingly.

Thermoforming

A thermoformable nonwoven web or laminate is one that can be shaped through the application of heat and a force. Thermoforming a nonwoven web, layered nonwoven web and film, or laminate structure is the process of heating the nonwoven web, layered nonwoven web and film, or laminate structure, shaping it (e.g., in a mold), and then allowing the resulting nonwoven web or laminate to cool, whereupon the nonwoven web or laminate will hold its shape, e.g., the shape of the mold. The heat may be applied using any suitable means. For example, the nonwoven web or laminate may be heated directly by passing it under a heating element or through hot air, prior to feeding it onto a surface or once on a surface. Alternatively, it may be heated indirectly, for example by heating the surface or applying a hot item onto the nonwoven web or laminate. In embodiments, the nonwoven web or laminate is heated using an infrared light. The nonwoven web or laminate may be heated to a temperature in a range of about 50° C. to about 200° C., about 50° C. to about 170° C., about 50° C. to about 150° C., about 50° C. to about 120° C., about 60° C. to about 130° C., about 70° C. to about 120° C., or about 60° C. to about 90° C. Thermoforming can be performed by any one or more of the following processes: the manual draping of a thermally softened nonwoven web or laminate over a mold, or the pressure induced shaping of a softened nonwoven web or laminate to a mold (e.g., vacuum forming), or the automatic high-speed indexing of a freshly extruded sheet having an accurately known temperature into a forming and trimming station, or the automatic placement, plug and/or pneumatic stretching and pressuring forming of a nonwoven web or laminate.

Alternatively, the nonwoven web or laminate can be wetted by any suitable means, for example directly by spraying a wetting agent (including water, a polymer composition, a plasticizer for the nonwoven web or laminate composition, or any combination of the foregoing) onto the nonwoven web or laminate, prior to feeding it onto the surface or once on the surface, or indirectly by wetting the surface or by applying a wet item onto the nonwoven web or laminate.

Once a nonwoven web or laminate has been heated and/or wetted, it may be drawn into an appropriate mold, preferably using a vacuum. The filling of the molded nonwoven web or laminate can be accomplished by utilizing any suitable means. In embodiments, the most preferred method will depend on the product form and required speed of filling. In embodiments, the molded nonwoven web or laminate is filled by in-line filling techniques. The filled, open packets are then closed forming the pouches, using a second nonwoven web or laminate, by any suitable method. This may be accomplished while in horizontal position and in continuous, constant motion. The closing may be accomplished by continuously feeding a second nonwoven web or laminate, preferably water-soluble nonwoven web or laminate, over and onto the open packets and then preferably sealing the first and second nonwoven web or laminate together, typically in the area between the molds and thus between the packets.

Sealing the Pouches

Any suitable method of sealing the pouch and/or the individual compartments thereof may be utilized. Non-limiting examples of such means include heat sealing, solvent welding, solvent or wet sealing, and combinations thereof. Typically, only the area that is to form the seal is treated with heat or solvent. The heat or solvent can be applied by any method, typically on the closing material, and typically only on the areas which are to form the seal. If solvent or wet sealing or welding is used, it may be preferred that heat is also applied. Preferred wet or solvent sealing/welding methods include selectively applying solvent onto the area between the molds, or on the closing material, by for example, spraying or printing this onto these areas, and then applying pressure onto these areas, to form the seal. Sealing rolls and belts (optionally also providing heat) can be used, for example.

In embodiments, an inner nonwoven web or laminate is sealed to outer nonwoven web(s) or laminate(s) by solvent sealing. The sealing solution is generally an aqueous solution. In embodiments, the sealing solution includes water. In embodiments, the sealing solution includes water and further includes one or more polyols, diols and/or glycols such as 1,2-ethanediol (ethylene glycol), 1,3-propanediol, 1,2-propanediol, 1,4-butanediol (tetramethylene glycol), 1,5-pantanediol (pentamethylene glycol), 1,6-hexanediol (hexamethylene glycol), 2,3-butanediol, 1,3-butanediol, 2-methyl-1,3-propanediol, various polyethylene glycols (e.g., diethylene glycol, triethylene glycol), and combinations thereof. In embodiments, the sealing solution includes erythritol, threitol, arabitol, xylitol, ribitol, mannitol, sorbitol, galactitol, fucitol, iditol, inositol, volemitol, isomal, maltitol, lactitol, or any combination thereof. In embodiments, the sealing solution includes a water-soluble polymer.

The sealing solution can be applied to the interfacial areas of the inner nonwoven web or laminate in any amount suitable to adhere the inner and outer nonwoven webs or laminates. As used herein, the term "coat weight" refers to the amount of sealing solution applied to the nonwoven web or laminate in grams of solution per square meter of nonwoven web or laminate. In general, when the coat weight of the sealing solvent is too low, the nonwoven webs or laminates do not adequately adhere and the risk of pouch failure at the seams increases. Further, when the coat weight of the sealing solvent is too high, the risk of the solvent migrating from the interfacial areas increases, increasing the likelihood that etch holes may form in the sides of the pouches. The coat weight window refers to the range of coat weights that can be applied to a given film while maintaining both good adhesion and avoiding the formation of etch holes. A broad coat weight window is desirable as a broader window provides robust sealing under a broad range of operations. Suitable coat weight windows are at least about 3 $g/m^2$, or at least about 4 $g/m^2$, or at least about 5 $g/m^2$, or at least about 6 $g/m^2$.

Cutting the Packets

Formed packets may be cut by a cutting device. Cutting can be accomplished using any known method. It may be preferred that the cutting is also done in continuous manner, and preferably with constant speed and preferably while in horizontal position. The cutting device can, for example, be a sharp item, or a hot item, or a laser, whereby in the latter cases, the hot item or laser 'burns' through the film/sealing area.

Forming and Filling Multi-Compartment Pouches

The different compartments of a multi-compartment pouches may be made together in a side-by-side style or concentric style wherein the resulting, cojoined pouches may or may not be separated by cutting. Alternatively, the compartments can be made separately.

In embodiments, pouches may be made according to a process comprising the steps of: a) forming a first compartment (as described above); b) forming a recess within or all of the closed compartment formed in step (a), to generate a second molded compartment superposed above the first compartment; c) filling and closing the second compartments by means of a third nonwoven web, laminate, or film; d) sealing the first, second and third nonwoven web, laminate, or film; and e) cutting the nonwoven webs or laminates to produce a multi-compartment pouch. The recess formed in step (b) may be achieved by applying a vacuum to the compartment prepared in step (a).

In embodiments, second, and/or third compartment(s) can be made in a separate step and then combined with the first compartment as described in European Patent Application Number 08101442.5 or U.S. Patent Application Publication No. 2013/240388 A1 or WO 2009/152031.

In embodiments, pouches may be made according to a process comprising the steps of: a) forming a first compartment, optionally using heat and/or vacuum, using a first nonwoven web or laminate on a first forming machine; b) filling the first compartment with a first composition; c) optionally filling the second compartment with a second composition; d) sealing the first and optional second compartment with a second nonwoven web or laminate to the first nonwoven web or laminate; and e) cutting the nonwoven webs or laminates to produce a multi-compartment pouch.

In embodiments, pouches may be made according to a process comprising the steps of: a) forming a first compartment, optionally using heat and/or vacuum, using a first nonwoven web or laminate on a first forming machine; b) filling the first compartment with a first composition; c) on a second forming machine, deforming a second nonwoven web or laminate, optionally using heat and vacuum, to make a second and optionally third molded compartment; d) filling the second and optionally third compartments; e) sealing the second and optionally third compartment using a third nonwoven web or laminate; f) placing the sealed second and optionally third compartments onto the first compartment; g) sealing the first, second and optionally third compartments; and h) cutting the nonwoven web or laminate to produce a multi-compartment pouch.

The first and second forming machines may be selected based on their suitability to perform the above process. In embodiments, the first forming machine is preferably a horizontal forming machine, and the second forming machine is preferably a rotary drum forming machine, preferably located above the first forming machine.

It should be understood that by the use of appropriate feed stations, it may be possible to manufacture multi-compartment pouches incorporating a number of different or distinctive compositions and/or different or distinctive liquid, gel or paste compositions.

In embodiments, the nonwoven web or laminate and/or pouch is sprayed or dusted with a suitable material, such as an active agent, a lubricant, an aversive agent, or mixtures thereof. In embodiments, the nonwoven web or laminate and/or pouch is printed upon, for example, with an ink and/or an active agent.

Vertical Form, Fill and Seal

In embodiments, the nonwoven web or laminate of the disclosure can be formed into a sealed article. In embodiments, the sealed article is a vertical form, filled, and sealed article. The vertical form, fill, and seal (VFFS) process is a conventional automated process. VFFS includes an apparatus such as an assembly machine that wraps a single piece of the nonwoven web or laminate around a vertically oriented feed tube. The machine heat seals or otherwise secures the opposing edges of the nonwoven web or laminate together to create the side seal and form a hollow tube of nonwoven web or laminate. Subsequently, the machine heat seals or otherwise creates the bottom seal, thereby defining a container portion with an open top where the top seal will later be formed. The machine introduces a specified amount of flowable product into the container portion through the open top end. Once the container includes the desired amount of product, the machine advances the nonwoven web or laminate to another heat sealing device, for example, to create the top seal. Finally, the machine advances the nonwoven web or laminate to a cutter that cuts the film immediately above the top seal to provide a filled package.

During operation, the assembly machine advances the nonwoven web or laminate from a roll to form the package. Accordingly, the nonwoven web or laminate must be able to readily advance through the machine and not adhere to the machine assembly or be so brittle as to break during processing.

Pouch Contents

In any embodiment, the pouch can contain (enclose) a composition in the defined interior volume of the pouch. The composition can be selected from a liquid, solid or combination thereof. In embodiments wherein the composition includes a liquid, the nonwoven web can be a nonporous nonwoven web or a porous nonwoven web laminated with a water-soluble film, the water-soluble film forming the inner surface of the pouch. In embodiments wherein the composition is a solid, the pouch can comprise a nonporous nonwoven web, a porous nonwoven web laminated with a water-soluble film, or a porous nonwoven web. In embodiments wherein the pouch includes a porous nonwoven web, the particle size of the solid composition is smaller than the pore size of the nonwoven web.

In embodiments, the sealed articles of the disclosure can enclose in the interior pouch volume a composition comprising a liquid laundry detergent, an agricultural composition, an automatic dish washing composition, household cleaning composition, a water-treatment composition, a personal care composition, a food and nutritive composition, an industrial cleaning composition, a medical composition, a disinfectant composition, a pet composition, an office composition, a livestock composition, an industrial composition, a marine composition, a mercantile composition, a military composition, a recreational composition, or a combination thereof. In embodiments, the water-dispersible sealed articles of the disclosure can enclose in the interior pouch volume a composition comprising a liquid laundry detergent, an agricultural composition, an automatic dish washing composition, a household cleaning composition, a water-treatment composition, a personal care composition, a food and nutritive composition, an industrial cleaning composition, or a combination thereof. In embodiments, the water-dispersible sealed articles of the disclosure can enclose in the interior pouch volume a composition comprising a liquid laundry detergent, an agricultural composition, an automatic dish washing composition, a household cleaning composition, a water-treatment composition, a personal care composition, or a combination thereof. In embodiments, the water-dispersible sealed articles of the disclosure can enclose in the interior pouch volume a composition comprising an agricultural composition or a water-treatment composition.

As used herein, "liquid" includes free-flowing liquids, as well as pastes, gels, foams and mousses. Non-limiting examples of liquids include light duty and heavy duty liquid detergent compositions, dish detergent for hand washing and/or machine washing; hard surface cleaning compositions, fabric enhancers, detergent gels commonly used for laundry, bleach and laundry additives, shaving creams, skin care, hair care compositions (shampoos and conditioners), and body washes. Such detergent compositions may comprise a surfactant, a bleach, an enzyme, a perfume, a dye or colorant, a solvent and combinations thereof. Optionally, the detergent composition is selected from the group consisting of a laundry detergent, a dishwashing detergent, a hard surface cleaning composition, fabric enhancer compositions, shaving creams, skin care, hair care compositions (shampoos and conditioners), and body washes, and combinations thereof.

Non-limiting examples of liquids include agricultural compositions, automotive compositions, aviation compositions, food and nutritive compositions, industrial compositions, livestock compositions, marine compositions, medical compositions, mercantile compositions, military and quasi-military compositions, office compositions, recreational and park compositions, pet compositions, and water-treatment compositions, including cleaning and detergent compositions applicable to any such use.

Gases, e.g., suspended bubbles, or solids, e.g., particles, may be included within the liquids. A "solid" as used herein includes, but is not limited to, powders, agglomerates, and mixtures thereof. Non-limiting examples of solids include: granules, micro-capsules, beads, noodles, and pearlised balls. Solid compositions may provide a technical benefit including, but not limited to, through-the-wash benefits, pre-treatment benefits, and/or aesthetic effects.

The composition may be a non-household care composition. For example, a non-household care composition can be selected from agricultural compositions, aviation compositions, food and nutritive compositions, industrial compositions, livestock compositions, marine compositions, medical compositions, mercantile compositions, military and quasi-military compositions, office compositions, recreational and park compositions, pet compositions, and water-treatment compositions, including cleaning and detergent compositions applicable to any such use while excluding fabric and household care compositions In one type of embodiment, the composition can include an agrochemical, e.g., one or more insecticides, fungicides, herbicides, pesticides, miticides, repellants, attractants, defoliaments, plant growth regulators, fertilizers, bactericides, micronutrients, and trace elements. Suitable agrochemicals and secondary agents are described in U.S. Pat. Nos. 6,204,223 and 4,681,228 and EP 0989803 A1. For example, suitable herbicides include paraquat salts (for example paraquat dichloride or paraquat bis(methylsulphate), diquat salts (for example diquat dibromide or diquat alginate), and glyphosate or a salt or ester thereof (such as glyphosate isopropylammonium, glyphosate sesquisodium or glyphosate trimesium, also known as sulfosate). Incompatible pairs of crop protection chemicals can be used in separate chambers, for example as described in U.S. Pat. No. 5,558,228. Incompatible pairs of crop protection chemicals that can be used include, for example, bensulfuron methyl and molinate; 2,4-D and thifensulfuron methyl; 2,4-D and methyl 2-[[[[N-4-methoxy-6-methyl-1,3,5-triazine-2-yl)-N-methylamino]carbonyl]amino]-sulfonyl]benzoate; 2,4-D and metsulfuron methyl; maneb or mancozeb and benomyl; glyphosate and metsulfuron methyl; tralomethrin and any organophosphate such as monocrotophos or dimethoate; bromoxynil and N-[[4,6-dimethoxypyrimidine-2-yl)-amino] carbonyl]-3-(ethylsulfonyl)-2-pyridine-sulfonamide; bromoxynil and methyl 2-[[[[(4-methyl-6-methoxy)-1,3,5-triazin-2-yl)amino]carbonyl]amino]sulfonyl]-benzoate; bromoxynil and methyl 2-[[[[N-(4-methoxy-6-methyl-1,3,5-triazin-2-yl)-N-methylamino]carbonyl]amino]-sulfonyl] benzoate. In another, related, type of embodiment, the composition can include one or more seeds, optionally together with soil, and further optionally together with one or more additional components selected from mulch, sand, peat moss, water jelly crystals, and fertilizers, e.g., including types of embodiments described in U.S. Pat. No. 8,333,033.

In another type of embodiment, the composition is a water-treatment agent. Such agents can include harsh chemicals, such as aggressive oxidizing chemicals, e.g., as described in U.S. Patent Application Publication No. 2014/0110301 and U.S. Pat. No. 8,728,593. For example, sanitizing agents can include hypochlorite salts such as sodium hypochlorite, calcium hypochlorite, and lithium hypochlorite; chlorinated isocyanurates such as dichloroisocyanuric acid (also referred to as "dichlor" or dichloro-s-triazinetrione, 1,3-dichloro-1,3,5-triazinane-2,4,6-trione) and trichloroisocyanuric acid (also referred to as "trichlor" or 1,3,5-trichloro-1,3,5-triazinane-2,4,6-trione). Salts and hydrates of the sanitizing compounds are also contemplated. For example, dichloroisocyanuric acid may be provided as sodium dichloroisocyanurate, sodium dichloroisocyanurate acid dihydrate, among others. Bromine containing sanitizing agents may also be suitable for use in unit dose packaging applications, such as 1,3-dibromo-5,5-dimethylhydantoin (DBDMH), 2,2-dibromo-3-nitrilopropionamide (DBNPA), dibromocyano acetic acid amide, 1-bromo-3-chloro-5,5-dimethylhydantoin; and 2-bromo-2-nitro-1,3-propanediol, among others. The oxidizing agent can be one described in U.S. Pat. No. 7,476,325, e.g., potassium hydrogen peroxymonosulfate. The composition can be a pH-adjusting chemical, e.g., as described in U.S. Patent Application Publication No. 2008/0185347, and can include, for example, an acidic component and an alkaline component such that the composition is effervescent when contacted with water, and adjusts the water pH. Suitable ingredients include sodium bicarbonate, sodium bisulfate, potassium hydroxide, sulfamic acid, organic carboxylic acids, sulfonic acids, and potassium dihydrogen phosphate. A buffer blend can include boric acid, sodium carbonate, glycolic acid, and oxone monopersulfate, for example.

A water-treatment agent can be or can include a flocculant, e.g., as described in U.S. Patent Application Publication No. 2014/0124454. The flocculant can include a polymer flocculant, e.g., polyacrylamide, a polyacrylamide copolymer such as an acrylamide copolymers of diallydimethylammonium chloride (DADMAC), dimethylaminoethylacrylate (DMAEA), dimethylaminoethylmethacrylate (DMAEM), 3-methylamidepropyltrimethylammonium chloride (MAPTAC) or acrylic acid; a cationic polyacrylamide; an anionic polyacrylamide; a neutral polyacrylamide; a polyamine; polyvinylamine; polyethylene imine; polydimethyldiallylammonium chloride; poly oxyethylene; polyvinyl alcohol; polyvinyl pyrrolidone; polyacrylic acid; polyphosphoric acid; polystyrene sulfonic acid; or any combination thereof. A flocculant can be selected from chitosan acetate, chitosan lactate, chitosan adipate, chitosan glutamate, chitosan succinate, chitosan malate, chitosan citrate, chitosan fumarate, chitosan hydrochloride, and combinations thereof. The water-treating composition can include a phosphate removing substance, e.g., one or more selected from a zirconium compound, a rare earth lanthanide salt, an aluminum compound, an iron compound, or any combination thereof.

The composition can be a limescale removing composition, e.g., citric or maleic acid or a sulfate salt thereof, or any mixture thereof, e.g., as described in U.S. Patent Application No. 2006/0172910.

Various other types of compositions are contemplated for use in the packets described herein, including particulates, for example down feathers, e.g., as described in U.S. RE29059 E; super absorbent polymers, e.g., as described in U.S. Patent Application Publication Nos. 2004/0144682 and 2006/0173430; pigments and tinters, e.g., as described in U.S. Pat. No. 3,580,390 and U.S. Patent Application Publication No. 2011/0054111; brazing flux (e.g., alkali metal fluoroaluminates, alkali metal fluorosilicates and alkali metal fluorozincates), e.g., as described in U.S. Pat. No. 8,163,104; food items (e.g., coffee powder or dried soup) as described in U.S. Patent Application Publication No. 2007/0003719; and wound dressings, e.g., as described in U.S. Pat. No. 4,466,431.

In pouches comprising laundry, laundry additive and/or fabric enhancer compositions, the compositions may comprise one or more of the following non-limiting list of ingredients: fabric care benefit agent; detersive enzyme; deposition aid; rheology modifier; builder; bleach; bleaching agent; bleach precursor; bleach booster; bleach catalyst; perfume and/or perfume microcapsules (see for example U.S. Pat. No. 5,137,646); perfume loaded zeolite; starch encapsulated accord; polyglycerin esters; whitening agent; pearlescent agent; enzyme stabilizing systems; scavenging agents including fixing agents for anionic dyes, complexing agents for anionic surfactants, and mixtures thereof; optical brighteners or fluorescers; polymer including but not limited to soil release polymer and/or soil suspension polymer; dispersants; antifoam agents; non-aqueous solvent; fatty acid; suds suppressors, e.g., silicone suds suppressors (see: U.S. Patent Application Publication No. 2003/0060390 A1, ¶65-77); cationic starches (see: U.S. Patent Application Publication No. 2004/0204337 A1 and US 2007/0219111 A1); scum dispersants (see: U.S. Patent Application Publication No. 2003/0126282 A1, ¶89-90); substantive dyes; hueing dyes (see: U.S. Patent Application Publication No. 2014/0162929 A1); colorants; opacifier; antioxidant; hydrotropes such as toluenesulfonates, cumenesulfonates and naphthalenesulfonates; color speckles; colored beads, spheres or extrudates; clay softening agents; anti-bacterial agents. Any one or more of these ingredients is further described in described in U.S. Patent Application Publication No. 2010/305020 A1, U.S. Patent Application Publication No. 2003/0139312A1 and U.S. Patent Application Publication No. 2011/0023240 A1. Additionally or alternatively, the compositions may comprise surfactants, quaternary ammonium compounds, and/or solvent systems. Quaternary ammonium compounds may be present in fabric enhancer compositions, such as fabric softeners, and comprise quaternary ammonium cations that are positively charged polyatomic ions of the structure $NR_4^+$, where R is an alkyl group or an aryl group.

Composite Articles

Composite articles of the disclosure include at least two layers of nonwoven webs. The composite articles of the disclosure can have a first layer of a first nonwoven web including a first plurality of fibers having a first diameter, a second layer of a second nonwoven web comprising a second plurality of fibers having a second diameter, and a first interface comprising at least a portion of the first nonwoven web and at least a portion of the second nonwoven web, wherein the portion of the first nonwoven web and the portion of the second nonwoven web are fused, and wherein the second diameter is smaller than the first diameter. Any nonwoven layer of the composite article can include a water-soluble film laminated thereto.

Composite articles of the disclosure can provide one or more advantages, including but not limited to, increased mechanical strength relative to a nonwoven web identical to a single layer of the composite article alone, enhanced liquid acquisition function relative to a nonwoven web identical to a single layer of the composite article alone (e.g., for a liquid acquisition layer of a diaper, or for a spill absorbing wipe), and/or enhanced retention of fluids and/or active compositions relative to a nonwoven web identical to a single layer of the composite article alone (e.g., an active lotion for a wet wipe).

The first interface including at least a portion of the first nonwoven web and at least a portion of the second nonwoven web is the area of the composite where the first and second nonwoven webs overlap and the first plurality of fibers and the second plurality of fibers are intermingled. In general, the portion of the first nonwoven web that forms the first interface is an exterior surface of the first nonwoven web. In embodiments, the first interface comprises 50% or less of the thickness of the first nonwoven web, 40% or less, 30% or less, 25% or less, 20% or less, 10% or less, 5% or less, 2.5% or less, or 1% or less of the thickness of the first nonwoven web. In embodiments, the first interface comprises at least 0.1%, at least 0.5%, at least 1%, or at least 5% of the thickness of the first nonwoven. In embodiments, the first interface comprises about 0.1% to about 25% of the thicknesses of the first nonwoven. In general, the portion of the second nonwoven web that forms the interface is an exterior surface of the second nonwoven web. In embodiments, the interface comprises 75% or less, 70% or less, 60% or less, 50% or less, 40% or less, 30% or less, 25% or less, 20% or less, or 15% or less of the thickness of the second nonwoven web. In embodiments, the first interface comprises at least 1%, at least 5%, at least 10%, at least 20%, at least 25%, at least 30%, or at least 40% of the thickness of the second nonwoven web. In embodiments, the first interface comprises from about 1% to about 75% of the thickness of the second nonwoven web.

As used herein, and unless specified otherwise, two layers of nonwoven webs are "fused" if at least a portion of the fibers from each web are bonded to fibers from the other web. As described herein, bonding of the fibers includes entangling of the fibers. The two layers of nonwoven webs can be fused using any suitable method. In embodiments, the portion of the first nonwoven web and the portion of the second nonwoven web are thermally fused, solvent fused, or both. In embodiments, the portion of the first nonwoven web and the portion of the second nonwoven web are thermally fused. Thermal fusion can include the use of heat and/or pressure. In embodiments, one or both of two discrete nonwoven webs can be heated until the fibers are soft and the webs can then be pressed together such that when the fibers cool at least a portion of fibers from each web are bonded to at least a portion of fibers from the other web. In embodiments, one or both of the first and second nonwoven webs can be melt-spun and applied in an inline process such that heated, soft fibers are applied directly to a pre-formed nonwoven web after passing through the die assembly and fuse to the fibers of the pre-formed nonwoven forming a fused interface. In embodiments, the portion of the first nonwoven web and the portion of the second nonwoven web are solvent fused. Solvent fusion can include the application of a binder solution to one or both of the nonwoven webs followed by contacting the nonwoven webs such that upon drying, at least a portion of fibers from each web are bonded to at least a portion of fibers from the other web. Solvent fusion can occur as a discrete process including two discrete pre-formed webs or can be an inline process wherein a binder solution is applied to a pre-formed nonwoven web and a second nonwoven web is formed on the pre-formed nonwoven web in a continuous process. The binder solution for solvent fusion of the nonwoven web can be any binder solution described herein for binding. As used herein, and unless specified otherwise, a "pre-formed nonwoven web" encompasses nonwoven webs formed but not bonded and nonwoven webs that have been formed and bonded. As used herein, and unless specified otherwise, a "discrete nonwoven web" encompasses nonwoven webs formed by carding or airlaying staple fibers, or by continuous processes, and the nonwoven webs may or may not be bonded. In embodiments, the fusing of two nonwoven webs can also be used to bond one or both of the nonwoven webs.

In embodiments, the first interface is solvent fused and the solvent is selected from the group consisting of water, ethanol, methanol, DMSO, glycerin, and a combination thereof. In embodiments, the first interface is solvent fused and the solvent is selected from the group consisting of water, glycerin, and a combination thereof. In embodiments, the first interface is solvent fused using a binder solution comprising polyvinyl alcohol and water, glycerin, or a combination thereof. In embodiments, the first interface is solvent fused using a binder solution comprising polyvinyl alcohol, latex, or a combination thereof and water, glycerin, or a combination thereof.

As used herein, and unless specified otherwise, a first type of fiber has a diameter that is "smaller than" the diameter of a second type of fiber if the average fiber diameter for the first type of fiber is less than the average fiber diameter of the second type of fiber. For example, the first type of fiber can have an overlapping diameter size distribution with the second type of fiber and still have a smaller diameter as long as the average fiber diameter for the first type of fiber is smaller than the average fiber diameter of the second type of fiber. In embodiments, the smaller fiber type has an average fiber diameter that is smaller than the smallest diameter of the diameter size distribution of the larger fiber type. A difference in diameter is present if the difference can be visualized using projection microscope imaging as outlined in SO137:2015. In embodiments, the difference in diameter between the smaller fiber type and the larger fiber type can be submicron, for example, if multiple melt-spun layers are used. In embodiments, the difference in the diameter between the smaller fiber type and the larger fiber type can be about 1 micron to about 300 micron, about 5 micron to about 300 micron, about 5 micron to about 250 micron, about 5 micron to about 200 micron, about 10 micron to about 150 micron, about 10 micron to about 100 micron, about 10 micron to about 90 micron, about 15 micron to about 80 micron, about 15 micron to about 70 micron, about 20 micron to about 60 micron, about 20 micron to about 50 micron, or about 25 micron to about 45 micron. In embodiments, the difference in diameter between the smaller fiber type and the larger fiber type can be about 5 micron to about 75 micron. In embodiments, the difference in diameter between the smaller fiber type and the larger fiber type can be about 20 micron to about 80 micron. Without intending to be bound by theory, it is believed that providing a composite of two nonwoven webs wherein the nonwoven webs are fused and the second nonwoven web has a fiber diameter that is smaller than the first nonwoven web advantageously can improve the adsorption/absorption rate and fluid capacity of the composite article, direct adsorption/absorption from larger diameter fibers to smaller diameter fibers to move the fluid preferentially; increase the surface to volume ratio of a nonwoven composite article as compared to single diameter materials resulting in increased loading capacity, and/or improved dispersion and/or total dissolution of the nonwoven composite article as compared to a nonwoven having a single diameter material. The average diameters of the fibers in the individual web layers can be any diameters provided herein. In embodiments, the first plurality of fibers in the first layer of first nonwoven can have a diameter of about 10 micron to about 300 micron, about 50 micron to about 300 micron, or about greater than about 100 micron to about 300 micron. In embodiments, the first plurality of fibers can have an average diameter of greater than about 100 micron to about 300 micron. In embodiments wherein a nonwoven layer of the nonwoven composite material includes a blend of fiber types having different diameters, if the distribution of fiber diameters is monomodal, the average fiber diameter refers to the average fiber diameter of the blend. The blend of fiber types can have distribution of fiber diameters in the nonwoven layer that bimodal or higher. When a blend of fibers has a bimodal or higher-modal diameter distribution, a fiber has a smaller diameter than the fibers of said blend when the fiber has an average fiber diameter less than the average for the distribution of the smallest diameter fibers of the blend, and a fiber is larger than the fibers of said blend when the fiber has an average fiber diameter that is greater than the average for the distribution of the larger diameter fibers of the blend.

In embodiments, the composite article further comprises a third layer of a third nonwoven web comprising a third plurality of fibers. In embodiments wherein the nonwoven composite article includes a third layer of a third nonwoven web, the second layer can be provided between the first layer and the third layer and at least a second portion of the second nonwoven web and at least a portion of the third nonwoven web can be fused, providing a second interface. The second interface including at least a second portion of the second nonwoven web and at least a portion of the third nonwoven web is the area of the composite where the second and third nonwoven webs overlap and the second plurality of fibers and the third plurality of fibers are intermingled. In some embodiments, and depending on the thickness of the second layer of second nonwoven web, the first plurality of fibers and the third plurality of fibers may become intermingled and/or fused such that there is no clear delineation between the first interface and the second interface. In general, the portion of the second nonwoven web that forms the second interface is an exterior surface of the second nonwoven web opposite from the exterior surface of the second nonwoven web fused to the first nonwoven web. In embodiments, the second interface comprises 75% or less, 70% or less, 60% or less, 50% or less, 40% or less, 30% or less, 25% or less, 20% or less, or 15% or less of the thickness of the second nonwoven web. In embodiments, the second interface comprises at least 1%, at least 5%, at least 10%, at least 20%, at least 25%, at least 30%, or at least 40% of the thickness of the second nonwoven web. In embodiments, the second interface comprises from about 1% to about 75% of the thickness of the second nonwoven web. In embodiments, the portion of the third nonwoven web that forms the second interface is an exterior surface of the third nonwoven web. In embodiments, the second interface comprises 50% or less of the thickness of the third nonwoven web, 40% or less, 30% or less, 25% or less, 20% or less, 10% or less, 5% or less, 2.5% or less, or 1% or less of the thickness of the first nonwoven web. In embodiments, the second interface comprises at least 0.1%, at least 0.5%, at least 1%, or at least 5% of the thickness of the third nonwoven. In embodiments, the second interface comprises about 0.1% to about 25% of the thicknesses of the third nonwoven.

In embodiments, the second portion of the second nonwoven web and the portion of the third nonwoven web are thermally fused, solvent fused, or both. In embodiments, the second portion of the second nonwoven web and the portion of the third nonwoven web are thermally fused. In embodiments, the second portion of the second nonwoven web and the portion of the third nonwoven web are solvent fused.

In embodiments, the second interface is solvent fused and the solvent is selected from the group consisting of water, ethanol, methanol, DMSO, glycerin, and a combination thereof. In embodiments, the second interface is solvent fused and the solvent is selected from the group consisting of water, glycerin, and a combination thereof. In embodiments, the second interface is solvent fused using a binder solution comprising polyvinyl alcohol and water, glycerin, or a combination thereof. In embodiments, the second interface is solvent fused using a binder solution comprising polyvinyl alcohol, latex, or a combination thereof and water, glycerin, or a combination thereof.

In embodiments, the first layer of first nonwoven web and the second layer of second nonwoven web have different porosities. As used herein, and unless specified otherwise, two nonwoven webs have "different porosities" when the difference in porosities of the nonwoven web is at least about 1%. In embodiments, the difference in porosities between two layers of nonwoven webs in the composite articles can be about 1% to about 20%. For example, one layer of nonwoven web in a composite article can have a porosity of about 80% and a second layer of nonwoven web in the composite article can have a porosity of about 85%, a 5% difference in porosity. In embodiments, the porosity of the second nonwoven web is less than the porosity of the first nonwoven web. In embodiments, the porosity of the second nonwoven web is the same as the porosity of the first nonwoven web. As used herein, and unless specified otherwise, two nonwoven webs have the "same porosity" if the difference in porosity values between the two nonwoven webs is less than 1%.

In embodiments wherein the composite article comprises a third layer of a third nonwoven web, the third nonwoven web can have a porosity that is the same or different from the first nonwoven web. In embodiments, the third nonwoven web can have the same porosity as the first nonwoven web. In embodiments, the third nonwoven web can have a different porosity than the first nonwoven web. In embodiments, the third nonwoven web can be less porous than the first nonwoven web. In embodiments, the third nonwoven web can have the same porosity as the second nonwoven web. In embodiments, the third nonwoven web can have a different porosity than the second nonwoven web. In embodiments, the third nonwoven web can be less porous than the second nonwoven web. In embodiments, the second nonwoven web can be less porous than the first nonwoven web and the third nonwoven web can be less porous than the second nonwoven web. In embodiments, the nonwoven composite article can have a gradient of porosity between the layers of nonwoven web, wherein one exterior surface of the composite structure can have the largest porosity and the other exterior surface of the composite structure can have the smallest porosity. In embodiments, the composite structure can have a gradient of porosity between the layers of nonwoven web, wherein the exterior surfaces of the composite structure can have the largest porosity and the middle layer(s) of the composite structure can have the smallest porosity. In embodiments, the composite structure can include a fourth or higher layer of nonwoven webs such that a middle layer(s) can include the second and third layers of nonwoven webs (for a four-layer composite structure), or the third layer of nonwoven web (for a five layer composite structure).

Without intending to be bound by theory, it is believed that when the porosity of the composite structure comprises a gradient, the composite structure advantageously has enhanced wicking of liquid from the more porous exterior surface to the less porous exterior surface or less porous middle layer(s).

The plurality of fibers in any given nonwoven layer of the composite article can be any of the fibers disclosed herein, and can be the same or different. In embodiments, the composition of the fiber forming materials in the first plurality, second plurality, and third plurality of fibers can be the same or different, for example, having any difference in diameter, length, tenacity, shape, rigidity, elasticity, solubility, melting point, glass transition temperature ($T_g$), fiber forming material, color, or a combination thereof. The following table demonstrates contemplated composite articles where the nonwoven layers can include fibers having three different fiber compositions, wherein each letter "A", "B", and "C" refers to a specific fiber composition and "-" means that the contemplated composite article does not include a third layer of nonwoven web. Each of the fiber compositions A, B, and C can be (a) a single fiber type including a single fiber forming material, (b) a single fiber type including a blend of fiber forming materials, (c) a blend of fiber types, each fiber type including a single fiber forming material, (d) a blend of fiber types, each fiber type including a blend of fiber forming materials, or (e) a blend of fiber types, each fiber type including a single fiber forming material or a blend of fiber forming materials.

TABLE 1

| | Composite 1 | Composite 2 | Composite 3 | Composite 4 | Composite 5 | Composite 6 | Composite 7 | Composite 8 | Composite 9 |
|---|---|---|---|---|---|---|---|---|---|
| 1st plurality | A | A | A | B | B | B | C | C | C |
| 2nd plurality | A | B | C | A | B | C | A | B | C |
| 3rd plurality | — | — | — | — | — | — | — | — | — |

| | Composite 10 | Composite 11 | Composite 12 | Composite 13 | Composite 14 | Composite 15 | Composite 16 | Composite 17 | Composite 18 |
|---|---|---|---|---|---|---|---|---|---|
| 1st plurality | A | A | A | A | A | A | A | A | A |
| 2nd plurality | A | A | A | B | B | B | C | C | C |
| 3rd plurality | A | B | C | A | B | C | A | B | C |

| | Composite 19 | Composite 20 | Composite 21 | Composite 22 | Composite 23 | Composite 24 | Composite 25 | Composite 26 | Composite 27 |
|---|---|---|---|---|---|---|---|---|---|
| 1st plurality | B | B | B | B | B | B | B | B | B |
| 2nd plurality | A | A | A | B | B | B | C | C | C |
| 3rd plurality | A | B | C | A | B | C | A | B | C |

| | Composite 28 | Composite 29 | Composite 30 | Composite 31 | Composite 32 | Composite 33 | Composite 34 | Composite 35 | Composite 36 |
|---|---|---|---|---|---|---|---|---|---|
| 1st plurality | C | C | C | C | C | C | C | C | C |
| 2nd plurality | A | A | A | B | B | B | C | C | C |
| 3rd plurality | A | B | C | A | B | C | A | B | C |

In embodiments, the first plurality of fibers includes water-soluble polyvinyl alcohol (PVOH) fiber forming material. As described herein, the term "the PVOH fiber" is understood to include a fiber comprising a homopolymer, a copolymer, or a modified copolymer comprising vinyl alcohol moieties, for example, 50% or higher of vinyl alcohol moieties, and a fiber comprising such a polymer chemically modified with a modification agent. The chemically modified fiber may comprise no vinyl alcohol moieties or less than 50% of vinyl alcohol moieties. In embodiments, the second plurality of fibers includes water-soluble polyvinyl alcohol fiber forming material. In embodiments, the first plurality of fibers and the second plurality of fibers include water-soluble polyvinyl alcohol fiber forming material. In embodiments including a third layer of nonwoven web having a third plurality of fibers, the third plurality of fibers can include a water-soluble polyvinyl alcohol fiber forming material. In embodiments, the polyvinyl alcohol fiber forming material can be present in one or more fiber types in the plurality of fibers. The water-soluble polyvinyl alcohol fiber forming materials of any of the first plurality, second plurality, or third plurality of fibers can be any water-soluble polyvinyl alcohol fiber forming material disclosed herein. In embodiments wherein two or more of the first plurality of fibers, the second plurality of fibers, and/or the third plurality of fibers include a polyvinyl alcohol fiber forming material, the polyvinyl alcohol can be the same or different in each plurality, can be the sole fiber forming material or part of blend of fiber forming material in each plurality, and if each plurality includes a different polyvinyl alcohol fiber, the difference can be in length to diameter ratio (L/D), tenacity, shape, rigidity, elasticity, solubility, melting point, glass transition temperature ($T_g$), fiber chemistry, color, or a combination thereof.

In embodiments, the fibers of the first plurality of fibers, the second plurality of fibers, and/or third plurality of fibers can include a fiber forming material other than a polyvinyl alcohol fiber forming material.

In embodiments, the first nonwoven web has a tenacity ratio (MD:CD) of about 0.5 to about 1.5. In embodiments, the first nonwoven web has a MD:CD of about 0.8 to about 1.25. In embodiments, the first nonwoven web has a MD:CD of about 0.9 to about 1.1. In embodiments, the second nonwoven web has a tenacity ratio (MD:CD) of about 0.5 to about 1.5. In embodiments, the second nonwoven web has a MD:CD of about 0.8 to about 1.25. In embodiments, the second nonwoven web has a MD:CD of about 0.9 to about 1.1. In embodiments, the third nonwoven web has a tenacity ratio (MD:CD) of about 0.5 to about 1.5. In embodiments, the third nonwoven web has a MD:CD of about 0.8 to about 1.25. In embodiments, the third nonwoven web has a MD:CD of about 0.9 to about 1.1. In embodiments, the nonwoven composite article has a tenacity ratio (MD:CD) in a range of about 0.5 to about 1.5, about 0.8 to about 1.25, about 0.9 to about 1.1, or about 0.95 to about 1.05. In embodiments, the nonwoven composite article has a MD:CD of about 0.8 to about 1.5. In embodiments, the nonwoven composite article has a MD:CD of about 0.9 to 1.1. The MD:CD of the nonwoven composite article is related to the MD:CD ratio of each individual of layer of nonwoven web present in the composite article. Without intending to be bound by theory, it is believed that the MD:CD of the composite article cannot be determined by considering the MD and CD of each layer of nonwoven web individually, but the MD and CD of the nonwoven composite article must be measured. Without intending to be bound by theory, it is believed that as the tenacity ratio MD:CD of the nonwoven composite article approaches 1, the durability of the composite article is increased, providing superior resistance to breakdown of the nonwoven when stress is applied to the nonwoven during use. Further, without intending to be bound by theory, it is believed that the MD:CD ratio of a composite article including at least one layer of a melt-spun nonwoven web will have an MD:CD ratio closer to 1:1 than an identical composite article except including all carded layers.

The basis weights of the nonwoven composite articles of the disclosure are not particularly limiting and can be in a range of about 5 g/m² to about 150 g/m², about 5 g/m² to about 125 g/m², about 5 g/m² to about 100 g/m², about 5 g/m² to about 70 g/m², about 5 g/m² to about 50 g/m², about 5 g/m² to about 30 g/m². In embodiments, the nonwoven composite articles of the disclosure can have a basis weight of about 5 g/m² to about 50 g/m². In embodiments, the nonwoven composite articles of the disclosure can have a basis weight of about 50 g/m² to about 150 g/m². In embodiments, the first layer of nonwoven web can have a basis weight of about 30 g/m² to about 70 g/m² and the nonwoven composite article can have a basis weight of about 60 g/m² to about 150 g/m². In embodiments, the first layer of nonwoven web can have a basis weight of about 5 g/m² to about 15 g/m². In embodiments, the first layer of nonwoven web can have a basis weight of about 5 g/m² to about 15 g/m² and the nonwoven composite article can have a basis weight in a range of about 15 g/m² to about 50 g/m². In embodiments, the third layer of nonwoven web can have a basis weight of about 5 g/m² to about 15 g/m². In embodiments, the first layer of nonwoven web can have a basis weight of about 5 g/m² to about 15 g/m² and the third layer of nonwoven web can have a basis weight of about 5 g/m² to about 15 g/m². In embodiments, the second layer of nonwoven web can be included in the composite article in about 2.5 wt. % to about 10 wt. %, based on the total weight of the composite article. In embodiments, the second layer of nonwoven web can be included in the composite article in about 2.5 wt. % to about 10 wt. %, based on the total weight of the composite article and the first layer of nonwoven web can be included in the composite article in about 90 wt. % to about 97.5 wt. %, based on the total weight of the composite article. In embodiments, the second layer of nonwoven web can be included in the composite article in about 2.5 wt. % to about 10 wt. %, based on the total weight of the composite article and the first layer of nonwoven web and the third layer of nonwoven web together are included in an about 90 wt. % to about 97.5 wt. %, based on the total weight of the composite article. In embodiments, the third layer of nonwoven web can be included in the composite article in about 2.5 wt. % to about 10 wt. %, based on the total weight of the composite article and the first layer of nonwoven web and second layer of nonwoven web together are included in about 45 wt. % to about 48 wt. %, based on the total weight of the composite article.

In embodiments, the fiber diameters of the first plurality of fibers can be substantially uniform. In embodiments, the fiber diameters of the second plurality of fibers can be substantially uniform. In embodiments, the fiber diameters of the third plurality of fibers can be substantially uniform. In embodiments, the fiber diameters of the first plurality of fibers and third plurality of fibers can be substantially uniform. In embodiments, the fiber diameters of each of the first plurality of fibers, second plurality of fibers, and third plurality of fibers can be substantially uniform.

In embodiments, the nonwoven composite article can have an improved modulus, tensile strength, elongation, tenacity, or a combination thereof in the machine direction, cross direction, or both, relative to an identical article comprising only the first layer. In embodiments, the nonwoven composite article can have an improved modulus, tensile strength, elongation, tenacity, or a combination thereof in the machine direction, relative to an identical article comprising only the first layer. In embodiments, the nonwoven composite article can have an improved modulus, tensile strength, elongation, or a combination thereof in the cross direction, relative to an identical article comprising only the first layer. In embodiments, the nonwoven composite article can have an improved modulus, tensile strength, elongation, tenacity or a combination thereof in the machine direction and the cross direction, relative to an identical article comprising only the first layer.

Methods of Preparing Composite Articles

The composite articles can be made using any process known in the art suitable for combining two or more layers of nonwoven webs such that at least a portion of the first layer and a portion of the second layer are fused, thereby forming an interface.

In embodiments, the method of forming the nonwoven composite articles of the disclosure can include the steps of: (a) depositing on a first layer including a first nonwoven web, a second layer comprising a second nonwoven web under conditions sufficient to fuse at least a portion of the first nonwoven web to at least a portion of the second nonwoven web, thereby forming a first interface; and (b) optionally, depositing on the second layer comprising the second nonwoven web, the third layer comprising the third nonwoven web under conditions sufficient to fuse at least a second portion of the second nonwoven web to at least a portion of the third nonwoven web, thereby forming a second interface.

In embodiments, steps (a) and (b) can be repeated to include additional nonwoven layers to the composite structure, e.g., a fourth nonwoven layer, a fifth nonwoven layer, etc.

The conditions sufficient to fuse at least a portion of the first nonwoven web to at least a portion of the second nonwoven web and/or to fuse at least a second portion of the second nonwoven web to at least a portion of the third nonwoven web can include thermal fusion and/or solvent fusion, as described herein.

In embodiments of the foregoing methods, the first layer can comprise a carded nonwoven web. In embodiments of the foregoing methods, the third layer can comprise a carded nonwoven web or a melt-spun nonwoven web. In embodiments of the foregoing methods, the second layer can include a melt-spun nonwoven web or an airlaid nonwoven web. In embodiments, the first layer can include a carded nonwoven web, the second layer can include a melt-spun nonwoven web, and the third layer can include a carded nonwoven web. In embodiments, the first layer can include a carded nonwoven web, the second layer can include a melt blown nonwoven web, and the third layer can include a carded nonwoven web. In embodiments, the second layer can include an airlaid nonwoven web. In embodiments, the first layer can include a carded nonwoven web, the second layer can include an airlaid nonwoven web, and the third layer can include a melt-spun nonwoven web. In embodiments, the first layer can include a carded nonwoven web, the second layer can include an airlaid nonwoven web, and the third layer can include a melt blown nonwoven web. In embodiments, the nonwoven composite article can include five layers of nonwoven web wherein the first layer can include a carded nonwoven web, the second layer can include an airlaid nonwoven web, the third layer can include a melt-spun nonwoven web, the fourth layer can include an airlaid nonwoven web, and the fifth layer can include a carded nonwoven web. In embodiments, the nonwoven composite article can include five layers of nonwoven web wherein the first layer can include a carded nonwoven web, the second layer can include an airlaid nonwoven web, the third layer can include a melt blown nonwoven web, the fourth layer can include an airlaid nonwoven web, and the fifth layer can include a carded nonwoven web. In embodiments, the second nonwoven web can include a cellulose fiber forming material.

Flushable Wipes

Flushable wipes of the disclosure can include a nonwoven web of the disclosure and/or a composite article according to the disclosure.

Flushable wipes can include a plurality of fibers of the disclosure, wherein the plurality of fibers can include water-soluble fibers and, optionally, water-insoluble fibers.

In embodiments wherein the flushable wipe includes a nonwoven web comprising water-soluble fibers and water-insoluble fibers, the ratio of water-insoluble fiber to water-soluble fiber can range from about 1:18 to about 4:1, about 1:10 to about 3:1, about 1:5 to about 2:1, or about 1:2 to about 2:1, for example about 1:18, 1:16, 1:14, 1:12, 1:10, 1:5, 1:3, 1:2, 1:1, 2:1, 3:1, or 4:1.

The flushable wipes of the disclosure can include a cleaning lotion. Flushable wipes of the disclosure generally include fibers having a surface energy that is high enough to allow the fibers to be readily wet by the cleaning lotion during the wetting step of the wipe manufacturing process. Thus, in embodiments, at least a portion of at least one exterior layer of the nonwoven composite article of the flushable wipe includes a hydrophilic fiber. In embodiments, at least a portion of each exterior layer of the nonwoven composite article used to prepare the flushable wipe includes a hydrophilic fiber. As used herein, and unless specified otherwise, a "hydrophilic fiber" refers to any fiber having a surface thereof that is hydrophilic. A fiber can have a hydrophilic surface when the fiber includes, for example, a hydrophilic fiber forming material, the fiber is a core-sheath type bicomponent fiber including a hydrophilic fiber forming material in the sheath, and/or the fiber has been surface treated to include a hydrophilic material on the surface thereof. Without intending to be bound by theory, it is believed that a hydrophilic fiber of a nonwoven can facilitate capillary action/wicking of a liquid from a surface of the nonwoven, providing improved liquid acquisition relative to an identical nonwoven that does not include a hydrophilic fiber.

Non-limiting examples of applications for wipes include cleaning surfaces, cleaning skin, automotive uses, baby care, feminine care, hair cleansing, and removing or applying makeup, skin conditioners, ointments, sun-screens, insect repellents, medications, varnishes or industrial and institutional cleaning.

Lotion Composition

The flushable wipes of the disclosure can comprise a lotion composition to wet a substrate to facilitate cleaning. In embodiments wherein the flushable wipe is a personal care wipe, the lotion composition may also include ingredients to soothe, soften, or care for the skin, to improve the feel of the lotion, to improve the removal of residues from the skin, to provide pleasant scents, and/or to prevent bacterial growth, for example.

Lotion compositions can have a pH at or near about 5.5, close to the physiological skin pH. Low pH lotion compositions can have a pH at or near about 3.8 and can be useful in cases where a wipe is being used to remove alkaline residues, such as residues from fecal matter, and help restore a healthy acidic skin pH of approximately 5 and/or render irritants from fecal matter non-irritating, as by inactivating fecal enzymes. Low pH lotions may also inhibit microbial growth. In embodiments wherein the pH of the lotion composition is about 4 or less, the fibers of the first plurality of fibers, second plurality of fibers, and/or third plurality of fibers can include a polyvinyl alcohol copolymer. The copolymer can be provided as the sole fiber forming material in a fiber of a fiber blend or as one component of a fiber forming material in a fiber including a blend of fiber forming materials. In refinements of the foregoing embodiment, the fibers can include a blend of polyvinyl alcohol copolymers and homopolymers. The polyvinyl alcohol copolymers and homopolymers can be provided in a ratio of about 1:1 to about 4:1. In further refinements of the foregoing embodiments, the polyvinyl alcohol copolymer containing fibers can be blended with non-water-soluble fibers. Either or both of the polyvinyl copolymers and homopolymers may be chemically modified with a modification agent as described herein.

Lotion compositions can comprise a superwetter, a rheology modifier, an emollient and/or an emulsifier. The superwetter can be present in an amount of about 0.01% to 0.2% by weight of the superwetter to the total weight of the lotion composition. The superwetter can be selected from the group consisting of trisiloxanes, polyether dimethicones wherein the polyether functionality is PEG, PPG, or a mixture thereof, and a mixture of the foregoing.

The rheology modifier can be present in an amount of about 0.01% to 0.5% by weight of the rheology based on the total weight of the lotion composition. The rheology modifier can be selected from the group consisting of xanthan gum, modified xanthan gum, and a combination thereof.

The emollient, if present, may be a thickening emollient. Suitable emollients include, but are not limited to, PEG-10 sunflower oil glycerides, sunflower oil, palm oil, olive oil, emu oil, babassu oil, evening primrose oil, palm kernel oil, cod liver oil, cottonseed oil, jojoba oil, meadowfoam seed oil, sweet almond oil, canola oil, soybean oil, avocado oil, safflower oil, coconut oil, sesame oil, rice bran oil, grape seen oil, mineral oil, isopropyl stearate, isostearyl isononanoate, diethylhexyl fumarate, diisostearyl malate, triisocetyl citrate, stearyl stearate, methyl palmitate, methylheptyl isostearate, petrolatum, lanolin oil and lanolin wax, long chain alcohols like cetyl alcohol, stearyl alcohol, behenyl alcohol, isostearyl alcohol, and 2-hexyl-decanol, myristyl alcohol, dimethicone fluids of various molecular weights and mixtures thereof, PPG-15 stearyl ether (also known as arlatone E), shea butter, olive butter, sunflower butter, coconut butter, jojoba butter, cocoa butter, squalene and squalene, isoparaffins, polyethylene glycols of various molecular weights, polypropylene glycols of various molecular weights, or mixtures thereof.

The emulsifier, if present, may be solid at room temperature. Suitable emulsifiers include, but are not limited to, laureth-23, ceteth-2, ceteth-10, ceteth-20, ceteth-21, ceteareth-20, steareth-2, steareth-10, steareth-20, oleth-2, oleth-10, oleth-20, steareth-100, steareth-21, PEG-40 sorbitan peroleate, PEG-8 stearate, PEG-40 stearate, PEG-50 stearate, PEG-100 stearate, sorbitan laurate, sorbitan palmitate, sorbitan stearate, sorbitan tristearate, sorbitan oleate, sorbitan trioleate, polysorbate 20, polysorbate 21, polysorbate 40, polysorbate 60, polysorbate 61, polysorbate 65, polysorbate 80, polysorbate 81, polysorbate 85, PEG-40 hydrogenated castor oil, citric acid ester, microcrystalline wax, paraffin wax, beeswax, carnauba wax, ozokerite wax, cetyl alcohol, stearyl alcohol, cetearyl alcohol, myristyl alcohol, behenyl alcohol, and mixtures thereof.

In embodiments, the cleaning lotion includes an aqueous emulsion including an emollient and an emulsifier.

The cleaning lotion can further comprise humectants including, but not limited to glycerin, propylene glycol, and phospholipids; fragrances such as essential oils and perfumes as described herein; preservatives; enzymes; colorants; oil absorbers; pesticides; fertilizer; activators; acid catalysts; metal catalyst; ion scavengers; detergents; disinfectants; surfactants; bleaches; bleach components; and fabric softeners. In embodiments, the cleaning lotion includes a fragrance, preservative, enzyme, colorant, oil absorber, pesticide, ion scavenger, detergent, disinfectant, or a combination thereof.

Preservatives prevent the growth of micro-organisms in the liquid lotion, the flushable wipe, and/or the substrate on which the wipe is used. Preservatives can be hydrophobic or hydrophilic. Suitable preservatives include, but are not limited to parabens, such as methyl parabens, propyl parabens, alkyl glycinates, iodine derivatives and combinations thereof.

The lotion load can be between 150% and 480%. As used herein, "load" refers to combining a nonwoven web or composite article with a lotion composition, i.e., a lotion composition is loaded onto or into a nonwoven web or composite article, without regard to the method used to combine the nonwoven web or composite article with the lotion composition, i.e., immersion, spraying, kissrolling, etc. A "lotion load" refers to the amount of lotion loaded onto or into a nonwoven web or composite article, and is expressed as weight of the lotion to weight of the dry (unloaded) nonwoven web or composite article, as a percentage. It may be desirable for the flushable wipe to be loaded with lotion to a degree that some of the lotion can be easily transferred to a substrate (e.g., skin or another surface to be cleaned) during use. The transfer may facilitate cleaning, provide a pleasant sensation for a user (such as a smooth skin feeling or coolness from evaporation), and/or allow for the transfer of compounds to provide beneficial functions on substrate.

The flushable wipes can be nonwoven webs or composite articles having a high density of interstitial spaces between the fibers making up the wipe. In order to maintain enough lotion available on the surface of a wipe to transfer to the substrate, much of the interstitial space in the wipe can be filled with lotion. The lotion in the interstitial space may not be readily available for transfer to a substrate, such that excess lotion can be loaded into the wipe in an amount sufficient to signal to the user that the lotion is available for transfer to a substrate, for example, by providing an adequate sense of wetness. Advantageously, nonwoven composite articles used in the flushable wipes can have a gradient of porosity as described herein, which can facilitate loading of the lotion to the wipe.

The flushable wipe can be made by wetting a nonwoven web or composite article with at least 1 gram of liquid cleaning lotion per gram of dry fibrous composite. Suitable methods of delivering the cleaning lotion to the nonwoven web or composite article include but are not limited to submersion, spraying, padding, extrusion coating and dip coating. After wetting, the wetted composite article can be folded, stacked, cut to length, and packaged as desired. The flushable wipes are generally of sufficient dimension to allow for a convenient handling while being small enough to be easily disposed to the sewage system. The wetted composite article can be cut or folded to such dimensions during the manufacturing process or can be larger in size and having a means such as perforations to allow individual wipes to be separated from the web, in a desired size, by a user.

In embodiments, the flushable wipes of the disclosure comprise a nonwoven web of the disclosure and a cleaning lotion. In embodiments, the flushable wipes of the disclosure comprise a nonwoven composite article of the disclosure and a cleaning lotion. In embodiments, the flushable wipes of the disclosure consist of a nonwoven composite article of the disclosure and a cleaning lotion.

Absorbent Articles

The nonwoven webs and nonwoven composite articles of the disclosure can be used as a liquid acquisition layer for absorbent articles. The absorbent articles can include bibs, breast pads, care mats, cleaning pads (e.g., floor cleaning pads), diapers, diaper pants, incontinence liners, pads, and other articles (e.g., adult incontinence diapers, adult incontinence pads, adult incontinence pants, potty training liners, potty training pads, potty training pants, and pet training pads e.g., puppy pads), interlabial devices, menstrual pads, panty liners, sanitary napkins, tampons, spill absorbing mats, spill absorbing pads, spill absorbing rolls, wound dressings, and the like. In one aspect, any of the foregoing articles can be disposable items. The term "disposable" refers to articles that are designed or intended to be discarded after a single use. That is, disposable articles are not intended to be laundered or otherwise restored or reused, and in embodiments may be incapable of laundering, restoration or reuse.

As used herein, the term "absorbent article" includes articles that absorb and contain liquids such as body exudates. The term "absorbent article" is intended to include diapers, incontinent articles, sanitary napkins, and the like. The term "incontinent articles" is intended to include pads, undergarments (pads held in place by a suspension system of some type, such as a belt, or the like), inserts for absorbent articles, capacity boosters for absorbent articles, briefs, bed pads, and the like, regardless of whether they be worn by adults or other incontinent persons. At least some of such absorbent articles are intended for the absorption of body liquids, such as menses or blood, vaginal discharges, urine, sweat, breast milk, and fecal matter.

As used herein "diapers" refers to devices that are intended to be placed against the skin of a wearer to absorb and contain the various exudates discharged from the body. Diapers are generally worn by infants and incontinent persons about the lower torso so as to encircle the waist and legs of the wearer. Examples of diapers include infant or adult diapers and pant-like diapers such as training pants. "Training pant", as used herein, refers to disposable garments having a waist opening and leg openings designed for infant or adult wearers. A pant may be placed in position on the wearer by inserting the wearer's legs into the leg openings and sliding the pant into position about a wearer's lower torso. A pant may be pre-formed by any suitable technique including, but not limited to, joining together portions of the article using refastenable and/or non-refastenable bonds (e.g., seam, weld, adhesive, cohesive bond, fastener, etc.). A pant may be pre-formed anywhere along the circumference of the article (e.g., side fastened, front waist fastened).

In embodiments, absorbent articles of the disclosure comprise a liquid pervious topsheet, a liquid impervious backsheet joined to the topsheet, and a liquid acquisition layer and an absorbent core between the topsheet and backsheet. In embodiments wherein the absorbent article is a wearable article (e.g., incontinent articles, sanitary napkins, and the like), the article can have a wearer facing side and an outer facing side. In general, the liquid pervious topsheet is on the wearer facing side and the liquid impervious backsheet is on the outer facing side of the absorbent article. The absorbent core is generally a sheet like structure and, when provided as a wearable, has a wearer facing side and an outer facing side.

The liquid pervious topsheet can be any liquid pervious topsheet known in the art. For a wearable article, the topsheet can be fully or partially elasticized or can be foreshortened to provide a void space between the topsheet and the absorbent core. The liquid impervious backsheet can be any liquid impervious backsheet known in the art. The backsheet prevents exudates absorbed by the absorbent core and contained within the article form contacting any substrate the absorbent article may be in contact with. The backsheet can be impervious to liquids and include a laminate of a nonwoven and a thin plastic film, such as a thermoplastic film. Suitable backsheet films include those manufactured by Tredegar Industries Inc. of Terre Haute, Ind. and sold under the trade names X15306, X10962, and X10964. Other suitable backsheet materials can include breathable materials that permit vapors to escape from the absorbent article, while still preventing liquid from passing through the backsheet. Exemplary breathable materials can include materials such as woven webs, nonwoven webs, and composite materials such as manufactured by Mitsui Toatsu Col, of Japan under the designation ESPOIR NO and by EXXON Chemical Co., of Bay City, Tex., under the designation EXXAIRE.

The absorbent core is disposed between the topsheet and the backsheet. The absorbent core can comprise any absorbent material that is capable of absorbing and retaining liquids such as urine and other body exudates. The absorbent core can include a wide variety of liquid-absorbent materials commonly used in disposable diapers and other absorbent articles such as super absorbent polymer, comminuted wood pulp (air felt), creped cellulose wadding; absorbent foams, absorbent sponges, absorbent gelling materials, or any other known absorbent material or combinations of materials. The absorbent core can include minor amounts (less than about 10%) of non-liquid absorbent materials, such as adhesives, waxes, oils and the like.

The liquid acquisition layer includes a nonwoven web of the disclosure including a plurality of fibers including a water-soluble polyvinyl alcohol fiber forming material as described herein. The plurality of fibers can include a single fiber type or a blend of fiber types, and the fibers can include a sole polyvinyl alcohol fiber forming material or a blend of fiber forming materials including a polyvinyl alcohol fiber forming material. The fibers can comprise fibers chemically modified with a modification agent as described herein.

In embodiments, the liquid acquisition layer can be provided between the absorbent core and the topsheet. In wearable embodiments, the liquid acquisition layer can be provided on the wearer facing side of the absorbed core. In embodiments, the liquid acquisition layer can be provided between the absorbent core and the backsheet. In wearable embodiments, the liquid acquisition layer can be provided on the outer facing side of the absorbent core. In embodiments, the liquid acquisition layer is wrapped around the absorbent core. The liquid acquisition layer can be a single sheet that is wrapped around the absorbent core or can be provided as two individual layers that are joined. Without intending to be bound by theory, it is believed that by including the liquid acquisition layer between the absorbent core and the backsheet or on the outer facing side of the absorbent core advantageously prevents leakage of the liquid from the absorbent article by providing additional liquid acquisition material to catch any overflow of liquid from the topsheet side and/or wearer facing side.

The liquid acquisition layer can be directly in contact with the absorbent core, there can include a space between the absorbent core and the liquid acquisition layer, or there can include an intervening layer between the absorbent core and the liquid acquisition layer. In embodiments, the liquid acquisition layer is in contact with the absorbent core. In embodiments, the absorbent article includes an intervening layer provided between the acquisition layer and the absorbent core. In embodiments, the liquid acquisition layer is in contact with the absorbent core on the topsheet side/wearer facing side and an intervening layer is provided between the acquisition layer and the absorbent core on the backsheet side/outer facing side. In embodiments, the liquid acquisition layer is in contact with the absorbent core on the backsheet side/outer facing side and an intervening layer is provided between the acquisition layer and the absorbent core on the topsheet side/wearer facing side. The intervening layer can be, for example, a second liquid pervious layer or liquid acquisition layer included to help facilitate spread of the liquid from the point of deposition to cover the full area of the absorbent core.

In embodiments, the absorbent article includes a liquid acquisition layer that is a nonwoven web of the disclosure. In embodiments, the wearable absorbent article includes a liquid acquisition layer that is a nonwoven web of the disclosure. In embodiments, the absorbent article includes a liquid acquisition layer that is a nonwoven composite article of the disclosure. In embodiments, the wearable absorbent article includes a liquid acquisition layer that is a nonwoven composite article of the disclosure.

Dissolution and Disintegration Test (MSTM-205)

A nonwoven web, water-soluble film, or laminate structure can be characterized by or tested for Dissolution Time and Disintegration Time according to the MonoSol Test Method 205 (MSTM 205), a method known in the art. See, for example, U.S. Pat. No. 7,022,656. The description provided below refers to a nonwoven web, while it is equally applicable to a water-soluble film or laminate structure.

Apparatus and Materials include:
  600 mL Beaker,
  Magnetic Stirrer (Labline Model No. 1250 or equivalent),
  Magnetic Stirring Rod (5 cm),
  Thermometer (0 to 100° C.±1° C.),
  Template, Stainless Steel (3.8 cm×3.2 cm),
  Timer (0-300 seconds, accurate to the nearest second),
  Polaroid 35 mm slide Mount (or equivalent),
  MonoSol 35 mm Slide Mount Holder (or equivalent), and
  Distilled water.

For each nonwoven web to be tested, three test specimens are cut from a nonwoven web sample that is a 3.8 cm×3.2 cm specimen. Specimens should be cut from areas of web evenly spaced along the traverse direction of the web. Each test specimen is then analyzed using the following procedure.

Lock each specimen in a separate 35 mm slide mount.

Fill beaker with 500 mL of distilled water. Measure water temperature with thermometer and, if necessary, heat or cool water to maintain the temperature at the temperature for which dissolution is being determined, e.g., 20° C. (about 68° F.).

Mark height of column of water. Place magnetic stirrer on base of holder. Place beaker on magnetic stirrer, add magnetic stirring rod to beaker, turn on stirrer, and adjust stir speed until a vortex develops which is approximately one-fifth the height of the water column. Mark depth of vortex.

Secure the 35 mm slide mount in the alligator clamp of the 35 mm slide mount holder such that the long end of the slide mount is parallel to the water surface. The depth adjuster of the holder should be set so that when dropped, and the end of the clamp will be 0.6 cm below the surface of the water.

One of the short sides of the slide mount should be next to the side of the beaker with the other positioned directly over the center of the stirring rod such that the nonwoven web surface is perpendicular to the flow of the water.

In one motion, drop the secured slide and clamp into the water and start the timer. Rupture occurs when the sample has become compromised within the slide, for example, when a hole is created. Disintegration occurs when the nonwoven web breaks apart and no sample material is left in the slide. When all visible nonwoven web is released from the slide mount, raise the slide out of the water while continuing to monitor the solution for undissolved nonwoven web fragments. Dissolution occurs when all nonwoven web fragments are no longer visible and the solution becomes clear. Rupture and dissolution can happen concurrently for nonwoven samples wherein the fibers are prepared from polyvinyl alcohol having a low degree of hydrolysis (e.g., about 65-88%). Dissolution times are recorded independently of rupture times when there is a 5-second or greater difference between rupture and dissolution.

Thinning time can also be determined using MSTM-205. Thinning of a nonwoven web occurs when some of the fibers making up the nonwoven web dissolve, while other fibers remain intact. The thinning of the web occurs prior to disintegration of the web. Thinning is characterized by a decrease in opacity, or increase in transparency, of the nonwoven web. The change from opaque to increasingly transparent and can be visually observed. During MSTM-205, after the secured slide and clamp have been dropped into the water, the opacity/transparency of the nonwoven web is monitored. At the time point wherein no change in opacity/transparency is observed (i.e., the web does not become any less opaque or more transparent), the time is recorded as the thinning time.

The results should include the following: complete sample identification; individual and average disintegration and dissolution times; and water temperature, at which the samples were tested.

Method for Determining Single Fiber Solubility

The solubility of a single fiber can be characterized by the water breaking temperature. The fiber breaking temperature can be determined as follows. A load of 2 mg/dtex is put on a fiber having a fixed length of 100 mm. Water temperature starts at 1.5° C. and is then raised by 1.5° C. increments every 2 minutes until the fiber breaks. The temperature, at which the fiber breaks, is denoted as the water breaking temperature.

The solubility of a single fiber can also be characterized by the temperature of complete dissolution. The temperature of complete dissolution can be determined as follows. 0.2 g of fibers having a fixed length of 2 mm are added to 100 mL of water. Water temperature starts at 1.5° C. and is then raised by 1.5° C. increments every 2 minutes until the fiber completely dissolves. The sample is agitated at each temperature. The temperature at which the fiber completely dissolves in less than 30 seconds is denoted as the complete dissolution temperature.

Diameter Test Method

The diameter of a discrete fiber or a fiber within a nonwoven web is determined by using a scanning electron microscope (SEM) or an optical microscope and an image analysis software. A magnification of 200 to 10,000 times is chosen such that the fibers are suitably enlarged for measurement. When using the SEM, the samples are sputtered with gold or a palladium compound to avoid electric charging and vibrations of the fiber in the electron beam. A manual procedure for determining the fiber diameters is used from the image (on monitor screen) taken with the SEM or the optical microscope. Using a mouse and a cursor tool, the edge of a randomly selected fiber is sought and then measured across its width (i.e., perpendicular to the fiber direction at that point) to the other edge of the fiber. A scaled and calibrated image analysis tool provides the scaling to get an actual reading in microns. For fibers within a nonwoven web, several fibers are randomly selected across the sample of nonwoven web using the SEM or the optical microscope. At least two portions of the nonwoven web material are cut and tested in this manner. Altogether at least 100 such measurements are made and then all data are recorded for statistical analysis. The recorded data are used to calculate average (mean) of the fibers, standard deviation of the fibers, and median fiber diameters.

Tensile Strength, Modulus, and Elongation Test

A nonwoven web, water-soluble film, or laminate structure characterized by or to be tested for tensile strength according to the Tensile Strength (TS) Test, modulus (or tensile stress) according to the Modulus (MOD) Test, and elongation according to the Elongation Test is analyzed as follows. The description provided below refers to a nonwoven web, while it is equally applicable to a water-soluble film or laminate structure. The procedure includes the determination of tensile strength and the determination of modulus at 10% elongation according to ASTM D 882 ("Standard Test Method for Tensile Properties of Thin Plastic Sheeting") or equivalent. An INSTRON tensile testing apparatus (Model 5544 Tensile Tester or equivalent) is used for the collection of nonwoven web data. A minimum of three test specimens, each cut with reliable cutting tools to ensure dimensional stability and reproducibility, are tested in the machine direction (MD) (where applicable) for each measurement. Tests are conducted in the standard laboratory atmosphere of 23±2.0° C. and 35±5% relative humidity. For tensile strength or modulus determination, 1"-wide (2.54 cm) samples of a nonwoven web are prepared. The sample is then transferred to the INSTRON tensile testing machine to proceed with testing while minimizing exposure in the 35% relative humidity environment. The tensile testing machine is prepared according to manufacturer instructions, equipped with a 500 N load cell, and calibrated. The correct grips and faces are fitted (INSTRON grips having model number 2702-032 faces, which are rubber coated and 25 mm wide, or equivalent). The samples are mounted into the tensile testing machine and analyzed to determine the 100% modulus (i.e., stress required to achieve 100% film elongation), tensile strength (i.e., stress required to break film), and elongation % (sample length at break relative to the initial sample length). In general, the higher the elongation % for a sample, the better the processability characteristics for the nonwoven web (e.g., increased formability into packets or pouches).

Determination of Basis Weight

Basis weight is determined according to ASTM D3776/D3776M-09a (2017). Briefly, a nonwoven specimen having an area of at least 130 cm$^2$ or a number of smaller die cut specimens taken from different locations in the sample and having a total area of at least 130 cm$^2$ are cut. The specimen(s) are weighed to determine mass on a top loading analytical balance with a resolution of ±0.001 g. The balance is protected from air drafts and other disturbances using a draft shield. Specimens of fabric may be weighed together. The mass is calculated in ounces per square yard, ounces per linear yard, linear yards per pound, or grams per square meter to three significant figures.

Determination of Moisture Vapor Transmission Rate

Moisture Vapor Transmission Rate (MVTR) is determined according to MSTM-136. The MVTR defines how much moisture per day moves through a sample. The description provided below refers to a nonwoven web, while it is equally applicable to a water-soluble film or laminate structure.

Apparatus and Materials include:
Permatran-W Model 3/34 (or equivalent),
Compressed Gas Cylinder of Nitrogen (99.7% or above),
Regulator-Tee (part number 027-343),
Main Line Supply regulator,
HPLC Grade Water (or equivalent),
10 cc Syringe with Luerlok Tip (part number 800-020),
Powder-free gloves,
High vacuum grease (part number 930-022),
(2) Test Cells,
Cutting template,
Cutting board,
Razor blade with handle, and
Cut-resistant glove.

Preparation of the Permatran W-Model 3/34: Make sure nitrogen pressure level is above 300 psi, the pressure on the carrier gas regulator-tee reads 29 psi (must not exceed 32 psi), and the main line supply regulator pressure is set to 35 psi. Open the door on the instrument panel to access humidifier to check the water level. If water level is low, fill a syringe with HPLC-grade water and insert the leur fitting on the syringe into the "fill Port" for the reservoir. Open the "Fill Valve" by turning it 2-3 turns counterclockwise then push in the plunger on the syringe to force the water into the reservoir. Close the 'Fill Valve" and remove syringe. The water level should not exceed a line marked adjacent to reservoir.

Preparation and Testing of Samples: For each nonwoven web to be tested, take the sample web and lay it flat on the cutting board. Place the template on top of the web and use the razor blade with a handle to cut out the sample. Make sure cut-resistant glove is worn when cutting the sample out. Set the sample aside. Grease around the sealing surfaces of the test cell's top piece with high vacuum grease. Mount the film sample on top of the test cell's top piece. Orientation may be important. If a homogeneous material, orientation is not critical. If a multi-layered and laminated material, place the multilayered film or laminate with barrier coating or laminate up, towards the top of the cell. For example, a one-side, wax coated PVOH web should be mounted with the wax side up, placing the wax towards the carrier gas (Nitrogen). Place the test cell's top piece on top of the test cell's bottom piece. Make sure the test cell is clamped together with a good seal. Press the cell load/unload button to open cell tray. Grasp the test cell by the front and back edges and lower it straight down. Close the cell tray completely by gently pushing straight towards panel. Press the cell load/unload button to clamp the cell while a click can be heard. Repeat for second sample.

After the samples are loaded and the instrument is ready, the test parameters must be set. There are two types of test parameters, cell parameters and instrument parameters. Cell parameters are specific to each cell while instrument parameters are common for all cells. Touch the "Test Button" on the screen. Under "Auto Test" select "Tab A". Touch "Cell Tab". Fill out the following by touching each bubble: ID, Area ($cm^2$), Thickness (mil). Note: Area of template is 50 $cm^2$. Repeat for "Tab B". Touch "Instrument Tab". Fill out the following by touching each bubble: Cell Temp (° C.) and Test Gas RH (%). Make sure 100% RH is set to off. Cell temperature can be set to a minimum of 10° C. to maximum of 40° C. Test Gas RH can be set to minimum 5% to 90%. If 100% RH is needed, it requires a different method. Repeat for "Tab B". Once the test parameters are set, select "Start Selected" or "Start All" depending on sample number. Note: The indicator light for each cell on front panel will be green indicating the start of test.

Surface Resistivity Measurements

Surface resistivity of nonwoven webs and films can be measured according to ASTM D257.

Softness Rating

The hand feel of a nonwoven web or pouch of the disclosure is related to the softness of the sample and can be evaluated using relative testing methods. A tester carrying out the softness evaluation uses clean hands to feel the samples in whatever manner or method the individual chose, to determine a softness rating for the nonwoven webs and articles of the disclosure as compared to a control material comprising a nonwoven web consisting of fibers consisting of polyvinyl alcohol copolymers having a degree of hydrolysis of 88%, the fibers having a 2.2 dtex/51 mm cut, having a softness rating of 1 (softest) and a control material comprising a nonwoven web consisting of fibers consisting of 75% polyvinyl alcohol copolymers having a degree of hydrolysis of 88%, the fibers having a 2.2/51 mm cut, and 25% of 22 dtex/38 mm PET fiber, having a softness rating of 5 (roughest/coarsest). The hand panel is a blind study so that the raters are not swayed by their perception of sample names. Samples were rated from 1 to 5.

Flushability Test

The ability of the nonwoven webs and/or laminates of the disclosure to be flushed in a septic or municipal sewage treatment system can be determined according to a modified INDA/EDANA—Criteria for Recognition as a Flushable Product, as provided below. The below test references nonwoven web samples; however, it will be understood that the method can also be used for laminate structures.

Equipment and materials include:
Rocking digital platform shaker,
Two clear, plastic, 12×5×3.9 inches containers,
Two sieves (12.5 mm apertures),
Dried nonwoven web samples, and
A 100° C. oven.
Parameters include:
Rocking platform set to 18 RPM and 11° tilt period,
1 L tap water per container, and
30 min testing period.
Testing Procedure:
1. Place two containers on rocking platform. This method tests two samples at a time.

2. Measure 1 L of tap water in beaker and pour into one plastic container. Repeat for other container. Make sure tap water in containers is at 15° C.±1° C. before starting test.
3. Record weight of the initial dried test sample (initial sample mass (g)) and weight of sieves (initial sieve mass (g)) and record independently.
4. Set appropriate parameters on digital rocking platform.
5. Place each test sample in their corresponding container and immediately start the agitation process (rocking of the platform),
6. Once the process is complete (after 30 minutes), take each container and pour through their corresponding sieves. Pouring at a height of 10 cm above sieve plate.
7. Rinse container into sieve to ensure all of the remaining test sample was removed.
8. Place sieve in 100° C. oven for 45 minutes to ensure all water evaporates.
9. Record weight of sieve and remaining test sample together (total final mass (g)).
10. Calculate the total retained sample mass (final sample mass (g)):

Final sample mass (g)=total final mass (g)−initial sieve mass (g)

11. Calculate the percent (%) disintegration:

% Disintegration=[1−(final sample mass (g)/initial sample mass (g))]×100

12. Make sure sieves are cleaned, dried, and re-weighed before starting next test.
13. Repeat test until replicate of N=3 is complete for each specific test sample.

A sample is sufficiently flushable to be disposed of by flushing in a septic or municipal sewage treatment system when the sample has a percent disintegration equal to or greater than of at least 20%. In embodiments, the nonwoven webs, laminates, and pouches of the disclosure can have a percent disintegration of at least 20%, at least 30%, at least 35%, at least 40%, at least 45%, at least 50%, at least 55%, at least 60%, at least 65%, at least 70%, at least 75%, at least 80%, at least 85%, at least 90%, or at least 95% as measured by the Flushability Test.

Liquid Release Test

A wire frame cage is used for a sample, such as a water-soluble pouch, in the Liquid Release Test described herein. An apparatus for performing the Liquid Release Test includes a beaker resting on a stand, the stand holding a rod for lowering the cage into the beaker, and the rod being fixable by a collar with a set screw.

A water-soluble nonwoven web, film, and/or pouch characterized by or to be tested for delayed solubility according to the Liquid Release Test is analyzed as follows using the following materials:

2 L beaker and 1.2 liters of deionized (DI) water;
Water-soluble pouch to be tested (the pouch is pre-conditioned for two weeks at 38° C.; for results to be comparative, all nonwoven webs tested should have the same basis weight and all films tested should have the same thickness, for example, 88 μm or 76 μm);
Thermometer;
Wire cage; and
Timer.

Before running the experiment, ensure that enough deionized water is available to repeat the experiment five times, and ensure that the wire cage and beaker are clean and dry.

The wire frame cage is a plastic coated wire cage (4"×3.5"×2.5") with no sharp edges, or equivalent. The gauge of the wire should be about 1.25 mm and the wire should have openings the size of 0.5 inch (1.27 cm) squares.

To set up for the test, carefully place the water-soluble pouch in the cage while not scratching the pouch on the cage and allowing free space for the pouch to move. Do not bind the pouch tightly with the wire cage, while still ensuring it is secure and will not come out of the cage. The orientation of the pouch in the cage should be such that the natural buoyancy of the pouch, if any, is allowed (i.e., the side of the pouch that will float to the top should be placed towards the top). If the pouch is symmetrical, the orientation of the pouch generally will not matter.

Next, fill the 2 L beaker with 1200 milliliters of 20° C. deionized water.

Next, lower the wire frame cage with the enclosed pouch into the water. Ensure that the cage is 1 inch (2.54 cm) from the bottom of the beaker. Be sure to fully submerge the pouch on all sides. Ensure that the cage is stable and will not move and start a timer as soon as the pouch is lowered into the water. The position of the cage with respect to the water in the beaker can be adjusted and maintained by any suitable means, for example, by using a clamp fixed above the beaker, and a rod attached to the top of the cage. The clamp can engage the rod to fix the position of the cage, and tension on the clamp can be lowered in order to lower the cage into the water. Other means of frictional engagement can be used in the alternative to a clamp, for example, a collar with a set screw.

Liquid content release is defined as the first visual evidence of the liquid leaving the submerged pouch.

Determination of the Degree of Hydrolysis of a Fiber

Titration Method. The degree of hydrolysis of a polymer in a fiber can be determined using titration. In particular, a known amount of polyvinyl alcohol fibers are dissolved in 200 mL of deionized water by agitation and heating the mixture at a temperature higher than 70° C. Once all of the PVOH polymer has dissolved, the solution is cooled to room temperature. Once the solution has cooled, 4-5 drops of phenolphthalein indicator solution are added to the PVOH solution, along with 20.0 mL of 0.5N NaOH solution. The solution is mixed and left at room temperature for a minimum of 2 hours. After this time, 20.0 mL of 0.5N sulfuric acid are added to the solution and mixed. The solution is titrated with 0.1N NaOH solution until the endpoint, which is taken as the point at which the solution turns faint pink and maintains this color without returning to a colorless solution for a minimum of 30 seconds. Using the measurements obtained in the aforementioned procedure, the DH of the PVOH polymer is determined via the following calculations $$A_1 = \frac{(V_{sample} - V_{blank}) \times N \times 0.06005}{Wt_{sample} \times \frac{P}{100}}$$

$$A_2 = \frac{44.05 \times A_1}{60.05 - (0.42 \times A_1)}$$

$$DH = 100 - A_2$$

where:
A1: residual acetate groups (wt %)
A2: residual acetate groups (mole %)

DH: degree of hydrolysis (mole %)
Vsample: volume of 0.1N NaOH solution added during titration of sample (mL)
Vblank: volume of 0.1N NaOH solution added during titration of blank (mL)
N: certified concentration of standardized 0.1N NaOH solution used in titration step
Wtsample: sample mass (g)
P: purity of PVOH sample=100−(volatile matter (wt %)+sodium acetate (wt %)).

FTIR Method. FTIR can be used to determine if a modification to the outer portion of a fiber surface has occurred via attenuated total reflectance (ATR). The depth of the fiber which this method measures is dependent on the specific ATR apparatus, in particular, the crystal used, and can range from less than 1 to several microns. Determination of the existence of a specific modification via ATR is dependent on the chemical structure of the modifying agent, and therefore on the chemical structure of the resulting fiber. For example, if a fiber were to be modified such that it would result in the presence of nitro functional groups in the chemical structure of the fiber, this could be detected via ATR. Nitro functional groups exhibit strong IR absorbance in the region of 1515-1560 $cm^{-1}$. A relative increase in absorbance signal in this region, when compared to a non-modified fiber, is indicative of successful modification of the fiber given the fiber has been properly washed of reactants, solvents, and/or activating agents from the modification process that may contain nitro and/or other functional groups that potentially absorb in the same region. In the same way, determination of modified fibers containing other functional groups with known absorbance values can be detected, given that such fibers have been properly washed of reactants, solvents, and/or activating agents from the modification process that potentially absorb in the same region. A Thermo Scientific Nicolet iS10 FTIR Spectrometer using a Thermo Scientific Smart iTX ATR accessory equipped with a diamond crystal or equivalent can be used to characterize samples.

DSC Method (MSTM-122). A fiber, a nonwoven web, water-soluble film, or laminate structure can be characterized by or tested by differential scanning calorimetry (DSC). This method is used to determine the melting point, glass transition, crystallization, and heat of fusion events in various polymer samples (e.g., polyvinyl alcohol samples). An Auto Q20 DSC or equivalent can be used to characterize the samples.

Test Specimen

The polymer sample should be between 0.00300 g and 0.01200 g (3.00 mg-12.00 mg) unless otherwise stated. Sample size is dependent on the material tested, and must cover the bottom of the pan. The sample must fit inside the sealed pan without puncturing or deforming the pan.

Gradient Test Method. A gradient in the degree of modification of a fiber can be determined and quantified using cross-section X-ray photoelectron spectroscopy (XPS), depth XPS, NMR techniques (such as, solid state NMR), ultraviolet photoelectron spectrometry (UPS), environmental SCM, Auger electron spectroscopy (AES or SAM), or elemental scanning electron microscopy (SEM). The shift in bonding energy of the modification from an —OH group or a —COMe group from the polyvinyl alcohol or polyvinyl acetate prior to the modification would result in a change in the spectrum of the methods. It is noted that the chemical shifts will differ based on the type of modification that is done to the fiber.

For XPS analysis, the depth of the fiber which this method measures is dependent on the specific ion beam used during the XPS analysis for depth profiling to determine changes in degree of modification as a function of cross section. By taking the ratio of the deconvoluted peaks at 287.6 eV and 288.8 eV, representing the carboxyl and carbonyl groups of acetate groups for non-fully hydrolyzed PVOH, combined with those of 286.5 eV and 532.8 eV, corresponding to the hydroxyl groups of PVOH, to the peaks that correspond with particular modification that is made to the PVOH, one can use the equation obtained by plotting the same ratios for PVOH resins against the known degree of modification (if any) of the starting PVOH to determine the degree of modification of the unknown sample. This method can be repeated between ion beam sputtering stages to gain a complete depth profile and change of degree of modification across the cross-section of the PVOH fibers. XPS methods are described in Gilbert et al "Depth-profiling X-ray photoelectron spectroscopy (XPS) analysis of interlayer diffusion in polyelectrolyte multilayers" PNAS, vol. 110, no. 17, 6651-6656 (2013) (https://www.pnas.org/content/pnas/1/10/17/6651.full.pdf), and European Polymer Journal 126 (2020) 109544, the entirety of which are hereby incorporated by reference.

AES methods are described in ASTM E984-12, the entirety of which is hereby incorporated by reference.

One or more optional features that can be used individually or in combination are described in the following paragraphs. Optionally, the fiber to be treated is a polyvinyl acetate fiber. Optionally, the fiber to be treated is a polyvinyl alcohol fiber. Optionally, the fiber to be treated is a polyvinyl alcohol fiber comprising a polyvinyl alcohol copolymer having a degree of hydrolysis in a range of 79-99%. Optionally, the fiber to be treated is a polyvinyl alcohol fiber comprising a polyvinyl alcohol copolymer having a degree of hydrolysis in a range of 88%-96%. Optionally, the fiber to be treated is a polyvinyl alcohol fiber comprising a polyvinyl alcohol copolymer having a degree of hydrolysis of 88%, 92%, or 96%. Optionally, the fiber to be treated is a polyvinyl alcohol fiber comprising a polyvinyl alcohol homopolymer or copolymer. Optionally, the fiber to be treated is a polyvinyl alcohol fiber comprising an anionically modified copolymer. Optionally, the fiber to be treated is a polyvinyl alcohol fiber comprising a polyvinyl alcohol (PVOH) copolymer and an anionically modified PVOH copolymer. An example of a PVOH copolymer is a copolymer of vinyl acetate and vinyl alcohol.

Optionally, the modification agent comprises a maleic anhydride. Optionally, the solvent for the modification agent comprises methanol. Optionally, the solvent for the modification agent comprises methanol and water. Optionally, the method further comprises an activator, wherein the activator comprises sodium hydroxide.

Optionally, the admixing of the fiber to be treated, the modification agent, and the solvent comprises immersing the fiber in the solvent with the modification agent. Optionally, the admixing comprises heating the mixture of the fiber, the modification agent, and the solvent. Optionally, the admixing comprises heating the mixture of the fiber, the modification agent, and the solvent to a temperature of about 65° C. to about 75° C. Optionally, the admixing comprises heating the mixture of the fiber, the modification agent, and the solvent for up to about three to about seven hours.

Optionally, the fiber to be treated can be contacted with the modification agent to increase the degree of modification of a polymer comprising at least one of a vinyl acetate moiety or a vinyl alcohol moiety of the fiber in a region of the fiber comprising at least the surface of the fiber. Optionally, the contacting can be by immersion. Optionally, the contacting can be by dip-coating. Optionally, the contacting can be by spraying. Optionally, the contacting can be by brushing. Optionally, the contacting can be by rolling.

The following paragraphs describe further aspects of the disclosure.

1. A fiber having a surface region and an interior region, the fiber comprising:

a polymer comprising at least one of a vinyl acetate moiety or a vinyl alcohol moiety chemically modified with a modification agent, the fiber having a transverse cross-section including the interior region comprising the polymer having a first degree of modification and the surface region comprising the polymer having a second degree of modification greater than the first degree of modification.

2. The fiber according to clause 1, wherein the transverse cross-section of the fiber has an increasing gradient in a degree of modification of the polymer from the interior region to the surface region.

3. The fiber according to clause 1 or 2, wherein the polymer comprising at least one of a vinyl acetate moiety or a vinyl alcohol moiety without modification comprises a polyvinyl alcohol homopolymer, a polyvinyl acetate homopolymer, a polyvinyl alcohol copolymer, or any combination thereof.

4. The fiber according to clause 3, wherein the polyvinyl alcohol copolymer is a copolymer of vinyl acetate and vinyl alcohol.

5. The fiber according to clause 4, wherein the polyvinyl alcohol copolymer comprises an anionic modification.

6. The fiber according to clause 5, wherein the anionic modification comprises a carboxylate, a sulfonate, or a combination thereof.

7. The fiber according to any of clauses 1-6, wherein the polymer comprising at least one of a vinyl acetate moiety or a vinyl alcohol moiety chemically modified with the modification agent is chemically bonded with a moiety of the modification agent.

8. The fiber according to clause 7, wherein the modification agent comprises an anhydride, and the modification agent moiety comprises a carboxyl acid from the anhydride or a salt thereof.

9. The fiber according to clause 7, wherein the anhydride is selected from acetic anhydride, propionic anhydride, isobutyric anhydride, maleic anhydride, phthalic anhydride, glutaric anhydride, itaconic anhydride, citraconic anhydride, glutaconic anhydride, or any combination thereof.

10. The fiber according to clause 7, wherein the polymer comprising at least one of a vinyl acetate moiety or a vinyl alcohol moiety before modification is a copolymer of vinyl acetate and vinyl alcohol having a degree of hydrolysis in a range of from about 79% to about 99%, and the modification agent comprises maleic anhydride.

11. The fiber according to any of clauses 1-10, wherein the first degree of modification is about 0%.

12. The fiber according to any of clauses 1-11, further comprising an additional polymer.

13. The fiber according to clause 12, wherein the additional polymer is selected from the group consisting of a polyvinyl alcohol, a polyvinyl acetate, a polyacrylate, a water-soluble acrylate copolymer, a polyvinyl pyrrolidone, a polyethylenimine, a pullulan, a guar gum, a gum Acacia, a xanthan gum, a carrageenan, a starch, a modified starch, a polyalkylene oxide, a polyacrylamide, a polyacrylic acid, a cellulose, a cellulose ether, a cellulose ester, a cellulose amide, a polycarboxylic acid, a polyaminoacid, a polyamide, a gelatin, a dextrin, copolymers of the foregoing, and any combination of any of the foregoing additional polymers or copolymers.

14. The fiber according to any of clauses 1-13, wherein the fiber is water-soluble.

15. The fiber according to clause 14, wherein the fiber has a dissolution time of less than 200 seconds in water at about 23° C.

16. A fiber having a longitudinal axis and a transverse cross-section perpendicular to the longitudinal axis, the fiber further having a core-sheath structure along at least a portion of the longitudinal axis, the fiber comprising:

a core region comprising a polymer comprising at least one of a vinyl acetate moiety and a vinyl alcohol moiety chemically modified with a modification agent and having a first degree of modification, and a sheath region comprising the polymer comprising at least one of a vinyl acetate moiety and a vinyl alcohol moiety chemically modified with the modification agent and having a second degree of modification greater than the first degree of modification.

17. The fiber according to clause 16, further comprising an intermediate region disposed between the core region and the sheath region, the intermediate region comprising the polymer comprising at least one of a vinyl acetate moiety and a vinyl alcohol moiety chemically modified with the modification agent and having a third degree of modification greater than the first degree of modification and less than the second degree of modification.

18. The fiber according to clause 17, comprising a plurality of intermediate regions disposed between the core region and the sheath region, such that the transverse cross-section of the fiber has a gradient in the degree of modification from the core region to the sheath region.

19. The fiber according to any of clauses 16-18, wherein the transverse cross-section of the fiber is characterized by a mean radius and the sheath region comprises 0.5% of the mean radius of the fiber, or in a range of 0.5 to 12% of the mean radius of the fiber.

20. The fiber according to clause 17, wherein the polymer in the core region, the polymer in the sheath region, and optionally the polymer in the intermediate region have an equal degree of polymerization.

21. The fiber according to any of clauses 16-20, wherein the polymer comprising at least one of a vinyl acetate moiety or a vinyl alcohol moiety without modification comprises a polyvinyl alcohol homopolymer, a polyvinyl acetate homopolymer, a polyvinyl alcohol copolymer, or any combination thereof.

22. The fiber according to clause 21, wherein the polyvinyl alcohol copolymer is a copolymer of vinyl acetate and vinyl alcohol.

23. The fiber according to any of clauses 16-22, wherein the polymer comprising at least one of a vinyl acetate moiety or a vinyl alcohol moiety chemically modified with the modification agent is chemically bonded with a moiety of the modification agent.

24. The fiber according to any of clauses 16-23, wherein the modification agent comprises an anhydride.

25. The fiber according to any of clauses 16-24, wherein the anhydride is selected from acetic anhydride, propionic anhydride, isobutyric anhydride, maleic anhydride, phthalic anhydride, glutaric anhydride, itaconic anhydride, citraconic anhydride, glutaconic anhydride, or any combination thereof.

26. A nonwoven web comprising the modified fiber according to any of clauses 1-25.

27. A multilayer nonwoven web comprising a first layer comprising the nonwoven web according to clause 26.

28. A pouch comprising the nonwoven web according to clause 27 in the form of a pouch defining an interior pouch volume.

29. A sealed article comprising the nonwoven web according to clause 26.

30. A flushable article comprising the nonwoven web according to clause 26.

31. A wearable absorbent article, comprising:
an absorbent core having a wearer facing side and an outer facing side; and
a liquid acquisition layer,
wherein the liquid acquisition layer comprises a nonwoven web according to clause 26.

EXAMPLES

Fibers as Starting Materials

As shown in Table 2, five fibers, Fiber A, Fiber B, Fiber C, Fiber D, and Fiber E, which comprise a copolymer of vinyl acetate and vinyl alcohol having a degree of hydrolysis of 88%, 92%, 96%, 98%, and 99.99%, respectively, are examples of the starting materials. These fibers have uniform composition, and have additional properties shown in Table 2. Fibers A-C and E, particularly Fiber A, were used as the starting materials in the Examples described herein. The descriptions are also applicable to Fiber D. In the Examples and Comparative Examples described herein, Fiber A used has a fineness of 2.2 dtex.

TABLE 2

| Fiber | Viscosity (4% solution) | DH (mol %) | Fineness (dtex) | Solubility Temp (° C.) | Tenacity (cN/dtex) | Elongation (%) |
|---|---|---|---|---|---|---|
| A | 22-23 | 88 | 1.7 2.2 | 20 | 5 | 20 |
| B | 22-23 | 92 | 1.7 2.2 | 30 | 6 | 18 |
| C | 22-23 | 96 | 1.2 1.7 | 40 | 7 | 15 |
| D | 22-23 | 98 | 1.2 1.7 | 70 | 7 | 12 |
| E | 22-23 | 99.99 | 1.2 1.7 | 95 | 9 | 10 |

Examples 1-3

Fibers A, B, and C comprising vinyl alcohol moieties and having a degree of hydrolysis of 88%, 92% or 96% as the sole fiber forming material or in combination with other fiber forming materials were post-process modified as follows. In the Examples, a polymer comprising vinyl alcohol moieties is referred as "a polyvinyl alcohol polymer," and a fiber comprising such a polymer is referred as "a polyvinyl alcohol (PVOH) fiber." 4 g of the polyvinyl alcohol fibers were immersed in 200 g of methanol. The mixture of polyvinyl alcohol fibers and methanol was heated to 70° C. The fibers do not dissolve in the methanol. 5 g maleic anhydride and 60 mL of 1 M sodium hydroxide in water were added into the heated mixture. The resulting mixture is agitated at 70° C. for 5 hours. The resulting modified fibers were filtered and washed with methanol. The modified fibers were dried in a fume hood for 12 hours. The resulting dried fibers were measured using the titration method disclosed herein, MSTM 205, FTIR-ATR, and/or DSC, and the chemical modification was confirmed.

Thus, Examples 1-3 show using methods of the disclosure to prepare post-process carboxylate-modified polyvinyl alcohol fibers. A modification reaction of a copolymer of vinyl acetate and vinyl alcohol with maleic anhydride is illustrated in Scheme (1) as follows:

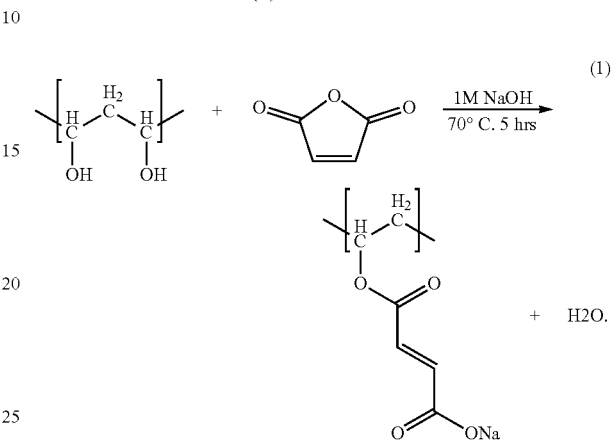

The esterification reaction between a hydroxyl group in the copolymer and maleic anhydride provides a modified polymer having monomethyl maleate (MMM) or salt thereof chemically attached on the polymer backbone through an ester bond. The modified fibers have a core-sheath structure as described herein.

Additional solvents such as THF and DCM (dichoromethane) and additional anhydrides such as glutaric anhydride, itaconic anhydride, and phthalic anhydrides were used. The modification reactions were performed at different temperatures for different periods of time. The fibers stayed intact in each solvent. Methanol solubilizes reactants such as anhydrides and bases (e.g., NaOH, KOH), while THF and DCM partially solubilizes the bases. THF and DCM are more preferred than methanol because THF and DCM favor esterification over saponification of the polymer. When methanol is used, saponification may occur and the esterification reaction occurs at higher temperatures. When THF or DCM was used as a solvent, a modified polymer having monomethyl maleate (MMM) or salt thereof can be obtained through the esterification reaction between a hydroxyl group in the copolymer and maleic anhydride, without saponification. Such a modification was confirmed by FT-IR results, for example, the appearance of a peak at 1580 cm$^{-1}$ from the carboxylate group at the end of MMM. Meanwhile, the solubility of the nonwoven web comprising such modified fibers was maintained. The modification reactions for Fiber A with anhydrides including maleic anhydride, glutaric anhydride, itaconic anhydride, and phthalic anhydride were performed and compared under the same conditions, for example, in THF at 60° C. for 5 hours. When glutaric anhydride and itaconic anhydride were used, the modified fibers showed FT-IR results similar to that of MMM, while the fibers modified with itaconic anhydride showed lower signal intensity of modification. The modification with phthalic anhydride showed a very strong intensity, the highest intensity among the modifications with the four anhydrides under a same condition, due to conjugated carbon bonds near the binding site, and also showed a benzene ring signal near 1450 cm$^{-1}$. Phthalic anhydride was selected additionally because of its antimicrobial properties. Modification of the fibers with each anhydride was also achieved at room temperature. The modified fibers with maleic anhydride, phthalic anhydride, and glutaric anhydride maintained the desired white appearance of unmodified fibers. Experimental results also showed that glass transition temperatures of the same polymers had no significant difference before and after the chemical modification.

In the Examples described herein, the starting fibers include a copolymer of vinyl acetate and vinyl alcohol, and the modified fibers were chemically modified with functional groups such as carboxylate and sulfonate. The descriptions are also applicable to the fibers comprising a modified copolymer, such as an anionically modified PVOH copolymer, having carboxylate and/or sulfonate, and such fibers are further chemically modified with a modification agent to increase the degree of modification.

Examples 4-6

Fibers A-C comprising vinyl alcohol moieties and having a degree of hydrolysis of 88%, 92% or 96% as the sole fiber forming material or in combination with other fiber forming materials were post-process modified as follows. 5 g of the polyvinyl alcohol fibers were immersed in methanol. The fibers do not dissolve in the solvent. The resulting mixture was heated to about 30° C. to about 80° C. Aminopropyl sulfonate and an activator (e.g., an acid or a base) were then added to the heated mixture. The heated mixture was then agitated for 1 hour to 10 hours. After agitation, the mixture was cooled and the fibers were separated from the solvent. The resulting modified fibers were dried to remove any residual solvent prior to measuring the degree of modification of the polymer in the fibers using the titration method disclosed herein, MSTM 205, FTIR-ATR, and/or DSC.

Thus, Examples 4-6 show using methods of the disclosure to prepare post-process sulfonate-modified polyvinyl alcohol fibers.

Examples 7-9

Fibers A-C comprising vinyl alcohol moieties and having a degree of hydrolysis of 88%, 92% or 96% as the sole fiber forming material or in combination with other fiber forming materials were post-process modified as follows. 5 g of the polyvinyl alcohol fibers were immersed in methanol. The fibers do not dissolve in the solvent. The resulting mixture was heated to about 30° C. to about 80° C. A lactam comprising a pyrrolidone or a caprolactam, and an activator (e.g., an acid or a base) were then added to the heated mixture. The heated mixture was then agitated for 1 hour to 10 hours. After agitation, the mixture was cooled and the fibers were separated from the solvent. The resulting modified fibers were dried to remove any residual solvent prior to measuring the degree of modification of the polymer using the titration method disclosed herein, MSTM 205, FTIR-ATR, and/or DSC.

Thus, Examples 7-9 show using methods of the disclosure to prepare post-process polyvinyl alcohol fibers chemically modified with a lactam, through a ring-opening reaction of the lactam with a hydroxyl group from the vinyl alcohol moieties.

Examples 10-12

Fibers A-C comprising vinyl alcohol moieties and having a degree of hydrolysis of 88%, 92% or 96% as the sole fiber forming material or in combination with other fiber forming materials were post-process modified as follows. 5 g of the polyvinyl alcohol fibers were immersed in methanol. The fibers do not dissolve in the solvent. The resulting mixture was heated to about 30° C. to about 80° C. A sulfonic acid comprising 2-acrylamido-2-methylpropanesulfonic acid, and an activator (e.g., an acid or a base) were then added to the heated mixture. The heated mixture was then agitated for 1 hour to 10 hours. After agitation, the mixture was cooled and the fibers were separated from the solvent. The resulting modified fibers were dried to remove any residual solvent prior to measuring the degree of modification of the polymer using the titration method disclosed herein, MSTM 205, FTIR-ATR, and/or DSC.

Thus, Examples 10-12 show using methods of the disclosure to prepare post-process sulfonic acid-modified polyvinyl alcohol fibers.

Examples 13-15

Figure 6:
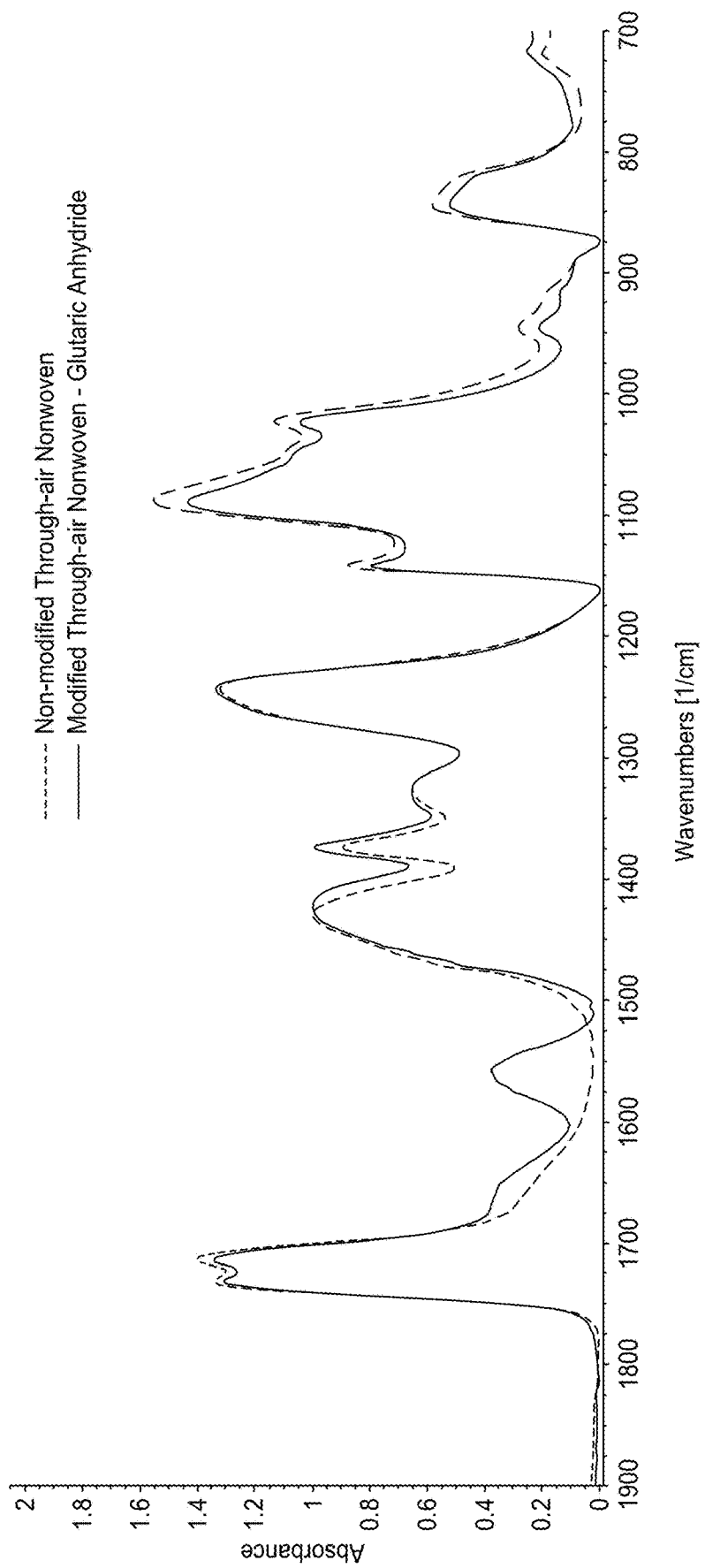
FIG. 6 shows ATR-FTIR results of a through-air nonwoven web comprising a plurality of fibers (Fiber A) without and with chemical modification with glutaric anhydride in THF at 60° C. for 5 hours, according to example embodiments.
Figure 7:
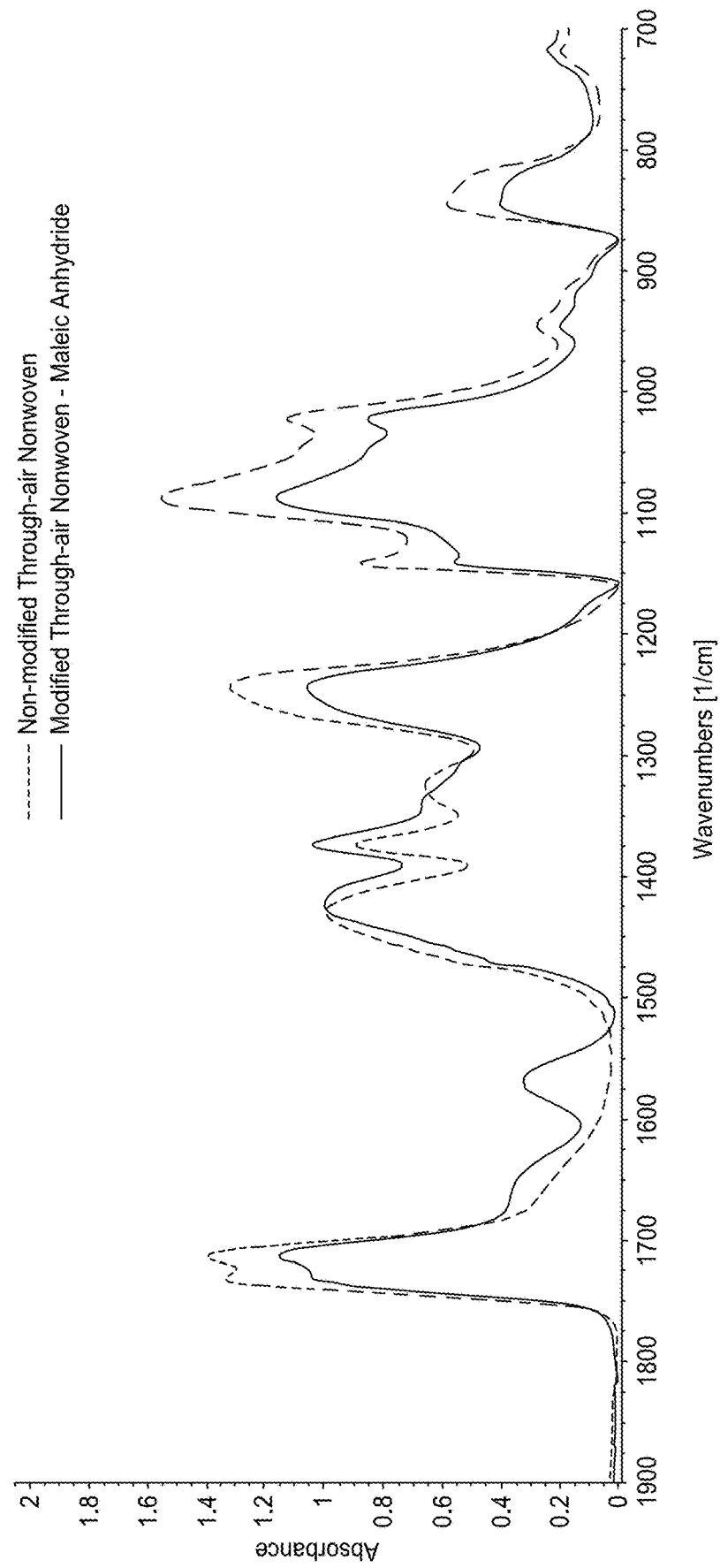
FIG. 7 shows ATR-FTIR results of a through-air nonwoven web comprising a plurality of fibers (Fiber A) without and with chemical modification with maleic anhydride in THF at 60° C. for 5 hours, according to example embodiments.
Figure 8:
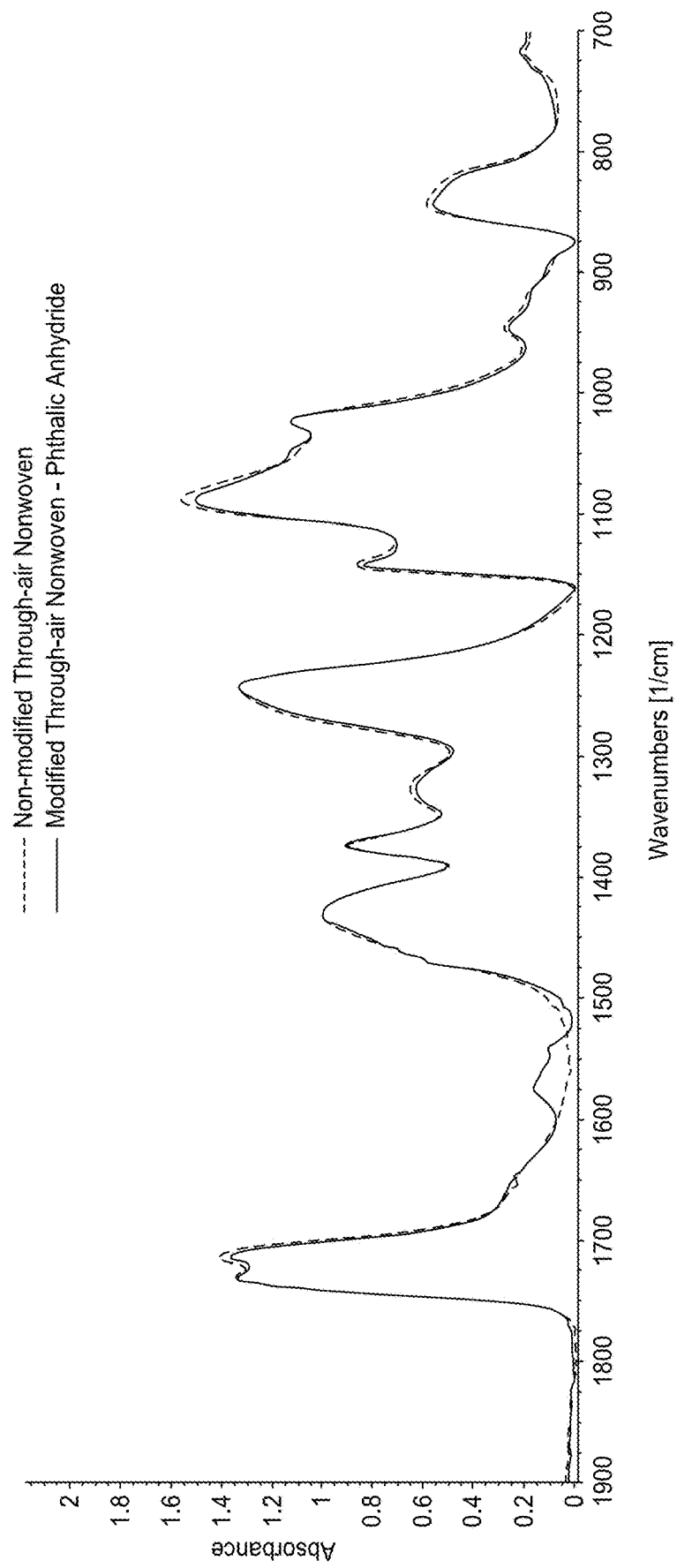
FIG. 8 shows ATR-FTIR results of a through-air nonwoven web comprising a plurality of fibers (Fiber A) without and with chemical modification with phthalic anhydride in THF at 60° C. for 5 hour, according to example embodiments.

Fibers (Fiber A) comprising a copolymer of vinyl acetate and vinyl alcohol and having an 88% degree of hydrolysis were chemically modified with an anhydride in THF at 60° C. for 5 hours. The fibers were bonded using a hot through-air bonding method to provide nonwoven samples. FIGS. 6-8 show the ATR-FTIR curves of nonwoven samples (Examples 13-15) comprising fibers chemically modified with glutaric anhydride, maleic anhydride, and phthalic anhydride, respectively. The amount of anhydride added was calculated based on the degree of hydrolysis of the fibers (i.e., 88% for Fiber A) for the content of hydroxyl groups, and the degree of modification needed. For example, to achieve 25% chemical modification (i.e., conversion of 25% of hydroxyl groups), an amount of maleic anhydride, glutaric anhydride, or phthalic anhydride needed was 1.343 g, 1.564 g, or 2.03 g, respectively. The degree of polymerization of Fiber A was 1700. The curve of the nonwoven sample comprising fibers without modification (Comparative Example 1) is shown in a dotted line in each of FIGS. 6-8. The peaks in the FT-IR curves can be used to characterize the chemical modification and the degree of modification. For example, as shown in FIG. 7, the peak(s) in the range of 1734-1713 $cm^{-1}$ indicate a carbonyl group (C=O, stretch) such as that in the acetate group. The appearance of a peak at 1580 $cm^{-1}$ is from the unbonded carboxylate group at the end of MMM. The peaks of 1427 $cm^{-1}$ and 1374 $cm^{-1}$ correspond to a methylene group in the polymer backbone (i.e., $CH_2$ bending) and methyl in acetate side groups, respectively.

As shown in FIGS. 6-8, unbonded carboxyl groups at the end of anhydride moiety after the ring-opening reaction can be seen based on the peak between 1600 $cm^{-1}$ and 1520 $cm^{-1}$. This illustrates that the carboxylate groups are not crosslinked in the resulting modified polymers.

For the nonwoven samples made for solubility and mechanical testing, the fibers included 98.25% of Fiber A and 1.75% of polyethylene (PE)/polyethylene terephthalate (PET). The fibers are disposed between stainless steel meshes. The bonding temperature of the through-air process was selected from 120° C., 160° C., or 180° C.

Example 16

Figure 9:
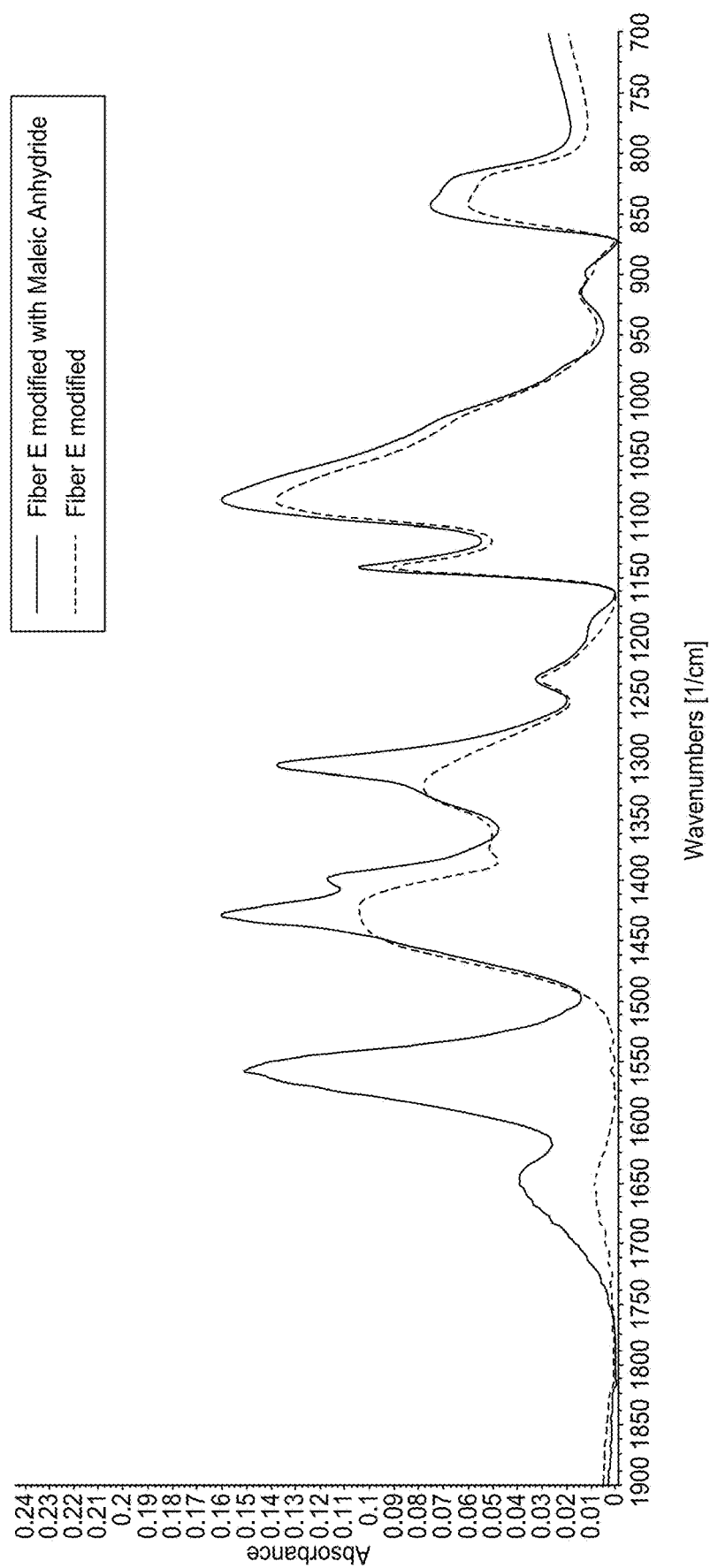
FIG. 9 shows ATR-FTIR results of a plurality of fibers (Fiber E) without and with chemical modification with maleic anhydride in THF at 60° C. for 5 hours, according to example embodiments.

Fibers (Fiber E) having PVOH copolymer with 99.99% degree of hydrolysis were chemically modified with maleic anhydride in THF at 60° C. for 5 hours to provide Example 16. Fiber E without treatment is Comparative Example 2, which is not readily water-soluble. FIG. 9 shows ATR-FTIR results of Example 16 and Comparative Example 2. A new peak around 1580 cm$^{-1}$ appeared after the chemical modification. The FT-IR results further confirmed that the chemical modification reaction occurs at the hydroxyl groups of vinyl alcohol moieties (i.e., the backbone of the PVOH copolymer), not at the vinyl acetate moieties. The modified fibers are water-soluble.

Examples 17-20

Figure 10:
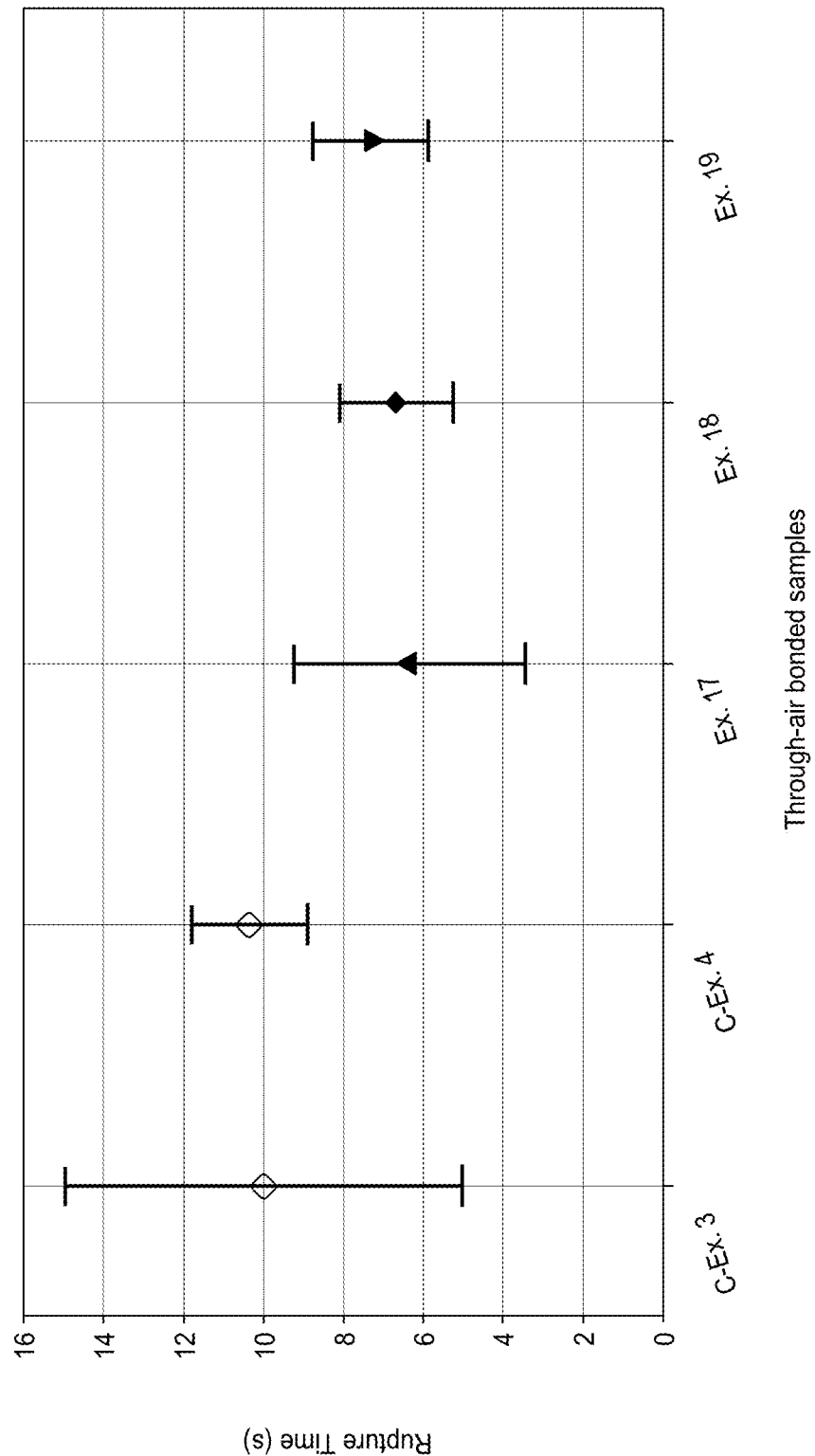
FIG. 10 shows rupture time (seconds) of through-air nonwoven webs having a plurality of fibers (Fiber A) without and with chemical modification with an anhydride such as maleic anhydride, glutaric anhydride, or phthalic anhydride, in THF at 60° C. for 5 hours, according to example embodiments.

FIG. 10 shows rupture time of through-air bonded nonwoven webs having fibers (Fiber A) without and with chemical modification with an anhydride, such as maleic anhydride, glutaric anhydride, or phthalic anhydride, in THF at 60° C. for 5 hours. In FIG. 10, Comparative Examples 3 and 4 ("CEx. 3" and "CEx. 4" as labelled in FIG. 10) are through-air bonded nonwoven webs having fibers (Fiber A) without chemical modification, while the fibers were immersed in THF at 60° C. for 5 hours, and then dried before the bonding process. The bonding temperature of Comparative Examples 3 and 4 was 160° C. and 180° C., respectively. Comparative Examples 3 and 4 are called positive controls. In Example 17 ("Ex. 17"), Example 18 ("Ex. 18"), and Example 19 ("Ex. 19"), the fibers were chemically modified with maleic anhydride, glutaric anhydride, and phthalic anhydride, respectively. The bonding temperature was 160° C. for Examples 17, and 180° C. for Examples 18 and 19. In these through-air bonded nonwoven samples including the comparative examples described herein, the fibers initially included 98.25% Fiber A and 1.75% of PE/PET.

Figure 11:
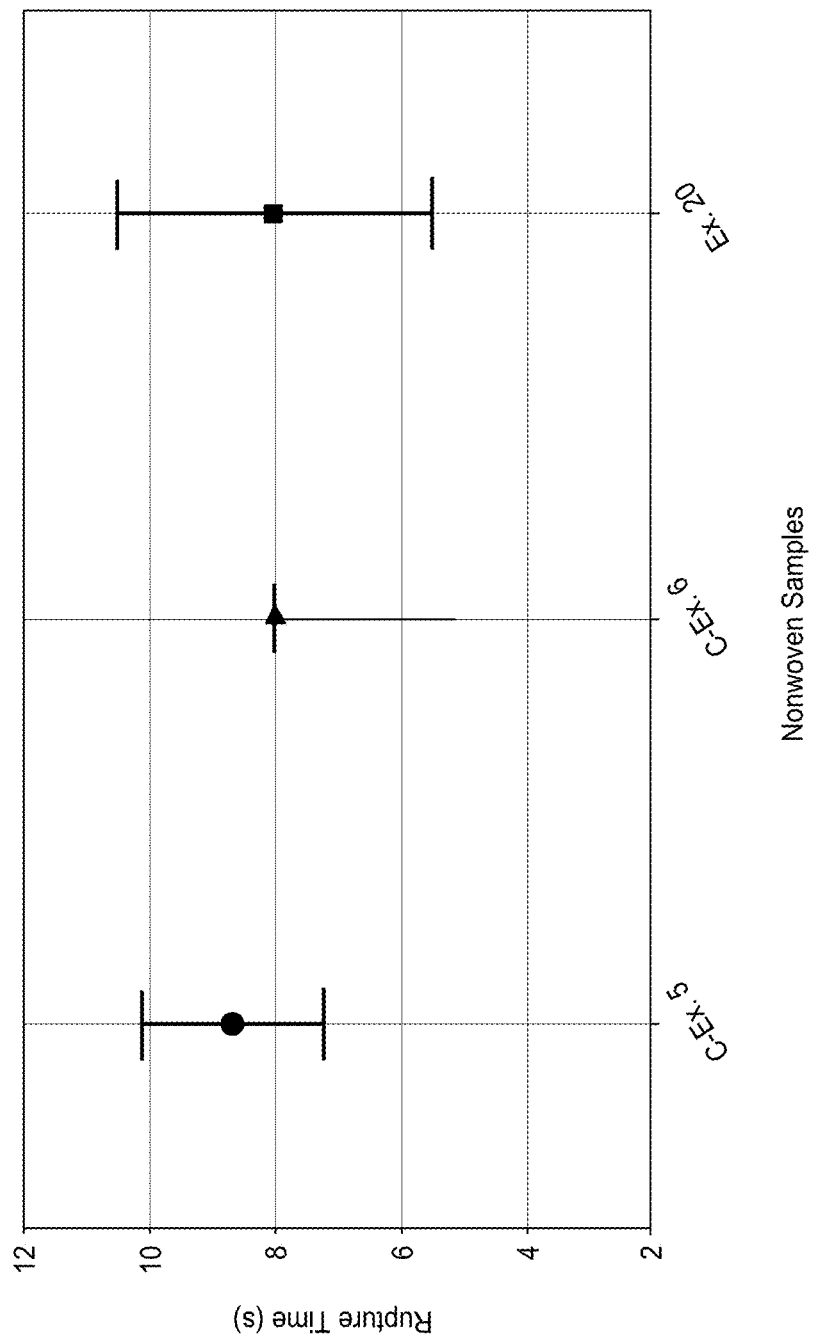
FIG. 11 shows rupture time (seconds) of nonwoven webs having a plurality of fibers (Fiber A) without and with chemical modification with maleic anhydride in DCM at room temperature for 5 hours, according to example embodiments.

FIG. 11 shows rupture time of nonwoven webs having fibers (Fiber A) without and with chemical modification with maleic anhydride in DCM at room temperature for 5 hours. The nonwoven webs were made using calendaring bonding (30 gsm). Comparative Example 5 ("CEx. 5") and Comparative Example 6 ("CEx. 6") as labelled in FIG. 11 are nonwoven webs having fibers (Fiber A) without chemical modification, except that Comparative Example 6 was treated in DCM at room temperature for 5 hours. Example 20 ("Ex. 20") was chemically treated with maleic anhydride in DCM at room temperature for 5 hours. In the calendaring bonded samples including the comparative examples described herein, the initial fibers included 100% of Fiber A without any other fibers such as PE/PET.

As shown in FIGS. 10-11, with chemical modification, solubility of the nonwoven samples is maintained. This also indicates that a cross-linking reaction does not occur. Otherwise, the solubility will be hindered to show a different solubility profile.

Figure 12:
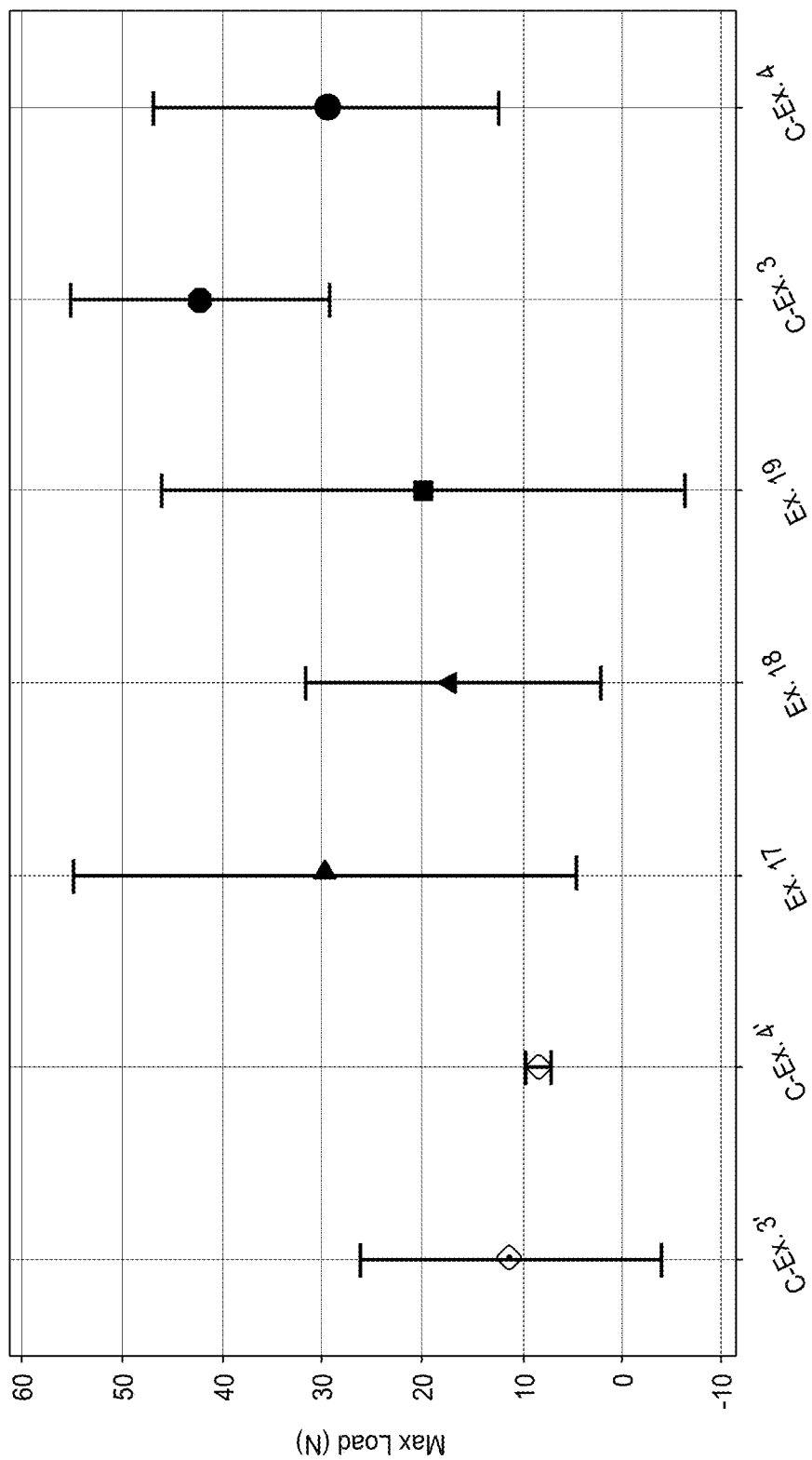
FIG. 12 shows tensile strength of through-air nonwoven webs having a plurality of fibers (Fiber A) without and with chemical modification with an anhydride such as maleic anhydride, glutaric anhydride, or phthalic anhydride, in THF at 60° C. for 5 hours, according to example embodiments.

FIG. 12 shows tensile strength of through-air nonwoven webs having fibers (Fiber A) without and with chemical modification with an anhydride, such as maleic anhydride, glutaric anhydride, or phthalic anhydride, in THF at 60° C. for 5 hours. The samples include Examples 17-19 and Comparative Examples 3-4 as positive controls as described above. Two additional Comparative Examples (CEx. 3' and CEx. 4') were also tested. CEx. 3' and CEx. 4' correspond to CEx. 3 and CEx. 4, respectively, except that the fibers were not immersed in THF at 60° C. for 5 hours, and were directly through-air bonded at 160° C. and 180° C., respectively.

Figure 13:
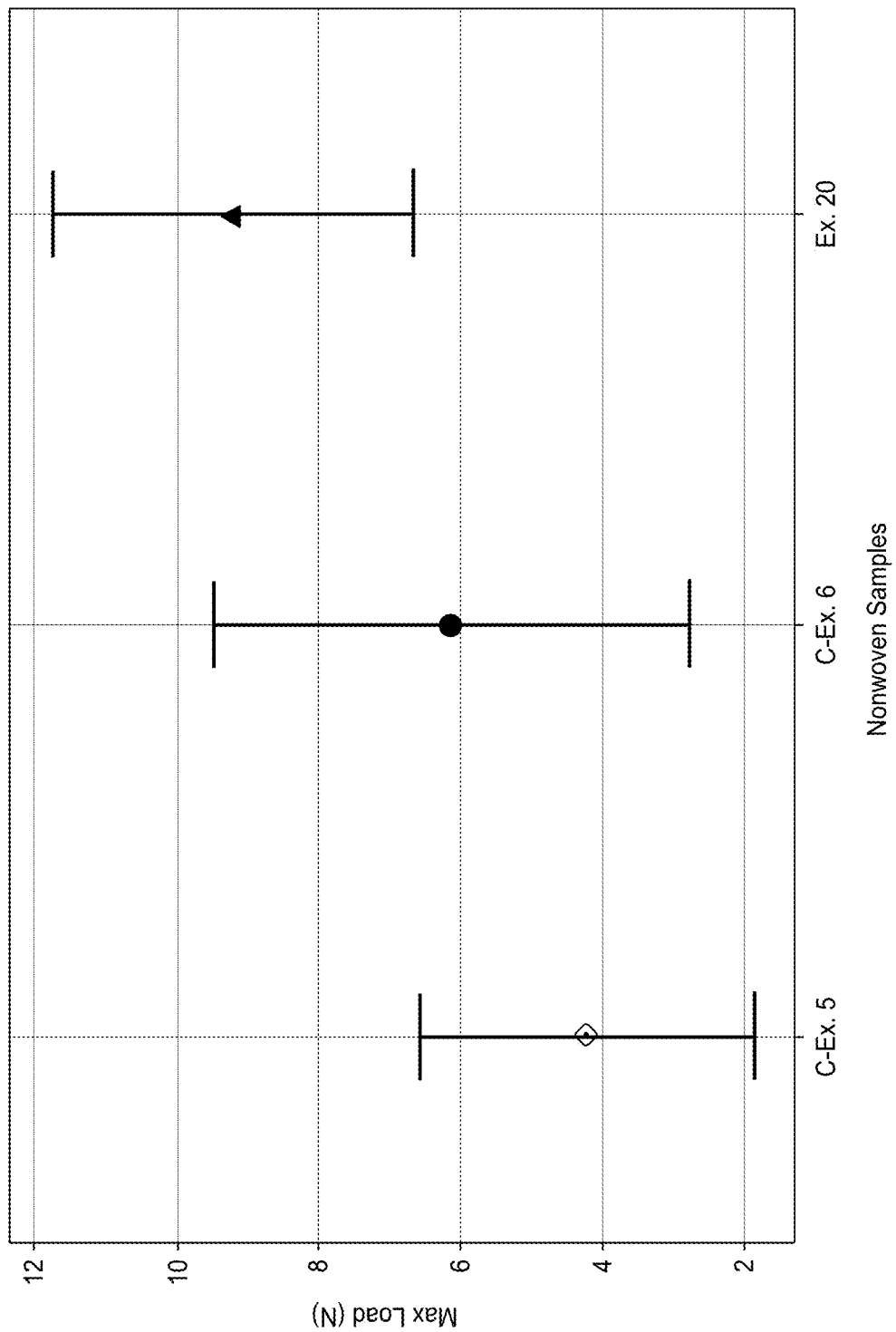
FIG. 13 shows tensile strength of nonwoven webs having a plurality of fibers (Fiber A) without and with chemical modification with maleic anhydride in DCM at room temperature for 5 hours, according to example embodiments.

FIG. 13 shows tensile strength of nonwoven webs having fibers (Fiber A) without and with chemical modification with maleic anhydride in DCM at room temperature for 5 hours, including Example 20 and Comparative Examples 5-6 as described above.

As shown in FIG. 12, the through-air samples having modified fibers have tensile strength slightly higher than those of Comparative Examples without modification. As shown in FIG. 13, the increase in tensile strength resulting from chemical modification is more significant for the nonwoven samples made by calendar bonding.

Figure 14:
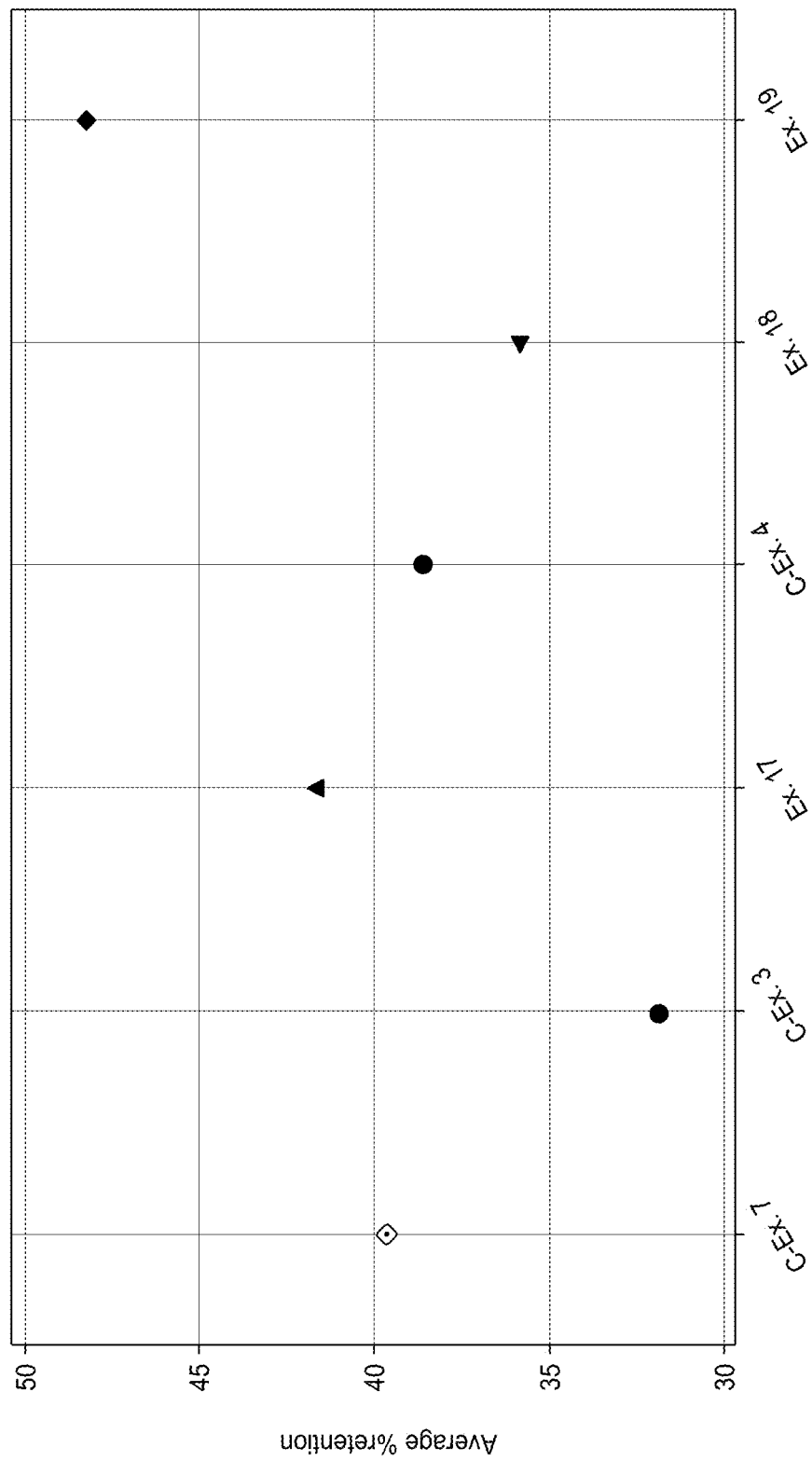
FIG. 14 shows a glycerin holding capacity (in percentage of retention) of through-air nonwoven webs having a plurality of fibers (Fiber A) without and with chemical modification with an anhydride, such as maleic anhydride, glutaric anhydride, or phthalic anhydride, in THF at 60° C. for 5 hours, wherein an initial loading of glycerin was 50%, according to example embodiments.

FIG. 14 shows a glycerin holding capacity of through-air bonded nonwoven webs having fibers (Fiber A) without and with chemical modification with an anhydride, such as maleic anhydride, glutaric anhydride, or phthalic anhydride, in THF at 60° C. for 5 hours. The initial loading of glycerin was 50%. The initial loading is an amount of glycerin applied to a sample based on the sample weight. For example, at 50% of loading, 0.5 g of glycerin was applied to 1 g of nonwoven sample. The glycerin holding capacity was measured as a percentage of retention of glycerin based on the weight percentage of glycerin retained in a nonwoven sample after a soaking time of one hour under ambient conditions. The retention of glycerin is an indicator of retention of polar additives used in nonwoven products. Additionally, glycerin is a preferred carrier in personal hygiene products. In FIG. 14, the samples include Examples 17, 18, and 19; and Comparative Examples 3-4 as described above. In addition, Comparative Example 7 ("CEx. 7") is a through-air bonded nonwoven web having fibers (Fiber A) without chemical modification and bonded at 120° C. The samples with chemical modification showed at least 10% increase in retention of glycerin. For example, compared to Comparative Example 3, Example 17 with maleic anhydride showed a significant increase in retention of glycerin.

Figure 15:
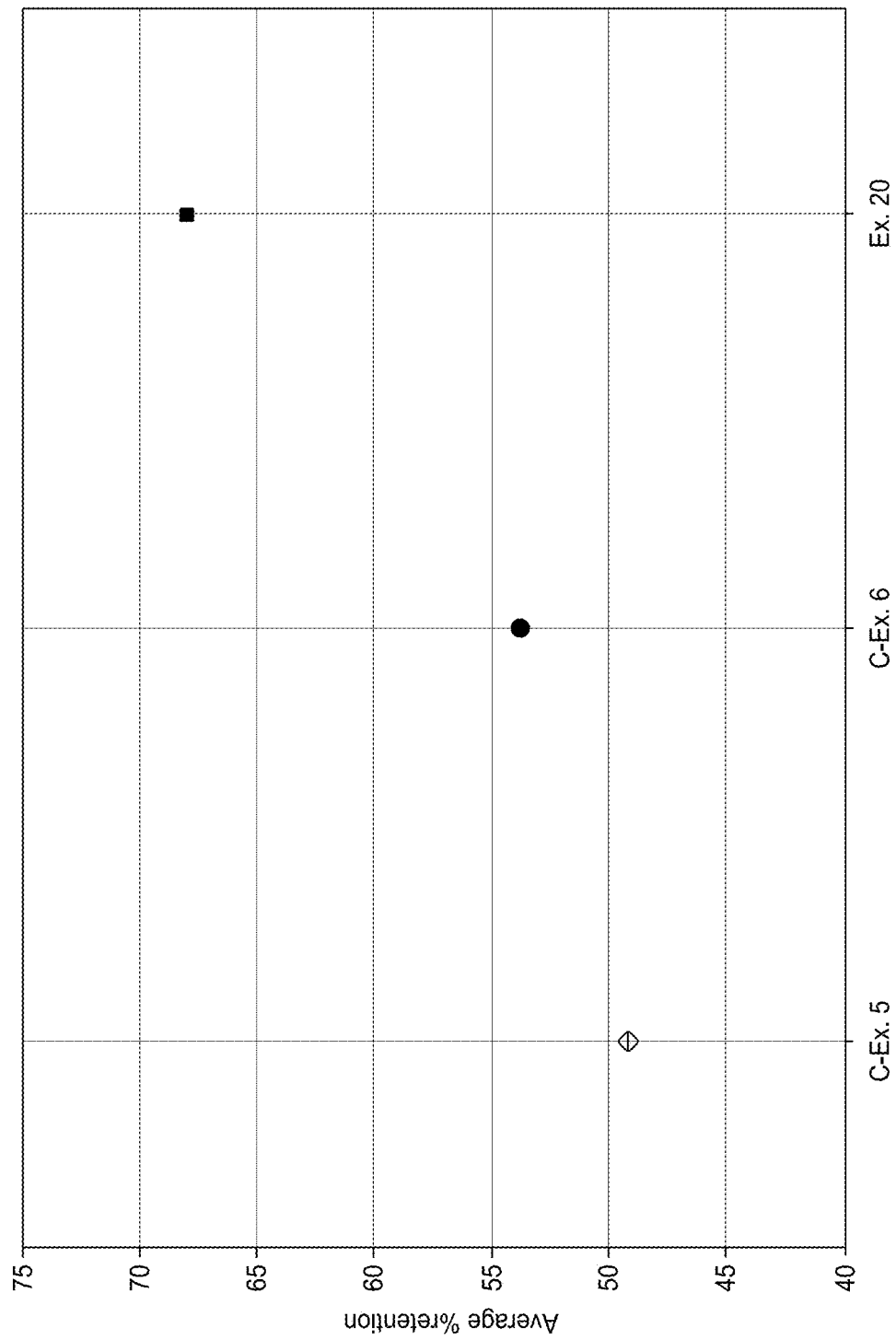
FIG. 15 shows a glycerin holding capacity (in percentage of retention) of nonwoven webs having a plurality of fibers (Fiber A) without and with chemical modification with maleic anhydride in in DCM at room temperature for 5 hours, wherein an initial loading of glycerin was 50%, according to example embodiments.

FIG. 15 shows a glycerin holding capacity of nonwoven webs having fibers (Fiber A) without and with chemical modification with maleic anhydride in DCM at room temperature for 5 hours, including Example 20 and Comparative Examples 5-6 made through calendar bonding as described above. The initial loading of glycerin was 50%. As shown in FIG. 15, Example 20 with maleic anhydride modification showed a significant increase (by at least 20%) in retention of glycerin at this low (50%) loading.

Figure 16:
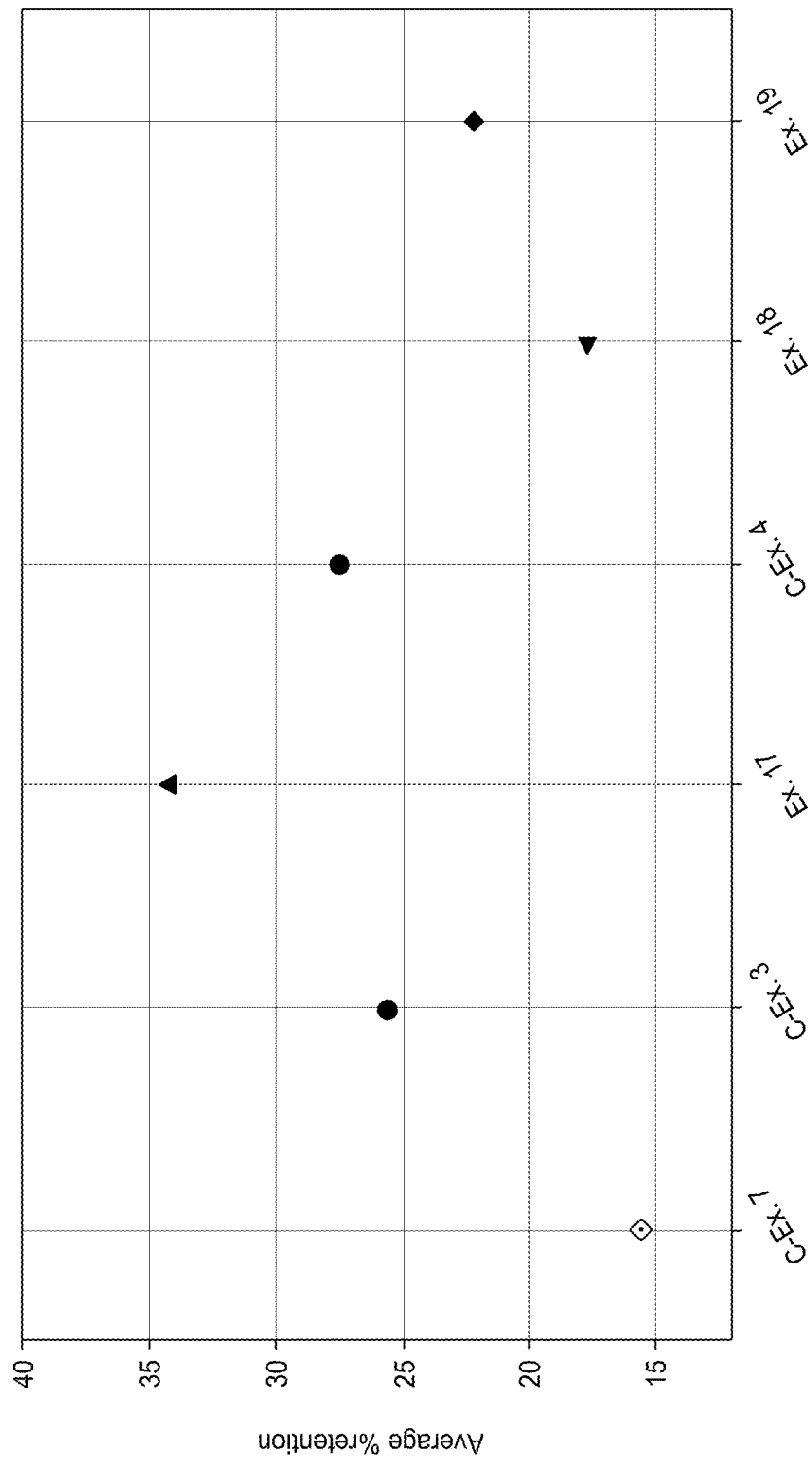
FIG. 16 shows a glycerin holding capacity (in percentage of retention) of through-air nonwoven webs having a plurality of fibers (Fiber A) without and with chemical modification with an anhydride, such as maleic anhydride, glutaric anhydride, or phthalic anhydride, in THF at 60° C. for 5 hours, wherein an initial loading of glycerin was 180%, according to example embodiments.
Figure 17:
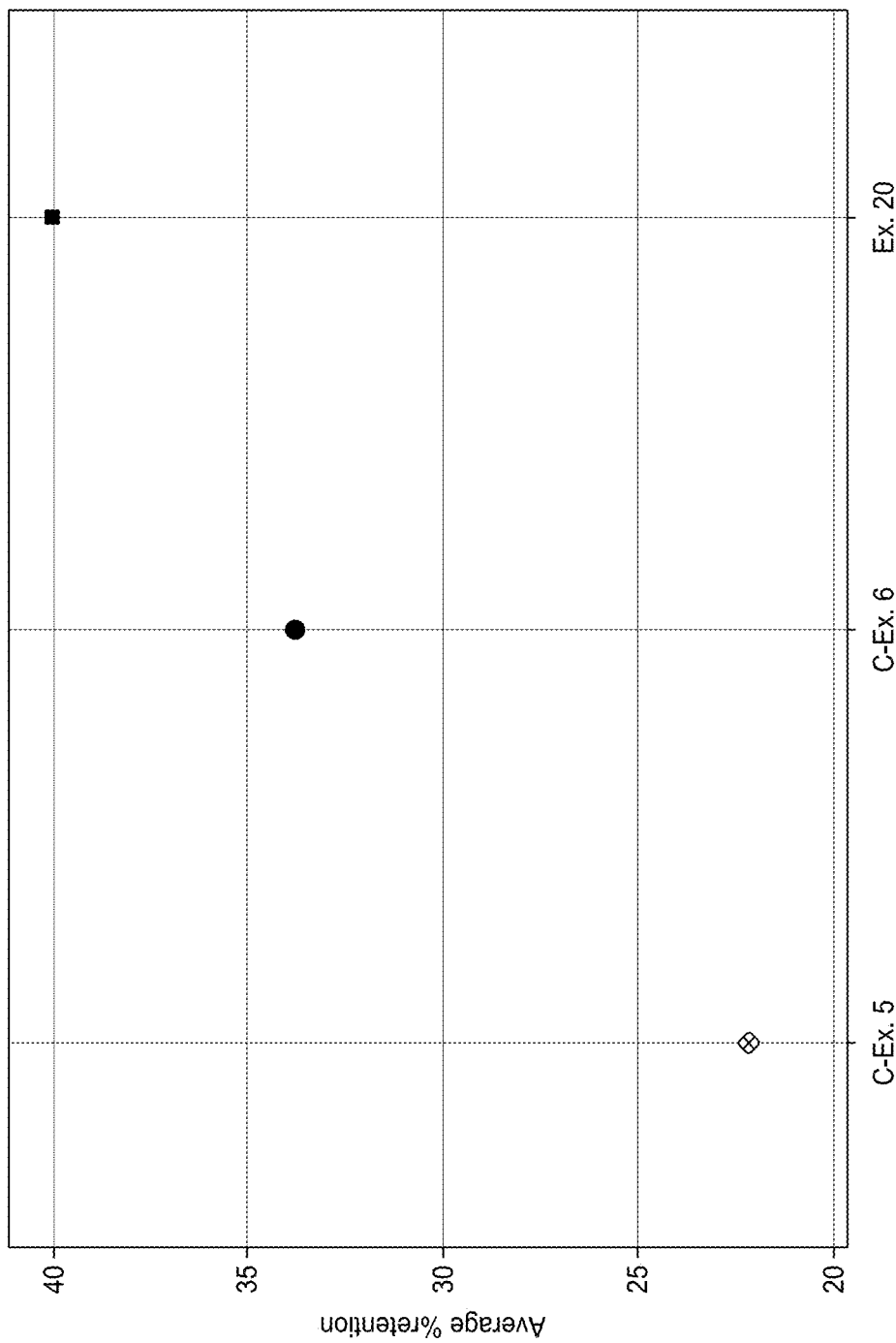
FIG. 17 shows a glycerin holding capacity (in percentage of retention) of nonwoven webs having a plurality of fibers (Fiber A) without and with chemical modification with maleic anhydride in in DCM at room temperature for 5 hours, wherein an initial loading of glycerin was 180%, according to example embodiments.

FIGS. 16 and 17 are similar to FIGS. 14 and 15, respectively, except that the initial loading of glycerin (180%) was much higher. As shown in FIGS. 16 and 17, maleic anhydride modification provides a significant increase (by at least 20%) in retention of glycerin at this high (180%) loading.

Some results of Examples 17-20 are also summarized in Tables 3 and 4.

TABLE 3

| Sample | Glycerin Holding Capacity (% retention at 50% Loading) | Glycerin Holding Capacity (% retention at 180% loading) | Solubility (23° C.) Rupture Time (s) | Tensile Strength Max Load (N) |
| --- | --- | --- | --- | --- |
| Modified Through-air Bonded Nonwoven (Maleic Anhydride, Ex. 17) | 41.61% Stdev: 5% | 34.21% Stdev: 4.99% | 6.33 Stdev: 0.94 | 26.62 Stdev: 8.23 |

TABLE 3-continued

| Sample | Glycerin Holding Capacity (% retention at 50% Loading) | Glycerin Holding Capacity (% retention at 180% loading) | Solubility (23° C.) Rupture Time (s) | Tensile Strength Max Load (N) |
|---|---|---|---|---|
| Modified Through-air Bonded Nonwoven (Glutaric Anhydride, Ex. 18) | 35.88% Stdev: 1.77% | 17.61% Stdev: 6.46% | 6.67 Stdev: 0.47 | 16.94N Stdev: 4.83 |
| Modified Through-air Bonded Nonwoven (Phthalic Anhydride, Ex. 19) | 48.22% Stdev: 19.3% | 22.22% Stdev: 2.66% | 7.33 Stdev: 0.47 sec | 19.70 Stdev: 8.58 |
| Non-modified Through-air Bonded Nonwoven (CEX' 4) | 39.65% Stdev: 7.91% | 15.59% Stdev: 5.10% | 29 Stdev: 12.19 | 8.37 Stdev: 0.38 |
| +control Non-modified Through-air Nonwoven (CEx 4) | 38.65% Stdev: 7.46% | 27.47% Stdev: 4.59% | 10.33 Stdev: 0.47 | 29.52 Stdev: 5.69 |

TABLE 4

| Sample | Glycerin Holding Capacity (% retention at 50% Loading) | Glycerin Holding Capacity (% retention at 180% Loading) | Solubility (23° C.) Rupture Time (s) | Tensile Strength, Max Load (N) |
|---|---|---|---|---|
| Modified Nonwoven (Maleic Anhydride, Ex. 20) | 67.96% Stdev: 3.80% | 40.04% Stdev: 3.17% | 8 Stdev: 0.82 | 9.20 Stdev: |
| Non-modified Nonwoven (CEx 5) | 49.23% Stdev: 13.33% | 22.11% Stdev: 4.80% | 8.67 Stdev: 0.47 | 4.21 Stdev: 2.05 |
| +control Nonwoven (CEx 6) | 53.74% Stdev: 7.00% | 33.77% Stdev: 5.58% | 8 Stdev: 0.00 | 6.13 Stdev: 1.82 |

Example 21

Figure 18:
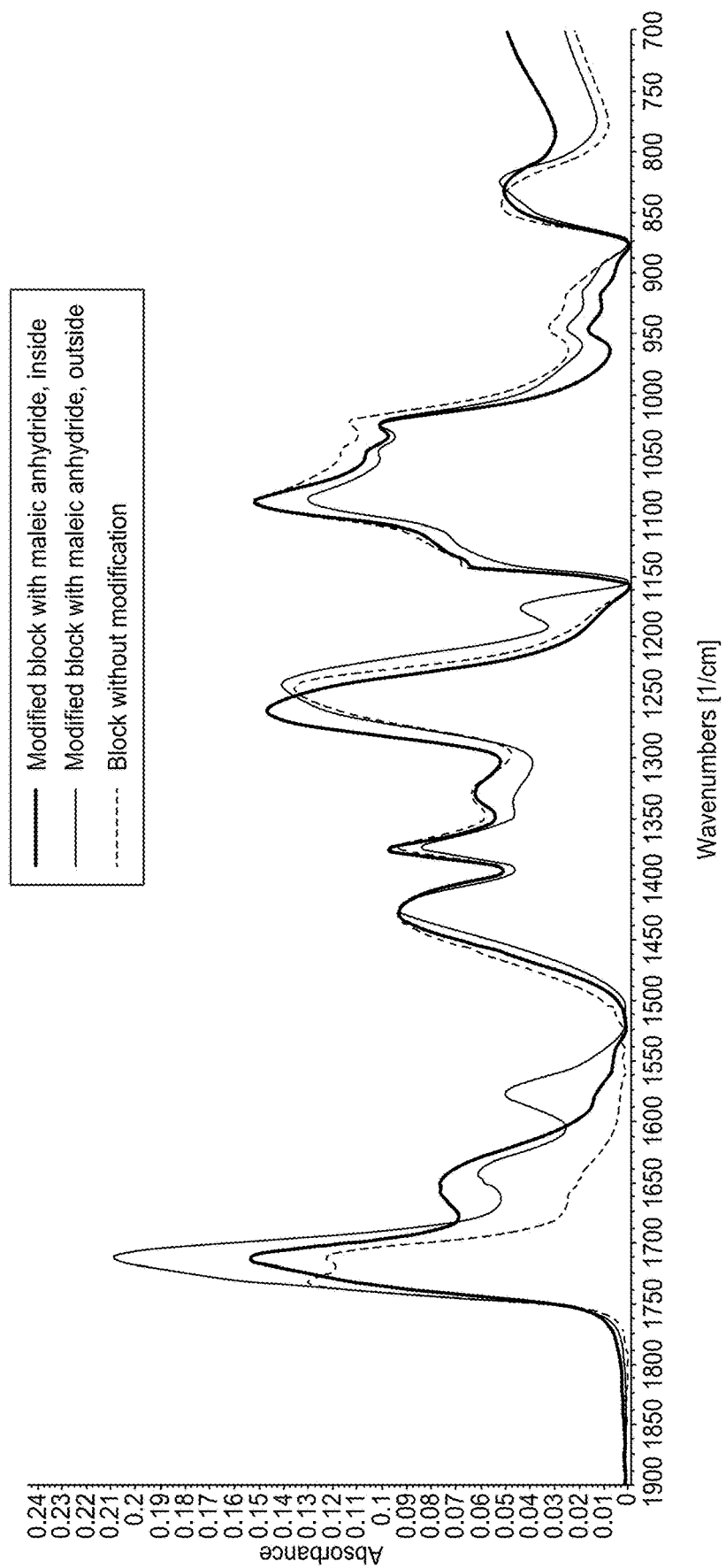
FIG. 18 shows ATR-FTIR results of an interior region ("inside region") and a surface region ("outside region") of an exemplary block comprising a copolymer of vinyl acetate and vinyl alcohol without and with chemical modification with maleic anhydride in in THF at 60° C. for 5 hours, according to example embodiments.

FIG. 18 shows ATR-FTIR results of an interior region ("inside region") and a surface region ("outside region") of an exemplary block comprising a copolymer of vinyl acetate and vinyl alcohol without and with chemical modification with maleic anhydride in in THF at 60° C. for 5 hours. The block sample was made of a copolymer of vinyl acetate and vinyl alcohol having a degree of hydrolysis of 88%. Each block sample had a size of 1.5 centimeters (cm)×1.5 cm×0.5 cm. The sample was modified with maleic anhydride in in THF at 60° C. for 5 hours. After modification and drying, the sample having a thickness in a range of from 0.1 mm to 0.5 mm was cut from the block sample and then tested using ATR-FTI R. The modified sample is Example 21, and the FT-IR curve of the initial block without modification is shown in a dotted line in FIG. 18. Based on the FTIR results, pendent groups resulting from esterification of maleic anhydride are mainly limited to the surface region of the block, therefore, creating a relatively higher degree of modification in the outer region and a relatively lower degree of modification in the inner region of the sample. This confirmed that the fibers modified under the same conditions have a core-sheath structure as described herein.

The foregoing description is given for clearness of understanding only, and no unnecessary limitations should be understood therefrom, as modifications within the scope of the disclosure may be apparent to those having ordinary skill in the art.

All patents, publications and references cited herein are hereby fully incorporated by reference. In case of conflict between the present disclosure and incorporated patents, publications and references, the present disclosure should control.

What is claimed is:

1. A post-process modified, water-soluble fiber having a surface region and an interior region, the fiber comprising:
    a polymer comprising at least one of a vinyl acetate moiety or a vinyl alcohol moiety chemically modified after fiber formation with a modification agent,
    the fiber having a transverse cross-section including the interior region comprising the polymer having a first degree of modification and the surface region comprising the polymer having a second degree of modification greater than the first degree of modification.

2. The fiber according to claim 1, wherein the transverse cross-section of the fiber has an increasing gradient in a degree of modification of the polymer from the interior region to the surface region.

3. The fiber according to claim 1, wherein the polymer comprising at least one of a vinyl acetate moiety or a vinyl alcohol moiety without modification comprises a polyvinyl alcohol homopolymer, a polyvinyl acetate homopolymer, a polyvinyl alcohol copolymer, or any combination thereof.

4. A post-process modified fiber having a surface region and an interior region, the fiber comprising:
    a polymer comprising at least one of a vinyl acetate moiety or a vinyl alcohol moiety chemically modified after fiber formation with a modification agent, the fiber having a transverse cross-section including the interior region comprising the polymer having a first degree of modification and the surface region comprising the polymer having a second degree of modification greater than the first degree of modification, wherein the polymer comprising at least one of a vinyl acetate moiety or a vinyl alcohol moiety without modification comprises a polyvinyl acetate homopolymer, a polyvinyl alcohol copolymer comprising a copolymer of vinyl acetate and vinyl alcohol, or any combination thereof.

5. The fiber according to claim 4, wherein the polyvinyl alcohol copolymer comprises an anionic modification.

6. The fiber according to claim 5, wherein the anionic modification comprises a carboxylate, a sulfonate, or a combination thereof.

7. A post-process modified fiber having a surface region and an interior region, the fiber comprising:

a polymer comprising at least one of a vinyl acetate moiety or a vinyl alcohol moiety chemically modified after fiber formation with a modification agent, wherein the polymer comprising at least one of a vinyl acetate moiety or a vinyl alcohol moiety chemically modified with the modification agent is chemically bonded with a moiety of the modification agent, the fiber having a transverse cross-section including the interior region comprising the polymer having a first degree of modification and the surface region comprising the polymer having a second degree of modification greater than the first degree of modification.

8. The fiber according to claim 7, wherein the modification agent comprises an anhydride, and the modification agent moiety comprises a carboxyl acid from the anhydride or a salt thereof.

9. The fiber according to claim 7, wherein the anhydride is selected from acetic anhydride, propionic anhydride, isobutyric anhydride, maleic anhydride, phthalic anhydride, glutaric anhydride, itaconic anhydride, citraconic anhydride, glutaconic anhydride, or any combination thereof.

10. The fiber according to claim 7, wherein the polymer comprising at least one of a vinyl acetate moiety or a vinyl alcohol moiety before modification is a copolymer of vinyl acetate and vinyl alcohol having a degree of hydrolysis in a range of from about 79% to about 99%, and the modification agent comprises maleic anhydride.

11. The fiber according to claim 1, further comprising an additional polymer.

12. The fiber according to claim 11, wherein the additional polymer is selected from the group consisting of a polyvinyl alcohol, a polyvinyl acetate, a polyacrylate, a water-soluble acrylate copolymer, a polyvinyl pyrrolidone, a polyethylenimine, a pullulan, a guar gum, a gum Acacia, a xanthan gum, a carrageenan, a starch, a modified starch, a polyalkylene oxide, a polyacrylamide, a polyacrylic acid, a cellulose, a cellulose ether, a cellulose ester, a cellulose amide, a polycarboxylic acid, a polyaminoacid, a polyamide, a gelatin, a dextrin, copolymers of the foregoing, and any combination of any of the foregoing additional polymers or copolymers.

13. The fiber according to claim 1, wherein the fiber has a dissolution time of less than 200 seconds in water at about 23° C.

14. A post-process modified, water-soluble fiber having a longitudinal axis and a transverse cross-section perpendicular to the longitudinal axis, the fiber further having a core-sheath structure along at least a portion of the longitudinal axis, the fiber comprising:

a core region comprising a polymer comprising at least one of a vinyl acetate moiety and a vinyl alcohol moiety chemically modified after fiber formation with a modification agent and having a first degree of modification, and a sheath region comprising the polymer comprising at least one of a vinyl acetate moiety and a vinyl alcohol moiety chemically modified after fiber formation with the modification agent and having a second degree of modification greater than the first degree of modification.

15. The fiber according to claim 14, further comprising an intermediate region disposed between the core region and the sheath region, the intermediate region comprising the polymer comprising at least one of a vinyl acetate moiety and a vinyl alcohol moiety chemically modified with the modification agent and having a third degree of modification greater than the first degree of modification and less than the second degree of modification.

16. The fiber according to claim 15, comprising a plurality of intermediate regions disposed between the core region and the sheath region, such that the transverse cross-section of the fiber has a gradient in the degree of modification from the core region to the sheath region.

17. The fiber according to claim 14, wherein the transverse cross-section of the fiber has a first mean radius and the sheath region has a second mean radius of 0.5% to 12% of the first mean radius.

18. The fiber according to claim 15, wherein the polymer in the core region, the polymer in the sheath region, and optionally the polymer in the intermediate region have an equal degree of polymerization.

19. The fiber according to claim 14, wherein the polymer comprising at least one of a vinyl acetate moiety or a vinyl alcohol moiety without modification comprises a polyvinyl alcohol homopolymer, a polyvinyl acetate homopolymer, a polyvinyl alcohol copolymer, or any combination thereof.

20. The fiber according to claim 19, wherein the polyvinyl alcohol copolymer is a copolymer of vinyl acetate and vinyl alcohol.

21. The fiber according to claim 14, wherein the polymer comprising at least one of a vinyl acetate moiety or a vinyl alcohol moiety chemically modified with the modification agent is chemically bonded with a moiety of the modification agent.

22. The fiber according to claim 14, wherein the modification agent comprises an anhydride.

23. The fiber according to claim 22, wherein the anhydride is selected from acetic anhydride, propionic anhydride, isobutyric anhydride, maleic anhydride, phthalic anhydride, glutaric anhydride, itaconic anhydride, citraconic anhydride, glutaconic anhydride, or any combination thereof.

24. A nonwoven web comprising the modified fiber according to claim 1.

25. A multilayer nonwoven web comprising a first layer comprising the nonwoven web according to claim 24.

26. A pouch comprising the nonwoven web according to claim 25 in the form of a pouch defining an interior pouch volume.

27. A sealed article comprising the nonwoven web according to claim 24.

28. A flushable article comprising the nonwoven web according to claim 24.

29. A wearable absorbent article, comprising:
an absorbent core having a wearer facing side and an outer facing side; and
a liquid acquisition layer,
wherein the liquid acquisition layer comprises a nonwoven web according to claim 24.

* * * * *